US012378540B1

(12) United States Patent
Kariolis et al.

(10) Patent No.: US 12,378,540 B1
(45) Date of Patent: Aug. 5, 2025

(54) FUSION PROTEINS COMPRISING ACID ALPHA-GLUCOSIDASE ENZYMES AND METHODS THEREOF

(71) Applicant: DENALI THERAPEUTICS INC., South San Francisco, CA (US)

(72) Inventors: Mihalis S. Kariolis, San Mateo, CA (US); Melina Lenser, San Francisco, CA (US); Cathal S. Mahon, San Francisco, CA (US); Hanh Giai Ngo, San Bruno, CA (US); Yashas Rajendra, San Mateo, CA (US); Shrishti Tyagi, Santa Clara, CA (US); Tianao Yuan, San Mateo, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 19/081,211

(22) Filed: Mar. 17, 2025

Related U.S. Application Data

(63) Continuation of application No. PCT/US2024/060936, filed on Dec. 19, 2024.

(60) Provisional application No. 63/612,862, filed on Dec. 20, 2023.

(51) Int. Cl.
*C12N 9/24* (2006.01)
*A61P 3/00* (2006.01)
*A61K 38/00* (2006.01)

(52) U.S. Cl.
CPC .............. *C12N 9/2402* (2013.01); *A61P 3/00* (2018.01); *C12Y 302/0102* (2013.01); *A61K 38/00* (2013.01); *C07K 2319/30* (2013.01)

(58) Field of Classification Search
CPC . C12Y 302/0102; C07K 2319/33; C12N 9/24
See application file for complete search history.

(56) References Cited

U.S. PATENT DOCUMENTS

| | | |
|---|---|---|
| 8,546,319 B2 | 10/2013 | Starr et al. |
| 10,759,864 B2 | 9/2020 | Sonoda et al. |
| 10,870,837 B2 | 12/2020 | Henry et al. |
| 10,940,185 B2 | 3/2021 | Yasukawa et al. |
| 11,643,446 B2 | 5/2023 | Cherf et al. |
| 11,795,232 B2 | 10/2023 | Chen et al. |
| 11,866,742 B2 | 1/2024 | Henry et al. |
| 11,884,944 B2 | 1/2024 | Giese et al. |
| 11,912,778 B2 | 2/2024 | Chen et al. |
| 12,162,948 B2 | 12/2024 | Chen et al. |
| 2005/0100986 A1 | 5/2005 | Verma et al. |
| 2005/0142141 A1 | 6/2005 | Pardridge |
| 2009/0117091 A1 | 5/2009 | Lebowitz et al. |
| 2015/0322149 A1 | 11/2015 | Bohrmann et al. |
| 2019/0225700 A1 | 7/2019 | Koshimura et al. |
| 2019/0352335 A1 | 11/2019 | Jeong et al. |
| 2020/0157172 A1 | 5/2020 | Heo et al. |
| 2021/0009984 A1 | 1/2021 | Jung et al. |
| 2022/0184186 A1 | 6/2022 | Andersen et al. |
| 2023/0092681 A1 | 3/2023 | Arguello et al. |
| 2023/0220100 A1 | 7/2023 | Cygnar et al. |
| 2023/0265137 A1 | 8/2023 | Cherf et al. |
| 2023/0381286 A1 | 11/2023 | Dennis et al. |
| 2024/0018253 A1 | 1/2024 | Chen et al. |
| 2024/0141058 A1 | 5/2024 | Chen et al. |
| 2024/0150736 A1 | 5/2024 | Giese et al. |
| 2025/0018015 A1 | 1/2025 | Arguello et al. |
| 2025/0136963 A1 | 5/2025 | Adusumilli et al. |

FOREIGN PATENT DOCUMENTS

| | | |
|---|---|---|
| EP | 3409771 A1 | 12/2018 |
| WO | 2003057179 A2 | 7/2003 |
| WO | 2014152940 A1 | 9/2014 |
| WO | 2015192092 A1 | 12/2015 |
| WO | 2016207240 A1 | 12/2016 |
| WO | 2017100467 A2 | 6/2017 |
| WO | 2018152326 A1 | 8/2018 |
| WO | 2019032955 A1 | 2/2019 |
| WO | 2019033046 A1 | 2/2019 |
| WO | 2019070577 A1 | 4/2019 |
| WO | 2019246071 A1 | 12/2019 |
| WO | 2020206320 A1 | 10/2020 |
| WO | 2021133907 A1 | 7/2021 |
| WO | 2022081765 A1 | 4/2022 |
| WO | 2021158986 A9 | 7/2022 |
| WO | 2023004156 A1 | 1/2023 |
| WO | 2023114485 A1 | 6/2023 |
| WO | 2024026474 A1 | 2/2024 |
| WO | 2024121755 A1 | 6/2024 |

OTHER PUBLICATIONS

Patent Cooperation Treaty, International Search Report and Written Opinion for PCT/US2024/060936, 22 pages, dated May 27, 2025.
Byrne, et al., "Cipaglucosidase alfa plus miglustat: linking mechanism of action to clinical outcomes in late-onset Pompe disease", Front Neurol 15, 1451512, doi: 10.3389/fneur.2024.1451512, 15 pages (2024); Erratum in: Front Neurol. 15:1540452. doi: 10.3389/fneur.2024.1540452, 3 pages (2025).
Johnsen, et al., "Targeting the transferrin receptor for brain drug delivery", Progress in Neurobiology 181, 101665, 1-30 (2019).
Pardridge, W, "Targeted Delivery of Protein and Gene Medicines Through the Blood-Brain Barrier", Clinical Pharmacology & Therapeutics 97 (4), 347-361 (Advanced Online Publication 2014; in Issue 2015).
Patent Cooperation Treaty, Communication Relating to the Results of the Partial International Search and Written Opinion for PCT/US2024/060936, 10 pages, dated Apr. 4, 2025.
Unnisa, et al., "Gene Therapy Developments for Pompe Disease", Biomedicines 10 (302), doi: 10.3390/biomedicines/10020302, 26 pages (2022).

*Primary Examiner* — Tekchand Saidha
(74) *Attorney, Agent, or Firm* — Viksnins Harris Padys Malen LLP

(57) ABSTRACT

Provided herein are proteins, which are capable of being transported across the blood-brain barrier (BBB) and comprise an acid alpha-glucosidase (GAA) enzyme-Fc fusion polypeptide. Certain embodiments also provide methods of using such proteins to treat Pompe disease.

17 Claims, 18 Drawing Sheets
Specification includes a Sequence Listing.

```
                        SEQUENCE LISTING

Sequence total quantity: 70
SEQ ID NO: 1            moltype = AA  length = 217
FEATURE                 Location/Qualifiers
source                  1..217
                        mol_type = protein
                        organism = Homo sapiens
SEQUENCE: 1
APELLGGPSV FLFPPKPKDT LMISRTPEVT CVVVDVSHED PEVKFNWYVD GVEVHNAKTK   60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPGK                           217

SEQ ID NO: 2            moltype = AA  length = 216
FEATURE                 Location/Qualifiers
source                  1..216
                        mol_type = protein
                        organism = Homo sapiens
SEQUENCE: 2
APELLGGPSV FLFPPKPKDT LMISRTPEVT CVVVDVSHED PEVKFNWYVD GVEVHNAKTK   60
PREEQYNSTY RVVSVLTVLH QDWLNGKEYK CKVSNKALPA PIEKTISKAK GQPREPQVYT  120
LPPSRDELTK NQVSLTCLVK GFYPSDIAVE WESNGQPENN YKTTPPVLDS DGSFFLYSKL  180
TVDKSRWQQG NVFSCSVMHE ALHNHYTQKS LSLSPG                            216

SEQ ID NO: 3            moltype = AA  length = 110
FEATURE                 Location/Qualifiers
source                  1..110
                        mol_type = protein
                        organism = synthetic construct
SEQUENCE: 3
APELLGGPSV FLFPPKPKDT LMISRTPEVT CVVVDVSHED PEVKFNWYVD GVEVHNAKTK   60
PREEQYNSTY RVVSVLTVLH QDWLNGKEYK CKVSNKALPA PIEKTISKAK              110

SEQ ID NO: 4            moltype = AA  length = 107
FEATURE                 Location/Qualifiers
source                  1..107
                        mol_type = protein
                        organism = synthetic construct
SEQUENCE: 4
```

```
GQPREPQVYT LPPSRDELTK NQVSLTCLVK GFYPSDIAVE WESNGQPENN YKTTPPVLDS    60
DGSFFLYSKL TVDKSRWQQG NVFSCSVMHE ALHNHYTQKS LSLSPGK                107

SEQ ID NO: 5              moltype = AA  length = 15
FEATURE                   Location/Qualifiers
source                    1..15
                          mol_type = protein
                          organism = Homo sapiens
SEQUENCE: 5
EPKSCDKTHT CPPCP                                                    15

SEQ ID NO: 6              moltype = AA  length = 10
FEATURE                   Location/Qualifiers
source                    1..10
                          mol_type = protein
                          organism = Homo sapiens
SEQUENCE: 6
DKTHTCPPCP                                                          10

SEQ ID NO: 7              moltype = AA  length = 760
FEATURE                   Location/Qualifiers
source                    1..760
                          mol_type = protein
                          organism = Homo sapiens
SEQUENCE: 7
MMDQARSAFS NLFGGEPLSY TRFSLARQVD GDNSHVEMKL AVDEEENADN NTKANVTKPK    60
RCSGSICYGT IAVIVFFLIG FMIGYLGYCK GVEPKTECER LAGTESPVRE EPGEDFPAAR   120
RLYWDDLKRK LSEKLDSTDF TGTIKLLNEN SYVPREAGSQ KDENLALYVE NQFREFKLSK   180
VWRDQHFVKI QVKDSAQNSV IIVDKNGRLV YLVENPGGYV AYSKAATVTG KLVHANFGTK   240
KDFEDLYTPV NGSIVIVRAG KITFAEKVAN AESLNAIGVL IYMDQTKFPI VNAELSFFGH   300
AHLGTGDPYT PGFPSPSFNHTQ FPPSRSSGLP NIPVQTISRA AAEKLFGNME GDCPSDWKTD   360
STCRMVTSES KNVKLTVSNV LKEIKILNIF GVIKGFVEPD HYVVVGAQRD AWGPGAAKSG   420
VGTALLLKLA QMFSDMVLKD GFQPSRSIIF ASWSAGDFGS VGATEWLEGY LSSLHLKAFT   480
YINLLGKAVLG TSNFKVSASP LLYTLIEKTM QNVKHPVTGQ FLYQDSNWAS KVEKLTLDNA   540
APPFLAYSGI PAVSFCFCED TDYPYLGTTM DTYKELIERI PELNKVARAA AEVAGQFVIK   600
LTHDVELNLD YERYNSQLLS FVRDLNQYRA DIKEMGLSLQ WLYSARGDFF RATSRLTTDF   660
GNAEKTDRFV MKKLNDRVMR VEYHFLSPYV SPKESPFRHV FWGSGSHTLP ALLENLKLRK   720
QNNGAFNETL FRNQLALATW TIQGAANALS GDVWDIDNEF                         760

SEQ ID NO: 8              moltype = AA  length = 181
FEATURE                   Location/Qualifiers
source                    1..181
                          mol_type = protein
                          organism = Homo sapiens
SEQUENCE: 8
NSVIIVDKNG RLVYLVENPG GYVAYSKAAT VTGKLVHANF GTKKDFEDLY TPVNGSIVIV    60
RAGKITFAEK VANAESLNAI GVLIYMDQTK FPIVNAELSF FGHAHLGTGD PYTPGFPSFN   120
HTQFPPSRSS GLPNIPVQTI SRAAAEKLFG NMEGDCPSDW KTDSTCRMVT SESKNVKLTV   180
S                                                                  181

SEQ ID NO: 9              moltype = AA  length = 217
FEATURE                   Location/Qualifiers
source                    1..217
                          mol_type = protein
                          organism = synthetic construct
SEQUENCE: 9
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLTCAVK GFYPSDIAVE WESNGQPENN YKTTPPVLDS DGSFFLVSKL   180
TVDKSRWQQG NVFSCSVMHE ALHNHYTQKS LSLSPGK                            217

SEQ ID NO: 10             moltype = AA  length = 216
FEATURE                   Location/Qualifiers
source                    1..216
                          mol_type = protein
                          organism = synthetic construct
SEQUENCE: 10
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLTCAVK GFYPSDIAVE WESNGQPENN YKTTPPVLDS DGSFFLVSKL   180
TVDKSRWQQG NVFSCSVMHE ALHNHYTQKS LSLSPG                             216

SEQ ID NO: 11             moltype = AA  length = 217
FEATURE                   Location/Qualifiers
source                    1..217
                          mol_type = protein
                          organism = synthetic construct
SEQUENCE: 11
APEAAGGPSV FLFPPKPKDT LMISRTPEVT CVVVDVSHED PEVKFNWYVD GVEVHNAKTK    60
```

```
PREEQYNSTY RVVSVLTVLH QDWLNGKEYK CKVSNKALPA PIEKTISKAK GQPREPQVYT    120
LPPSRDELTK NQVSLSCAVK GFYPSDIAVE WESNGQPENN YKTTPPVLDS DGSFFLVSKL    180
TVDKSRWQQG NVFSCSVMHE ALHNHYTQKS LSLSPGK                             217

SEQ ID NO: 12           moltype = AA   length = 216
FEATURE                 Location/Qualifiers
source                  1..216
                        mol_type = protein
                        organism = synthetic construct
SEQUENCE: 12
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT    120
LPPSRDELTK NQVSLSCAVK GFYPSDIAVE WESNGQPENN YKTTPPVLDS DGSFFLVSKL    180
TVDKSRWQQG NVFSCSVMHE ALHNHYTQKS LSLSPG                              216

SEQ ID NO: 13           moltype = AA   length = 217
FEATURE                 Location/Qualifiers
source                  1..217
                        mol_type = protein
                        organism = synthetic construct
SEQUENCE: 13
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALGA PIEKTISKAK GQPREPQVYT    120
LPPSRDELTK NQVSLSCAVK GFYPSDIAVE WESNGQPENN YKTTPPVLDS DGSFFLVSKL    180
TVDKSRWQQG NVFSCSVMHE ALHNHYTQKS LSLSPGK                             217

SEQ ID NO: 14           moltype = AA   length = 216
FEATURE                 Location/Qualifiers
source                  1..216
                        mol_type = protein
                        organism = synthetic construct
SEQUENCE: 14
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALGA PIEKTISKAK GQPREPQVYT    120
LPPSRDELTK NQVSLSCAVK GFYPSDIAVE WESNGQPENN YKTTPPVLDS DGSFFLVSKL    180
TVDKSRWQQG NVFSCSVMHE ALHNHYTQKS LSLSPG                              216

SEQ ID NO: 15           moltype = AA   length = 217
FEATURE                 Location/Qualifiers
source                  1..217
                        mol_type = protein
                        organism = synthetic construct
SEQUENCE: 15
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALSA PIEKTISKAK GQPREPQVYT    120
LPPSRDELTK NQVSLSCAVK GFYPSDIAVE WESNGQPENN YKTTPPVLDS DGSFFLVSKL    180
TVDKSRWQQG NVFSCSVMHE ALHNHYTQKS LSLSPGK                             217

SEQ ID NO: 16           moltype = AA   length = 216
FEATURE                 Location/Qualifiers
source                  1..216
                        mol_type = protein
                        organism = synthetic construct
SEQUENCE: 16
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALSA PIEKTISKAK GQPREPQVYT    120
LPPSRDELTK NQVSLSCAVK GFYPSDIAVE WESNGQPENN YKTTPPVLDS DGSFFLVSKL    180
TVDKSRWQQG NVFSCSVMHE ALHNHYTQKS LSLSPG                              216

SEQ ID NO: 17           moltype = AA   length = 217
FEATURE                 Location/Qualifiers
source                  1..217
                        mol_type = protein
                        organism = synthetic construct
SEQUENCE: 17
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT    120
LPPSRDELTK NQVSLWCLVK GFYPSDIAVE WESNGQPENN YKTTPPVLDS DGSFFLYSKL    180
TVDKSRWQQG NVFSCSVMHE ALHNHYTQKS LSLSPGK                             217

SEQ ID NO: 18           moltype = AA   length = 216
FEATURE                 Location/Qualifiers
source                  1..216
                        mol_type = protein
                        organism = synthetic construct
SEQUENCE: 18
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT    120
LPPSRDELTK NQVSLWCLVK GFYPSDIAVE WESNGQPENN YKTTPPVLDS DGSFFLYSKL    180
```

```
TVDKSRWQQG NVFSCSVMHE ALHNHYTQKS LSLSPG                          216

SEQ ID NO: 19            moltype = AA  length = 217
FEATURE                  Location/Qualifiers
source                   1..217
                         mol_type = protein
                         organism = synthetic construct
SEQUENCE: 19
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLWCLVK GFYPSDIAVE WESNGQPENN YKTTPPVLDS DGSFFLYSKL   180
TVDKSRWQQG NVFSCSVMHE ALHNHYTQKS LSLSPGK                           217

SEQ ID NO: 20            moltype = AA  length = 216
FEATURE                  Location/Qualifiers
source                   1..216
                         mol_type = protein
                         organism = synthetic construct
SEQUENCE: 20
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLWCLVK GFYPSDIAVE WESNGQPENN YKTTPPVLDS DGSFFLYSKL   180
TVDKSRWQQG NVFSCSVMHE ALHNHYTQKS LSLSPG                            216

SEQ ID NO: 21            moltype = AA  length = 227
FEATURE                  Location/Qualifiers
source                   1..227
                         mol_type = protein
                         organism = synthetic construct
SEQUENCE: 21
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                227

SEQ ID NO: 22            moltype = AA  length = 226
FEATURE                  Location/Qualifiers
source                   1..226
                         mol_type = protein
                         organism = synthetic construct
SEQUENCE: 22
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPG                 226

SEQ ID NO: 23            moltype = AA  length = 227
FEATURE                  Location/Qualifiers
source                   1..227
                         mol_type = protein
                         organism = synthetic construct
SEQUENCE: 23
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALSA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGK                227

SEQ ID NO: 24            moltype = AA  length = 226
FEATURE                  Location/Qualifiers
source                   1..226
                         mol_type = protein
                         organism = synthetic construct
SEQUENCE: 24
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALSA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPG                 226

SEQ ID NO: 25            moltype = AA  length = 227
FEATURE                  Location/Qualifiers
source                   1..227
                         mol_type = protein
                         organism = synthetic construct
SEQUENCE: 25
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPGK                227
```

```
SEQ ID NO: 26              moltype = AA  length = 226
FEATURE                    Location/Qualifiers
source                     1..226
                           mol_type = protein
                           organism = synthetic construct
SEQUENCE: 26
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 27              moltype = AA  length = 217
FEATURE                    Location/Qualifiers
source                     1..217
                           mol_type = protein
                           organism = synthetic construct
SEQUENCE: 27
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLTCLVK GFYPSDIAVE WESYGTEWAN YKTTPPVLDS DGSFFLYSKL   180
TVTKEEWQQG FVFSCSVMHE ALHNHYTQKS LSLSPGK                            217

SEQ ID NO: 28              moltype = AA  length = 216
FEATURE                    Location/Qualifiers
source                     1..216
                           mol_type = protein
                           organism = synthetic construct
SEQUENCE: 28
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLTCLVK GFYPSDIAVE WESYGTEWAN YKTTPPVLDS DGSFFLYSKL   180
TVTKEEWQQG FVFSCSVMHE ALHNHYTQKS LSLSPG                             216

SEQ ID NO: 29              moltype = AA  length = 217
FEATURE                    Location/Qualifiers
source                     1..217
                           mol_type = protein
                           organism = synthetic construct
SEQUENCE: 29
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLWCLVK GFYPSDIAVE WESYGTEWAN YKTTPPVLDS DGSFFLYSKL   180
TVTKEEWQQG FVFSCSVMHE ALHNHYTQKS LSLSPGK                            217

SEQ ID NO: 30              moltype = AA  length = 216
FEATURE                    Location/Qualifiers
source                     1..216
                           mol_type = protein
                           organism = synthetic construct
SEQUENCE: 30
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLWCLVK GFYPSDIAVE WESYGTEWAN YKTTPPVLDS DGSFFLYSKL   180
TVTKEEWQQG FVFSCSVMHE ALHNHYTQKS LSLSPG                             216

SEQ ID NO: 31              moltype = AA  length = 217
FEATURE                    Location/Qualifiers
source                     1..217
                           mol_type = protein
                           organism = synthetic construct
SEQUENCE: 31
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLWCLVK GFYPSDIAVE WESYGTEWAN YKTTPPVLDS DGSFFLYSKL   180
TVTKEEWQQG FVFSCSVMHE ALHNHYTQKS LSLSPGK                            217

SEQ ID NO: 32              moltype = AA  length = 216
FEATURE                    Location/Qualifiers
source                     1..216
                           mol_type = protein
                           organism = synthetic construct
SEQUENCE: 32
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLWCLVK GFYPSDIAVE WESYGTEWAN YKTTPPVLDS DGSFFLYSKL   180
TVTKEEWQQG FVFSCSVMHE ALHNHYTQKS LSLSPG                             216

SEQ ID NO: 33              moltype = AA  length = 217
FEATURE                    Location/Qualifiers
```

```
source                   1..217
                         mol_type = protein
                         organism = synthetic construct
SEQUENCE: 33
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALGA PIEKTISKAK GQPREPQVYT   120
LPPSRDELTK NQVSLWCLVK GFYPSDIAVE WESYGTEWAN YKTTPPVLDS DGSFFLYSKL   180
TVTKEEWQQG FVFSCSVMHE ALHNHYTQKS LSLSPGK                            217

SEQ ID NO: 34            moltype = AA   length = 216
FEATURE                  Location/Qualifiers
source                   1..216
                         mol_type = protein
                         organism = synthetic construct
SEQUENCE: 34
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALGA PIEKTISKAK GQPREPQVYT   120
LPPSRDELTK NQVSLWCLVK GFYPSDIAVE WESYGTEWAN YKTTPPVLDS DGSFFLYSKL   180
TVTKEEWQQG FVFSCSVMHE ALHNHYTQKS LSLSPG                             216

SEQ ID NO: 35            moltype = AA   length = 217
FEATURE                  Location/Qualifiers
source                   1..217
                         mol_type = protein
                         organism = synthetic construct
SEQUENCE: 35
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALSA PIEKTISKAK GQPREPQVYT   120
LPPSRDELTK NQVSLWCLVK GFYPSDIAVE WESYGTEWAN YKTTPPVLDS DGSFFLYSKL   180
TVTKEEWQQG FVFSCSVMHE ALHNHYTQKS LSLSPGK                            217

SEQ ID NO: 36            moltype = AA   length = 216
FEATURE                  Location/Qualifiers
source                   1..216
                         mol_type = protein
                         organism = synthetic construct
SEQUENCE: 36
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALSA PIEKTISKAK GQPREPQVYT   120
LPPSRDELTK NQVSLWCLVK GFYPSDIAVE WESYGTEWAN YKTTPPVLDS DGSFFLYSKL   180
TVTKEEWQQG FVFSCSVMHE ALHNHYTQKS LSLSPG                             216

SEQ ID NO: 37            moltype = AA   length = 217
FEATURE                  Location/Qualifiers
source                   1..217
                         mol_type = protein
                         organism = synthetic construct
SEQUENCE: 37
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLSCAVK GFYPSDIAVE WESYGTEWAN YKTTPPVLDS DGSFFLVSKL   180
TVTKEEWQQG FVFSCSVMHE ALHNHYTQKS LSLSPGK                            217

SEQ ID NO: 38            moltype = AA   length = 216
FEATURE                  Location/Qualifiers
source                   1..216
                         mol_type = protein
                         organism = synthetic construct
SEQUENCE: 38
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLSCAVK GFYPSDIAVE WESYGTEWAN YKTTPPVLDS DGSFFLVSKL   180
TVTKEEWQQG FVFSCSVMHE ALHNHYTQKS LSLSPG                             216

SEQ ID NO: 39            moltype = AA   length = 217
FEATURE                  Location/Qualifiers
source                   1..217
                         mol_type = protein
                         organism = synthetic construct
SEQUENCE: 39
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLSCAVK GFYPSDIAVE WESYGTEWAN YKTTPPVLDS DGSFFLVSKL   180
TVTKEEWQQG FVFSCSVMHE ALHNHYTQKS LSLSPGK                            217

SEQ ID NO: 40            moltype = AA   length = 216
FEATURE                  Location/Qualifiers
source                   1..216
                         mol_type = protein
```

```
                        organism = synthetic construct
SEQUENCE: 40
APEAAGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLSCAVK GFYPSDIAVE WESYGTEWAN YKTTPPVLDS DGSFFLVSKL   180
TVTKEEWQQG FVFSCSVMHE ALHNHYTQKS LSLSPG                             216

SEQ ID NO: 41           moltype = AA  length = 227
FEATURE                 Location/Qualifiers
source                  1..227
                        mol_type = protein
                        organism = synthetic construct
SEQUENCE: 41
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESYGTEWAN YKTTPPVLDS   180
DGSFFLYSKL TVTKEEWQQG FVFSCSVMHE ALHNHYTQKS LSLSPGK                 227

SEQ ID NO: 42           moltype = AA  length = 226
FEATURE                 Location/Qualifiers
source                  1..226
                        mol_type = protein
                        organism = synthetic construct
SEQUENCE: 42
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLWCLVK GFYPSDIAVE WESYGTEWAN YKTTPPVLDS   180
DGSFFLYSKL TVTKEEWQQG FVFSCSVMHE ALHNHYTQKS LSLSPG                  226

SEQ ID NO: 43           moltype = AA  length = 227
FEATURE                 Location/Qualifiers
source                  1..227
                        mol_type = protein
                        organism = synthetic construct
SEQUENCE: 43
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALSA PIEKTISKAK   120
GQPREPQVYT LPPSRDELTK NQVSLWCLVK GFYPSDIAVE WESYGTEWAN YKTTPPVLDS   180
DGSFFLYSKL TVTKEEWQQG FVFSCSVMHE ALHNHYTQKS LSLSPGK                 227

SEQ ID NO: 44           moltype = AA  length = 226
FEATURE                 Location/Qualifiers
source                  1..226
                        mol_type = protein
                        organism = synthetic construct
SEQUENCE: 44
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALSA PIEKTISKAK   120
GQPREPQVYT LPPSRDELTK NQVSLWCLVK GFYPSDIAVE WESYGTEWAN YKTTPPVLDS   180
DGSFFLYSKL TVTKEEWQQG FVFSCSVMHE ALHNHYTQKS LSLSPG                  226

SEQ ID NO: 45           moltype = AA  length = 952
FEATURE                 Location/Qualifiers
source                  1..952
                        mol_type = protein
                        organism = Homo sapiens
SEQUENCE: 45
MGVRHPPCSH RLLAVCALVS LATAALLGHI LLHDFLLVPR ELSGSSPVLE ETHPAHQQGA    60
SRPGPRDAQA HPGRPRAVPT QCDVPPNSRF DCAPDKAITQ EQCEARGCCY IPAKQGLQGA   120
QMGQPWCFFP PSYPSYKLEN LSSSEMGYTA TLTRTTPTFF PKDILTLRLD VMMETENRLH   180
FTIKDPANRR YEVPLETPHV HSRAPSPLYS VEFSEEPFGV IVRRQLDGRV LLNTTVAPLF   240
FADQFLQLST SLPSQYITGL AEHLSPLMLS TSWTRITLWN RDLAPTPGAN LYGSHPFYLA   300
LEDGGSAHGV FLLNSNAMDV VLQPSPALSW RSTGGILDVY IFLGPEPKSV VQQYLDVVGY   360
PFMPPYWGLG FHLCRWGYSS TAITRQVVEN MTRAHFPLDV QWNDLDYMDS RRDFTFNKDG   420
FRDFPAMVQE LHQGGRRYMM IVDPAISSSG PAGSYRPYDE GLRRGVFITN ETGQPLIGKV   480
WPGSTAFPDF TNPTALAWWE DMVAEFHDQV PFDGMWIDMN EPSNFIRGSE DGCPNNELEN   540
PPYVPGVVGG TLQAATICAS SHQFLSTHYN LHNLYGLTEA IASHRALVKA RGTRPFVISR   600
STFAGHGRYA GHWTGDVWSS WEQLASSVPE ILQFNLLGVP LVGADVCGFL GNTSEELCVR   660
WTQLGAFYPF MRNHNSLLSL PQEPYSFSEP AQQAMRKALT LRYALLPHLY TLFHQAHVAG   720
ETVARPLFLE FPKDSSTWTV DHQLLWGEAL LITPVLQAGK AEVTGYFPLG TWYDLQTVPV   780
EALGSLPPPP AAPREPAIHS EGQWVTLPAP LDTINVHLRA GYIIPLQPGG LTTTESRQQP   840
MALAVALTKG GEARGELFWD DGESLEVLER GAYTQVIFLA RNNTIVNELV RVTSEGAGLQ   900
LQKVTVLGVA TAPQQVLSNG VPVSNFTYSP DTKVLDICVS LLMGEQFLVS WC           952

SEQ ID NO: 46           moltype = AA  length = 925
FEATURE                 Location/Qualifiers
source                  1..925
                        mol_type = protein
                        organism = Homo sapiens
```

```
SEQUENCE: 46
GHILLHDFLL VPRELSGSSP VLEETHPAHQ QGASRPGPRD AQAHPGRPRA VPTQCDVPPN    60
SRFDCAPDKA ITQEQCEARG CCYIPAKQGL QGAQMGQPWC FFPPSYPSYK LENLSSSEMG   120
YTATLTRTTP TFFPKDILTL RLDVMMETEN RLHFTIKDPA NRRYEVPLET PHVHSRAPSP   180
LYSVEFSEEP FGVIVRRQLD GRVLLNTTVA PLFFADQFLQ LSTSLPSQYI TGLAEHLSPL   240
MLSTSWTRIT LWNRDLAPTP GANLYGSHPF YLALEDGGSA HGVFLLNSNA MDVVLQPSPA   300
LSWRSTGGIL DVYIFLGPEP KSVVQQYLDV VGYPFMPPYW GLGFHLCRWG YSSTAITRQV   360
VENMTRAHFP LDVQWNDLDY MDSRRDFTFN KDGFRDFPAM VQELHQGGRR YMMIVDPAIS   420
SSGPAGSYRP YDEGLRRGVF ITNETGQPLI GKVWPGSTAF PDFTNPTALA WWEDMVAEFH   480
DQVPFDGMWI DMNEPSNFIR GSEDGCPNNE LENPPYVPGV VGGTLQAATI CASSHQFLST   540
HYNLHNLYGL TEAIASHRAL VKARGTRPFV ISRSTFAGHG RYAGHWTGDV WSSWEQLASS   600
VPEILQFNLL GVPLVGADVC GFLGNTSEEL CVRWTQLGAF YPFMRNHNSL LSLPQEPYSF   660
SEPAQQAMRK ALTLRYALLP HLYTLFHQAH VAGETVARPL FLEFPKDSST WTVDHQLLWG   720
EALLITPVLQ AGKAEVTGYF PLGTWYDLQT VPVEALGSLP PPPAAPREPA IHSEGQWVTL   780
PAPLDTINVH LRAGYIIPLQ GPGLTTTESR QQPMALAVAL TKGGEARGEL FWDDGESLEV   840
LERGAYTQVI FLARNNTIVN ELVRVTSEGA GLQLQKVTVL GVATAPQQVL SNGVPVSNFT   900
YSPDTKVLDI CVSLLMGEQF LVSWC                                        925

SEQ ID NO: 47           moltype = AA  length = 883
FEATURE                 Location/Qualifiers
source                  1..883
                        mol_type = protein
                        organism = synthetic construct
SEQUENCE: 47
AHPGRPRAVP TQCDVPPNSR FDCAPDKAIT QEQCEARGCC YIPAKQGLQG AQMGQPWCFF    60
PPSYPSYKLE NLSSSEMGYT ATLTRTTPTF FPKDILTLRL DVMMETENRL HFTIKDPANR   120
RYEVPLETPH VHSRAPSPLY SVEFSEEPFG VIVRRQLDGR VLLNTTVAPL FFADQFLQLS   180
TSLPSQYITG LAEHLSPLML STSWTRITLW NRDLAPTPGA NLYGSHPFYL ALEDGGSAHG   240
VFLLNSNAMD VVLQPSPALS WRSTGGILDV YIFLGPEPKS VVQQYLDVVG YPFMPPYWGL   300
GFPHLCRWGYS STAITRQVVE NMTRAHFPLD VQWNDLDYMD SRRDFTFNKD GFRDFPAMVQ   360
ELHQGGRRYM MIVDPAISSS GPAGSYRPYD EGLRRGVFIT NETGQPLIGK VWPGSTAFPD   420
FTNPTALAWW EDMVAEFHDQ VPFDGMWIDM NEPSNFIRGS EDGCPNNELE NPPYVPGVVG   480
GTLQAATICA SSHQFLSTHY NLHNLYGLTE AIASHRALVK ARGTRPFVIS RSTFAGHGRY   540
AGHWTGDVWS SWEQLASSVP EILQFNLLGV PLVGADVCGF LGNTSEELCV RWTQLGAFYP   600
FMRNHNSLLS LPQEPYSFSE PAQQAMRKAL TLRYALLPHL YTLFHQAHVA GETVARPLFL   660
EFPKDSSTWT VDHQLLWGEA LLITPVLQAG KAEVTGYFPL GTWYDLQTVP VEALGSLPPP   720
PAAPREPAIH SEGQWVTLPA PLDTINVHLR AGYIIPLQGP GLTTTESRQQ PMALAVALTK   780
GGEARGELFW DDGESLEVLE RGAYTQVIFL ARNNTIVNEL VRVTSEGAGL QLQKVTVLGV   840
ATAPQQVLSN GVPVSNFTYS PDTKVLDICV SLLMGEQFLV SWC                    883

SEQ ID NO: 48           moltype = AA  length = 1157
FEATURE                 Location/Qualifiers
source                  1..1157
                        mol_type = protein
                        organism = synthetic construct
SEQUENCE: 48
GHILLHDFLL VPRELSGSSP VLEETHPAHQ QGASRPGPRD AQAHPGRPRA VPTQCDVPPN    60
SRFDCAPDKA ITQEQCEARG CCYIPAKQGL QGAQMGQPWC FFPPSYPSYK LENLSSSEMG   120
YTATLTRTTP TFFPKDILTL RLDVMMETEN RLHFTIKDPA NRRYEVPLET PHVHSRAPSP   180
LYSVEFSEEP FGVIVRRQLD GRVLLNTTVA PLFFADQFLQ LSTSLPSQYI TGLAEHLSPL   240
MLSTSWTRIT LWNRDLAPTP GANLYGSHPF YLALEDGGSA HGVFLLNSNA MDVVLQPSPA   300
LSWRSTGGIL DVYIFLGPEP KSVVQQYLDV VGYPFMPPYW GLGFHLCRWG YSSTAITRQV   360
VENMTRAHFP LDVQWNDLDY MDSRRDFTFN KDGFRDFPAM VQELHQGGRR YMMIVDPAIS   420
SSGPAGSYRP YDEGLRRGVF ITNETGQPLI GKVWPGSTAF PDFTNPTALA WWEDMVAEFH   480
DQVPFDGMWI DMNEPSNFIR GSEDGCPNNE LENPPYVPGV VGGTLQAATI CASSHQFLST   540
HYNLHNLYGL TEAIASHRAL VKARGTRPFV ISRSTFAGHG RYAGHWTGDV WSSWEQLASS   600
VPEILQFNLL GVPLVGADVC GFLGNTSEEL CVRWTQLGAF YPFMRNHNSL LSLPQEPYSF   660
SEPAQQAMRK ALTLRYALLP HLYTLFHQAH VAGETVARPL FLEFPKDSST WTVDHQLLWG   720
EALLITPVLQ AGKAEVTGYF PLGTWYDLQT VPVEALGSLP PPPAAPREPA IHSEGQWVTL   780
PAPLDTINVH LRAGYIIPLQ GPGLTTTESR QQPMALAVAL TKGGEARGEL FWDDGESLEV   840
LERGAYTQVI FLARNNTIVN ELVRVTSEGA GLQLQKVTVL GVATAPQQVL SNGVPVSNFT   900
YSPDTKVLDI CVSLLMGEQF LVSWCGGGS DKTHTCPPCP APEAAGGPSV FLFPPKPKDT   960
LMISRTPEVT CVVVDVSHED PEEVKFNWYVD GVEVHNAKTK PREEQYNSTY RVVSVLTVLH  1020
QDWLNGKEYK CKVSNKALPA PIEKTISKAK GQPREPQVYT LPPSRDELTK NQVSLSCAVK  1080
GFYPSDIAVE WESNGQPENN YKTTPPVLDS DGSFFLVSKL TVDKSRWQQG NVFSCSVMHE  1140
ALHNHYTQKS LSLSPGK                                                1157

SEQ ID NO: 49           moltype = AA  length = 1156
FEATURE                 Location/Qualifiers
source                  1..1156
                        mol_type = protein
                        organism = synthetic construct
SEQUENCE: 49
GHILLHDFLL VPRELSGSSP VLEETHPAHQ QGASRPGPRD AQAHPGRPRA VPTQCDVPPN    60
SRFDCAPDKA ITQEQCEARG CCYIPAKQGL QGAQMGQPWC FFPPSYPSYK LENLSSSEMG   120
YTATLTRTTP TFFPKDILTL RLDVMMETEN RLHFTIKDPA NRRYEVPLET PHVHSRAPSP   180
LYSVEFSEEP FGVIVRRQLD GRVLLNTTVA PLFFADQFLQ LSTSLPSQYI TGLAEHLSPL   240
MLSTSWTRIT LWNRDLAPTP GANLYGSHPF YLALEDGGSA HGVFLLNSNA MDVVLQPSPA   300
LSWRSTGGIL DVYIFLGPEP KSVVQQYLDV VGYPFMPPYW GLGFHLCRWG YSSTAITRQV   360
```

```
VENMTRAHFP LDVQWNDLDY MDSRRDFTFN KDGFRDFPAM VQELHQGGRR YMMIVDPAIS    420
SSGPAGSYRP YDEGLRRGVF ITNETGQPLI GKVWPGSTAF PDFTNPTALA WWEDMVAEFH    480
DQVPFDGMWI DMNEPSNFIR GSEDGCPNNE LENPPYVPGV VGGTLQAATI CASSHQFLST    540
HYNLHNLYGL TEAIASHRAL VKARGTRPFV ISRSTFAGHG RYAGHWTGDV WSSWEQLASS    600
VPEILQFNLL GVPLVGADVC GFLGNTSEEL CVRWTQLGAF YPFMRNHNSL LSLPQEPYSF    660
SEPAQQAMRK ALTLRYALLP HLYTLFHQAH VAGETVARPL FLEFPKDSST WTVDHQLLWG    720
EALLITPVLQ AGKAEVTGYF PLGTWYDLQT VPVEALGSLP PPPAAPREPA IHSEGQWVTL    780
PAPLDTINVH LRAGYIIPLQ GPGLTTTESR QQPMALAVAL TKGGEARGEL FWDDGESLEV    840
LERGAYTQVI FLARNNTIVN ELVRVTSEGA GLQLQKVTVL GVATAPQQVL SNGVPVSNFT    900
YSPDTKVLDI CVSLLMGEQF LVSWCGGGGS DKTHTCPPCP APEAAGGPSV FLFPPKPKDT    960
LMISRTPEVT CVVVDVSHED PEVKFNWYVD GVEVHNAKTK PREEQYNSTY RVVSVLTVLH   1020
QDWLNGKEYK CKVSNKALPA PIEKTISKAK GQPREPQVYT LPPSRDELTK NQVSLSCAVK   1080
GFYPSDIAVE WESNGQPENN YKTTPPVLDS DGSFFLVSKL TVDKSRWQQG NVFSCSVMHE   1140
ALHNHYTQKS LSLSPG                                                  1156

SEQ ID NO: 50           moltype = AA  length = 1115
FEATURE                 Location/Qualifiers
source                  1..1115
                        mol_type = protein
                        organism = synthetic construct
SEQUENCE: 50
AHPGRPRAVP TQCDVPPNSR FDCAPDKAIT QEQCEARGCC YIPAKQGLQG AQMGQPWCFF     60
PPSYPSYKLE NLSSSEMGYT ATLTRTTPTF FPKDILTLRL DVMMETENRL HFTIKDPANR    120
RYEVPLETPH VHSRAPSPLY SVEFSEEPFG VIVRRQLDGR VLLNTTVAPL FFADQFLQLS    180
TSLPSQYITG LAEHLSPLML STSWTRITLW NRDLAPTPGA NLYGSHPFYL ALEDGGSAHG    240
VFLLNSNAMD VVLQPSPALS WRSTGGILDV YIFLGPEPKS VVQQYLDVVG YPFMPPYWGL    300
GFHLCRWGYS STAITRQVVE NMTRAHPLD VQWNDLDYMD SRRDFTFNKD GFRDFPAMVQ    360
ELHQGGRRYM MIVDPAISSS GPAGSYRPYD EGLRRGVFIT NETGQPLIGK VWPGSTAFPD    420
FTNPTALAWW EDMVAEFHDQ VPFDGMWIDM NEPSNFIRGS EDGCPNNELE NPPYVPGVVG    480
GTLQAATICA SSHQFLSTHY NLHNLYGLTE AIASHRALVK ARGTRPFVIS RSTFAGHGRY    540
AGHWTGDVWS SWEQLASSVP EILQFNLLGV PLVGADVCGF LGNTSEELCV RWTQLGAFYP    600
FMRNHNSLLS LPQEPYSFSE PAQQAMRKAL TLRYALLPHL YTLFHQAHVA GETVARPLFL    660
EFPKDSSTWT VDHQLLWGEA LLITPVLQAG KAEVTGYFPL GTWYDLQTVP VEALGSLPPP    720
PAAPREPAIH SEGQWVTLPA PLDTINVHLR AGYIIPLQGP GLTTTESRQQ PMALAVALTK    780
GGEARGELFW DDGESLEVLE RGAYTQVIFL ARNNTIVNEL VRVTSEGAGL QLQKVTVLGV    840
ATAPQQVLSN GVPVSNFTYS PDTKVLDICV SLLMGEQFLV SWCGGGGSDK THTCPPCPAP    900
EAAGGPSVFL FPPKPKDTLM ISRTPEVTCV VVDVSHEDPE VKFNWYVDGV EVHNAKTKPR    960
EEQYNSTYRV VSVLTVLHQD WLNGKEYKCK VSNKALPAPI EKTISKAKGQ PREPQVYTLP   1020
PSRDELTKNQ VSLSCAVKGF YPSDIAVEWE SNGQPENNYK TTPPVLDSDG SFFLVSKLTV   1080
DKSRWQQGNV FSCSVMHEAL HNHYTQKSLS LSPGK                             1115

SEQ ID NO: 51           moltype = AA  length = 1114
FEATURE                 Location/Qualifiers
source                  1..1114
                        mol_type = protein
                        organism = synthetic construct
SEQUENCE: 51
AHPGRPRAVP TQCDVPPNSR FDCAPDKAIT QEQCEARGCC YIPAKQGLQG AQMGQPWCFF     60
PPSYPSYKLE NLSSSEMGYT ATLTRTTPTF FPKDILTLRL DVMMETENRL HFTIKDPANR    120
RYEVPLETPH VHSRAPSPLY SVEFSEEPFG VIVRRQLDGR VLLNTTVAPL FFADQFLQLS    180
TSLPSQYITG LAEHLSPLML STSWTRITLW NRDLAPTPGA NLYGSHPFYL ALEDGGSAHG    240
VFLLNSNAMD VVLQPSPALS WRSTGGILDV YIFLGPEPKS VVQQYLDVVG YPFMPPYWGL    300
GFHLCRWGYS STAITRQVVE NMTRAHPLD VQWNDLDYMD SRRDFTFNKD GFRDFPAMVQ    360
ELHQGGRRYM MIVDPAISSS GPAGSYRPYD EGLRRGVFIT NETGQPLIGK VWPGSTAFPD    420
FTNPTALAWW EDMVAEFHDQ VPFDGMWIDM NEPSNFIRGS EDGCPNNELE NPPYVPGVVG    480
GTLQAATICA SSHQFLSTHY NLHNLYGLTE AIASHRALVK ARGTRPFVIS RSTFAGHGRY    540
AGHWTGDVWS SWEQLASSVP EILQFNLLGV PLVGADVCGF LGNTSEELCV RWTQLGAFYP    600
FMRNHNSLLS LPQEPYSFSE PAQQAMRKAL TLRYALLPHL YTLFHQAHVA GETVARPLFL    660
EFPKDSSTWT VDHQLLWGEA LLITPVLQAG KAEVTGYFPL GTWYDLQTVP VEALGSLPPP    720
PAAPREPAIH SEGQWVTLPA PLDTINVHLR AGYIIPLQGP GLTTTESRQQ PMALAVALTK    780
GGEARGELFW DDGESLEVLE RGAYTQVIFL ARNNTIVNEL VRVTSEGAGL QLQKVTVLGV    840
ATAPQQVLSN GVPVSNFTYS PDTKVLDICV SLLMGEQFLV SWCGGGGSDK THTCPPCPAP    900
EAAGGPSVFL FPPKPKDTLM ISRTPEVTCV VVDVSHEDPE VKFNWYVDGV EVHNAKTKPR    960
EEQYNSTYRV VSVLTVLHQD WLNGKEYKCK VSNKALPAPI EKTISKAKGQ PREPQVYTLP   1020
PSRDELTKNQ VSLSCAVKGF YPSDIAVEWE SNGQPENNYK TTPPVLDSDG SFFLVSKLTV   1080
DKSRWQQGNV FSCSVMHEAL HNHYTQKSLS LSPG                              1114

SEQ ID NO: 52           moltype = AA  length = 1157
FEATURE                 Location/Qualifiers
source                  1..1157
                        mol_type = protein
                        organism = synthetic construct
SEQUENCE: 52
GHILLHDFLL VPRELSGSSP VLEETHPAHQ QGASRPGPRD AQAHPGRPRA VPTQCDVPPN     60
SRFDCAPDKA ITQEQCEARG CCYIPAKQGL QGAMGQPWC FFPPSYPSYK LENLSSSEMG    120
YTATLTRTTP TFFPKDILTL RLDVMMETEN RLHFTIKDPA NRRYEVPLET PHVHSRAPSP    180
LYSVEFSEEP FGVIVRRQLD GRVLLNTTVA PLFFADQFLQ LSTSLPSQYI TGLAEHLSPL    240
MLSTSWTRIT LWNRDLAPTP GANLYGSHPF YLALEDGGSA HGVFLLNSNA MDVVLQPSPA    300
LSWRSTGGIL DVYIFLGPEP KSVVQQYLDV VGYPFMPPYW GLGFHLCRWG YSSTAITRQV    360
```

```
VENMTRAHFP LDVQWNDLDY MDSRRDFTFN KDGFRDFPAM VQELHQGGRR YMMIVDPAIS    420
SSGPAGSYRP YDEGLRRGVF ITNETGQPLI GKVWPGSTAF PDFTNPTALA WWEDMVAEFH    480
DQVPFDGMWI DMNEPSNFIR GSEDGCPNNE LENPPYVPGV VGGTLQAATI CASSHQFLST    540
HYNLHNLYGL TEAIASHRAL VKARGTRPFV ISRSTFAGHG RYAGHWTGDV WSSWEQLASS    600
VPEILQFNLL GVPLVGADVC GFLGNTSEEL CVRWTQLGAF YPPMRNHNSL LSLPQEPYSF    660
SEPAQQAMRK ALTLRYALLP HLYTLFHQAH VAGETVARPL FLEFPKDSST WTVDHQLLWG    720
EALLITPVLQ AGKAEVTGYF PLGTWYDLQT VPVEALGSLP PPPAAPREPA IHSEGQWVTL    780
PAPLDTINVH LRAGYIIPLQ GPGLTTTESR QQPMALAVAL TKGGEARGEL FWDDGESLEV    840
LERGAYTQVI FLARNNTIVN ELVRVTSEGA GLQLQKVTVL GVATAPQQVL SNGVPVSNFT    900
YSPDTKVLDI CVSLLMGEQF LVSWCGGGGS DKTHTCPPCP APEAAGGPSV FLFPPKPKDT    960
LMISRTPEVT CVVVDVSHED PEVKFNWYVD GVEVHNAKTK PREEQYNSTY RVVSVLTVLH   1020
QDWLNGKEYK CKVSNKALSA PIEKTISKAK GQPREPQVYT LPPSRDELTK NQVSLSCAVK   1080
GFYPSDIAVE WESNGQPENN YKTTPPVLDS DGSFFLVSKL TVDKSRWQQG NVFSCSVMHE   1140
ALHNHYTQKS LSLSPGK                                                  1157

SEQ ID NO: 53           moltype = AA   length = 1156
FEATURE                 Location/Qualifiers
source                  1..1156
                        mol_type = protein
                        organism = synthetic construct
SEQUENCE: 53
GHILLHDFLL VPRELSGSSP VLEETHPAHQ QGASRPGPRD AQAHPGRPRA VPTQCDVPPN     60
SRFDCAPDKA ITQEQCEARG CCYIPAKQGL QGAQMGQPWC FFPPSYPSYK LENLSSSEMG    120
YTATLTRTTP TFFPKDILTL RLDVMMETEN RLHFTIKDPA NRRYEVPLET PHVHSRAPSP    180
LYSVEFSEEP FGVIVRRQLD GRVLLNTTVA PLFFADQFLQ LSTSLPSQYI TGLAEHLSPL    240
MLSTSWTRIT LWNRDLAPTP GANLYGSHPF YLALEDGGSA HGVFLLNSNA MDVVLQPSPA    300
LSWRSTGGIL DVYIFLGPEP KSVVQQYLDV VGYPFMPPYW GLGFHLCRWG YSSTAITRQV    360
VENMTRAHFP LDVQWNDLDY MDSRRDFTFN KDGFRDFPAM VQELHQGGRR YMMIVDPAIS    420
SSGPAGSYRP YDEGLRRGVF ITNETGQPLI GKVWPGSTAF PDFTNPTALA WWEDMVAEFH    480
DQVPFDGMWI DMNEPSNFIR GSEDGCPNNE LENPPYVPGV VGGTLQAATI CASSHQFLST    540
HYNLHNLYGL TEAIASHRAL VKARGTRPFV ISRSTFAGHG RYAGHWTGDV WSSWEQLASS    600
VPEILQFNLL GVPLVGADVC GFLGNTSEEL CVRWTQLGAF YPPMRNHNSL LSLPQEPYSF    660
SEPAQQAMRK ALTLRYALLP HLYTLFHQAH VAGETVARPL FLEFPKDSST WTVDHQLLWG    720
EALLITPVLQ AGKAEVTGYF PLGTWYDLQT VPVEALGSLP PPPAAPREPA IHSEGQWVTL    780
PAPLDTINVH LRAGYIIPLQ GPGLTTTESR QQPMALAVAL TKGGEARGEL FWDDGESLEV    840
LERGAYTQVI FLARNNTIVN ELVRVTSEGA GLQLQKVTVL GVATAPQQVL SNGVPVSNFT    900
YSPDTKVLDI CVSLLMGEQF LVSWCGGGGS DKTHTCPPCP APEAAGGPSV FLFPPKPKDT    960
LMISRTPEVT CVVVDVSHED PEVKFNWYVD GVEVHNAKTK PREEQYNSTY RVVSVLTVLH   1020
QDWLNGKEYK CKVSNKALSA PIEKTISKAK GQPREPQVYT LPPSRDELTK NQVSLSCAVK   1080
GFYPSDIAVE WESNGQPENN YKTTPPVLDS DGSFFLVSKL TVDKSRWQQG NVFSCSVMHE   1140
ALHNHYTQKS LSLSPG                                                   1156

SEQ ID NO: 54           moltype = AA   length = 1115
FEATURE                 Location/Qualifiers
source                  1..1115
                        mol_type = protein
                        organism = synthetic construct
SEQUENCE: 54
AHPGRPRAVP TQCDVPPNSR FDCAPDKAIT QEQCEARGCC YIPAKQGLQG AQMGQPWCFF     60
PPSYPSYKLE NLSSSEMGYT ATLTRTTPTF FPKDILTLRL DVMMETENRL HFTIKDPANR    120
RYEVPLETPH VHSRAPSPLY SVEFSEEPFG VIVRRQLDGR VLLNTTVAPL FFADQFLQLS    180
TSLPSQYITG LAEHLSPLML STSWTRITLW NRDLAPTPGA NLYGSHPFYL ALEDGGSAHG    240
VFLLNSNAMD VVLQPSPALS WRSTGGILDV YIFLGPEPKS VVQQYLDVVG YPFMPPYWGL    300
GFHLCRWGYS STAITRQVVE NMTRAHFPLD VQWNDLDYMD SRRDFTFNKD GFRDFPAMVQ    360
ELHQGGRRYM MIVDPAISSS GPAGSYRPYD EGLRRGVFIT NETGQPLIGK VWPGSTAFPD    420
FTNPTALAWW EDMVAEFHDQ VPFDGMWIDM NEPSNFIRGS EDGCPNNELE NPPYVPGVVG    480
GTLQAATICA SSHQFLSTHY NLHNLYGLTE AIASHRALVK ARGTRPFVIS RSTFAGHGRY    540
AGHWTGDVWS SWEQLASSVP EILQFNLLGV PLVGADVCGF LGNTSEELCV RWTQLGAFYP    600
FMRNHNSLLS LPQEPYSFSE PAQQAMRKAL TLRYALLPHL YTLFHQAHVA GETVARPLFL    660
EFPKDSSTWT VDHQLLWGEA LLITPVLQAG KAEVTGYFPL GTWYDLQTVP VEALGSLPPP    720
PAAPREPAIH SEGQWVTLPA PLDTINVHLR AGYIIPLQGP GLTTTESRQQ PMALAVALTK    780
GGEARGELFW DDGESLEVLE RGAYTQVIFL ARNNTIVNEL VRVTSEGAGL QLQKVTVLGV    840
ATAPQQVLSN GVPVSNFTYS PDTKVLDICV SLLMGEQFLV SWCGGGGSDK THTCPPCPAP    900
EAAGGPSVFL FPPKPKDTLM ISRTPEVTCV VVDVSHEDPE VKFNWYVDGV EVHNAKTKPR    960
EEQYNSTYRV VSVLTVLHQD WLNGKEYKCK VSNKALSAPI EKTISKAKGQ PREPQVYTLP   1020
PSRDELTKNQ VSLSCAVKGF YPSDIAVEWE SNGQPENNYK TTPPVLDSDG SFFLVSKLTV   1080
DKSRWQQGNV FSCSVMHEAL HNHYTQKSLS LSPGK                              1115

SEQ ID NO: 55           moltype = AA   length = 1114
FEATURE                 Location/Qualifiers
source                  1..1114
                        mol_type = protein
                        organism = synthetic construct
SEQUENCE: 55
AHPGRPRAVP TQCDVPPNSR FDCAPDKAIT QEQCEARGCC YIPAKQGLQG AQMGQPWCFF     60
PPSYPSYKLE NLSSSEMGYT ATLTRTTPTF FPKDILTLRL DVMMETENRL HFTIKDPANR    120
RYEVPLETPH VHSRAPSPLY SVEFSEEPFG VIVRRQLDGR VLLNTTVAPL FFADQFLQLS    180
TSLPSQYITG LAEHLSPLML STSWTRITLW NRDLAPTPGA NLYGSHPFYL ALEDGGSAHG    240
VFLLNSNAMD VVLQPSPALS WRSTGGILDV YIFLGPEPKS VVQQYLDVVG YPFMPPYWGL    300
```

```
GFHLCRWGYS STAITRQVVE NMTRAHFPLD VQWNDLDYMD SRRDFTFNKD GFRDFPAMVQ    360
ELHQGGRRYM MIVDPAISSS GPAGSYRPYD EGLRRGVFIT NETGQPLIGK VWPGSTAFPD    420
FTNPTALAWW EDMVAEFHDQ VPFDGMWIDM NEPSNFIRGS EDGCPNNELE NPPYVPGVVG    480
GTLQAATICA SSHQFLSTHY NLHNLYGLTE AIASHRALVK ARGTRPFVIS RSTFAGHGRY    540
AGHWTGDVWS SWEQLASSVP EILQFNLLGV PLVGADVCGF LGNTSEELCV RWTQLGAFYP    600
FMRNHNSLLS LPQEPYSFSE PAQQAMRKAL TLRYALLPHL YTLFHQAHVA GETVARPLFL    660
EPPKDSSTWT VDHQLLWGEA LLITPVLQAG KAEVTGYFPL GTWYDLQTVP VEALGSLPPP    720
PAAPREPAIH SEGQWVTLPA PLDTINVHLR AGYIIPLQGP GLTTTESRQQ PMALAVALTK    780
GGEARGELFW DDGESLEVLE RGAYTQVIFL ARNNTIVNEL VRVTSEGAGL QLQKVTVLGV    840
ATAPQQVLSN GVPVSNFTYS PDTKVLDICV SLLMGEQFLV SWCGGGGSDK THTCPPCPAP    900
EAAGGPSVFL FPPKPKDTLM ISRTPEVTCV VVDVSHEDPE VKFNWYVDGV EVHNAKTKPR    960
EEQYNSTYRV VSVLTVLHQD WLNGKEYKCK VSNKALSAPI EKTISKAKGQ PREPQVYTLP   1020
PSRDELTKNQ VSLSCAVKGF YPSDIAVEWE SNGQPENNYK TTPPVLDSDG SFFLVSKLTV   1080
DKSRWQQGNV FSCSVMHEAL HNHYTQKSLS LSPG                               1114

SEQ ID NO: 56           moltype = AA  length = 1157
FEATURE                 Location/Qualifiers
source                  1..1157
                        mol_type = protein
                        organism = synthetic construct
SEQUENCE: 56
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLSCAVK GFYPSDIAVE WESNGQPENN YKTTPPVLDS    180
DGSFFLVSKL TVDKSRWQQG NVFSCSVMHE ALHNHYTQKS LSLSPGKGGG GSGHILLHDF    240
LLVPRELSGS SPVLEETHPA HQQGASRPGP RDAQAHPGRP RAVPTQCDVP PNSRFDCAPD    300
KAITQEQCEA RGCCYIPAKQ GLQGAQMGQP WCFFPPSYPS YKLENLSSSE MGYTATLTRT    360
TPTFFPKDIL TLRLDVMMET ENRLHFTIKD PANRRYEVPL ETPHVHSRAP SPLYSVEFSE    420
EPFGVIVRRQ LDGRVLLNTT VAPLFFADQF LQLSTSLPSQ YITGLAEHLS PLMLSTSWTR    480
ITLWNRDLAP TPGANLYGSH PFYLALEDGG SAHGVFLLNS NAMDVVLQPS PALSWRSTGG    540
ILDVYIFLGP EPKSVVQQYL DVVGYPFMPP YWGLGFHLCR WGYSSTAITR QVVENMTRAH    600
FPLDVQWNDL DYMDSRRDFT FNKDGFRDFP AMVQELHQGG RRYMMIVDPA ISSSGPAGSY    660
RPYDEGLRRG VFITNETGQP LIGKVWPGST AFPDFTNPTA LAWWEDMVAE FHDQVPFDGM    720
WIDMNEPSNF IRGSEDGCPN NELENPPYVP GVVGGTLQAA TICASSHQFL STHYNLHNLY    780
GLTEAIASHR ALVKARGTRP FVISRSTFAG HGRYAGHWTG DVWSSWEQLA SSVPEILQFN    840
LLGVPLVGAD VCGFLGNTSE ELCVRWTQLG AFYPFMRNHN SLLSLPQEPY SFSEPAQQAM    900
RKALTLRYAL LPHYTLFHQ AHVAGETVAR PLFLEFPKDS STWTVDHQLL WGEALLITPV    960
LQAGKAEVTG YFPLGTWYDL QTVPVEALGS LPPPPAAPRE PAIHSEGQWV TLPAPLDTIN   1020
VHLRAGYIIP LQGPGLTTTE SRQQPMALAV ALTKGGEARG ELFWDDGESL EVLERGAYTQ   1080
VIFLARNNTI VNELVRVTSE GAGLQLQKVT VLGVATAPQQ VLSNGVPVSN FTYSPDTKVL   1140
DICVSLLMGE QFLVSWC                                                  1157

SEQ ID NO: 57           moltype = AA  length = 1115
FEATURE                 Location/Qualifiers
source                  1..1115
                        mol_type = protein
                        organism = synthetic construct
SEQUENCE: 57
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLSCAVK GFYPSDIAVE WESNGQPENN YKTTPPVLDS    180
DGSFFLVSKL TVDKSRWQQG NVFSCSVMHE ALHNHYTQKS LSLSPGKGGG GSAHPGRPRA    240
VPTQCDVPPN SRFDCAPDKA ITQEQCEARG CCYIPAKQGL QGAQMGQPWC FFPPSYPSYK    300
LENLSSSEMG YTATLTRTTP TFFPKDILTL RLDVMMETEN RLHFTIKDPA NRRYEVPLET    360
PHVHSRAPSP LYSVEFSEEP FGVIVRRQLD GRVLLNTTVA PLFFADQFLQ LSTSLPSQYI    420
TGLAEHLSPL MLSTSWTRIT LWNRDLAPTP GANLYGSHPF YLALEDGGSA HGVFLLNSNA    480
MDVVLQPSPA LSWRSTGGIL DVYIFLGPEP KSVVQQYLDV VGYPFMPPYW GLGFHLCRWG    540
YSSTAITRQV VENMTRAHFP LDVQWNDLDY MDSRRDFTFN KDGFRDFPAM VQELHQGGRR    600
YMMIVDPAIS SSGPAGSYRP YDEGLRRGVF ITNETGQPLI GKVWPGSTAF PDFTNPTALA    660
WWEDMVAEFH DQVPFDGMWI DMNEPSNFIR GSEDGCPNNE LENPPYVPGV VGGTLQAATI    720
CASSHQFLST HYNLHNLYGL TEAIASHRAL VKARGTRPFV ISRSTFAGHG RYAGHWTGDV    780
WSSWEQLASS VPEILQFNLL GVPLVGADVC GFLGNTSEEL CVRWTQLGAF YPFMRNHNSL    840
LSLPQEPYSF SEPAQQAMRK ALTLRYALLP HLYTLFHQAH VAGETVARPL FLEFPKDSST    900
WTVDHQLLWG EALLITPVLQ AGKAEVTGYF PLGTWYDLQT VPVEALGSLP PPPAAPREPA    960
IHSEGQWVTL PAPLDTINVH LRAGYIIPLQ GPGLTTTESR QQPMALAVAL TKGGEARGEL   1020
FWDDGESLEV LERGAYTQVI FLARNNTIVN ELVRVTSEGA GLQLQKVTVL GVATAPQQVL   1080
SNGVPVSNFT YSPDTKVLDI CVSLLMGEQF LVSWC                              1115

SEQ ID NO: 58           moltype = AA  length = 1157
FEATURE                 Location/Qualifiers
source                  1..1157
                        mol_type = protein
                        organism = synthetic construct
SEQUENCE: 58
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALSA PIEKTISKAK    120
GQPREPQVYT LPPSRDELTK NQVSLSCAVK GFYPSDIAVE WESNGQPENN YKTTPPVLDS    180
DGSFFLVSKL TVDKSRWQQG NVFSCSVMHE ALHNHYTQKS LSLSPGKGGG GSGHILLHDF    240
LLVPRELSGS SPVLEETHPA HQQGASRPGP RDAQAHPGRP RAVPTQCDVP PNSRFDCAPD    300
```

```
KAITQEQCEA RGCCYIPAKQ GLQGAQMGQP WCFFPPSYPS YKLENLSSSE MGYTATLTRT    360
TPTFFPKDIL TLRLDVMMET ENRLHFTIKD PANRRYEVPL ETPHVHSRAP SPLYSVEFSE    420
EPFGVIVRRQ LDGRVLLNTT VAPLFFADQF LQLSTSLPSQ YITGLAEHLS PLMLSTSWTR    480
ITLWNRDLAP TPGANLYGSH PFYLALEDGG SAHGVFLLNS NAMDVVLQPS PALSWRSTGG    540
ILDVYIFLGP EPKSVVQQYL DVVGYPFMPP YWGLGFHLCR WGYSSTAITR QVVENMTRAH    600
FPLDVQWNDL DYMDSRRDFT FNKDGFRDFP AMVQELHQGG RRYMMIVDPA ISSSGPAGSY    660
RPYDEGLRRG VFITNETGQP LIGKVWPGST AFPDFTNPTA LAWWEDMVAE FHDQVPFDGM    720
WIDMNEPSNF IRGSEDGCPN NELENPPYVP GVVGGTLQAA TICASSHQFL STHYNLHNLY    780
GLTEAIASHR ALVKARGTRP FVISRSTFAG HGRYAGHWTG DVWSSWEQLA SSVPEILQFN    840
LLGVPLVGAD VCGFLGNTSE ELCVRWTQLG AFYPFMRNHN SLLSLPQEPY SFSEPAQQAM    900
RKALTLRYAL LPHLYTLFHQ AHVAGETVAR PLFLEFPKDS STWTVDHQLL WGEALLITPV    960
LQAGKAEVTG YFPLGTWYDL QTVPVEALGS LPPPPAAPRE PAIHSEGQWV TLPAPLDTIN   1020
VHLRAGYIIP LQGPGLTTTE SRQQPMALAV ALTKGGEARG ELFWDDGESL EVLERGAYTQ   1080
VIFLARNNTI VNELVRVTSE GAGLQLQKVT VLGVATAPQQ VLSNGVPVSN FTYSPDTKVL   1140
DICVSLLMGE QFLVSWC                                                  1157

SEQ ID NO: 59          moltype = AA  length = 1115
FEATURE                Location/Qualifiers
source                 1..1115
                       mol_type = protein
                       organism = synthetic construct
SEQUENCE: 59
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALSA PIEKTISKAK    120
GQPREPQVYT LPPSRDELTK NQVSLSCAVK GFYPSDIAVE WESNGQPENN YKTTPPVLDS    180
DGSFFLVSKL TVDKSRWQQG NVFSCSVMHE ALHNHYTQKS LSLSPGKGGG GSAHPGRPRA    240
VPTQCDVPPN SRFDCAPDKA ITQEQCEARG CCYIPAKQGL QGAQMGQPWC FFPSYPSYK     300
LENLSSSEMG YTATLTRTTP TFFPKDILTL RLDVMMETEN RLHFTIKDPA NRRYEVPLET    360
PHVHSRAPSP LYSVEFSEEP FGVIVRRQLD GRVLLNTTVA PLFFADQFLQ LSTSLPSQYI    420
TGLAEHLSPL MLSTSWTRIT LWNRDLAPTP GANLYGSHPF YLALEDGGSA HGVFLLNSNA    480
MDVVLQPSPA LSWRSTGGIL DVYIFLGPEP KSVVQQYLDV VGYPFMPPYW GLGFHLCRWG    540
YSSTAITRQV VENMTRAHFP LDVQWNDLDY MDSRRDFTFN KDGFRDFPAM VQELHQGGRR    600
YMMIVDPAIS SSGPAGSYRP YDEGLRRGVF ITNETGQPLI GKVWPGSTAF PDFTNPTALA    660
WWEDMVAEFH DQVPFDGMWI DMNEPSNFIR GSEDGCPNNE LENPPYVPGV VGGTLQAATI    720
CASSHQFLST HYNLHNLYGL TEAIASHRAL VKARGTRPFV ISRSTFAGHG RYAGHWTGDV    780
WSSWEQLASS VPEILQFNLL GVPLVGADVC GFLGNTSEEL CVRWTQLGAF YPFMRNHNSL    840
LSLPQEPYSF SEPAQQAMRK ALTLRYALLP HLYTLFHQAH VAGETVARPL FLEFPKDSST    900
WTVDHQLLWG EALLITPVLQ AGKAEVTGYF PLGTWYDLQT VPVEALGSLP PPPAAPREPA    960
IHSEGQWVTL PAPLDTINVH LRAGYIIPLQ GPGLTTTESR QQPMALAVAL TKGGEARGEL   1020
FWDDGESLEV LERGAYTQVI FLARNNTIVN ELVRVTSEGA GLQLQKVTVL GVATAPQQVL   1080
SNGVPVSNFT YSPDTKVLDI CVSLLMGEQF LVSWC                              1115

SEQ ID NO: 60          moltype = AA  length = 19
FEATURE                Location/Qualifiers
source                 1..19
                       mol_type = protein
                       organism = Homo sapiens
SEQUENCE: 60
MGWSCIILFL VATATGAYA                                                 19

SEQ ID NO: 61          moltype =    length =
SEQUENCE: 61
000

SEQ ID NO: 62          moltype = AA  length = 5
FEATURE                Location/Qualifiers
source                 1..5
                       mol_type = protein
                       organism = synthetic construct
SEQUENCE: 62
GGGGS                                                                 5

SEQ ID NO: 63          moltype = AA  length = 10
FEATURE                Location/Qualifiers
source                 1..10
                       mol_type = protein
                       organism = synthetic construct
SEQUENCE: 63
GGGGSGGGGS                                                           10

SEQ ID NO: 64          moltype = AA  length = 952
FEATURE                Location/Qualifiers
source                 1..952
                       mol_type = protein
                       organism = synthetic construct
SEQUENCE: 64
MGVRHPPCSH RLLAVCALVS LATAALLGHI LLHDFLLVPR ELSGSSPVLE ETHPAHQQGA     60
SRPGPRDAQA HPGRPRAVPT QCDVPPNSRF DCAPDKAITQ EQCEARGCCY IPAKQGLQGA    120
QMGQPWCFFP PSYPSYKLEN LSSSEMGYTA TLTRTTPTFF PKDILTLRLD VMMETENRLH    180
```

```
FTIKDPANRR YEVPLETPRV HSRAPSPLYS VEFSEEPFGV IVHRQLDGRV LLNTTVAPLF    240
FADQFLQLST SLPSQYITGL AEHLSPLMLS TSWTRITLWN RDLAPTPGAN LYGSHPFYLA    300
LEDGGSAHGV FLLNSNAMDV VLQPSPALSW RSTGGILDVY IFLGPEPKSV VQQYLDVVGY    360
PFMPPYWGLG FHLCRWGYSS TAITRQVVEN MTRAHFPLDV QWNDLDYMDS RRDFTFNKDG    420
FRDFPAMVQE LHQGGRRYMM IVDPAISSSG PAGSYRPYDE GLRRGVFITN ETGQPLIGKV    480
WPGSTAFPDF TNPTALAWWE DMVAEFHDQV PFDGMWIDMN EPSNFIRGSE DGCPNNELEN    540
PPYVPGVVGG TLQAATICAS SHQFLSTHYN LHNLYGLTEA IASHRALVKA RGTRPFVISR    600
STFAGHGRYA GHWTGDVWSS WEQLASSVPE ILQFNLLGVP LVGADVCGFL GNTSEELCVR    660
WTQLGAFYPF MRNHNSLLSL PQEPYSFSEP AQQAMRKALT LRYALLPHLY TLFHQAHVEG    720
ETVARPLFLE FPKDSSTWTV DHQLLWGEAL LITPVLQAGK AEVTGYFPLG TWYDLQTVPI    780
EALGSLPPPP AAPREPAIHS EGQWVTLPAP LDTINVHLRA GYIIPLQGPG LTTTESRQQP    840
MALAVALTKG GEARGELFWD DGESLEVLER GAYTQVIFLA RNNTIVNELV RVTSEGAGLQ    900
LQKVTVLGVA TAPQQVLSNG VPVSNFTYSP DTKVLDICVS LLMGEQFLVS WC           952

SEQ ID NO: 65          moltype = AA  length = 925
FEATURE                Location/Qualifiers
source                 1..925
                       mol_type = protein
                       organism = synthetic construct
SEQUENCE: 65
GHILLHDFLL VPRELSGSSP VLEETHPAHQ QGASRPGPRD AQAHPGRPRA VPTQCDVPPN     60
SRFDCAPDKA ITQEQCEARG CCYIPAKQGL QGAQMGQPWC FFPPSYPSYK LENLSSSEMG    120
YTATLTRTTP TFFPKDILTL RLDVMMETEN RLHFTIKDPA NRRYEVPLET PRVHSRAPSP    180
LYSVEFSEEP FGVIVHRQLD GRVLLNTTVA PLFFADQFLQ LSTSLPSQYI TGLAEHLSPL    240
MLSTSWTRIT LWNRDLAPTP GANLYGSHPF YLALEDGGSA HGVFLLNSNA MDVVLQPSPA    300
LSWRSTGGIL DVYIFLGPEP KSVVQQYLDV VGYPFMPPYW GLGFHLCRWG YSSTAITRQV    360
VENMTRAHFP LDVQWNDLDY MDSRRDFTFN KDGFRDFPAM VQELHQGGRR YMMIVDPAIS    420
SSGPAGSYRP YDEGLRRGVF ITNETGQPLI GKVWPGSTAF PDFTNPTALA WWEDMVAEFH    480
DQVPFDGMWI DMNEPSNFIR GSEDGCPNNE LENPPYVPGV VGGTLQAATI CASSHQFLST    540
HYNLHNLYGL TEAIASHRAL VKARGTRPFV ISRSTFAGHG RYAGHWTGDV WSSWEQLASS    600
VPEILQFNLL GVPLVGADVC GFLGNTSEEL CVRWTQLGAF YPFMRNHNSL LSLPQEPYSF    660
SEPAQQAMRK ALTLRYALLP HLYTLFHQAH VAGETVARPL FLEFPKDSST WTVDHQLLWG    720
EALLITPVLQ AGKAEVTGYF PLGTWYDLQT VPIEALGSLP PPPAAPREPA IHSEGQWVTL    780
PAPLDTINVH LRAGYIIPLQ GPGLTTTESR QQPMALAVAL TKGGEARGEL FWDDGESLEV    840
LERGAYTQVI FLARNNTIVN ELVRVTSEGA GLQLQKVTVL GVATAPQQVL SNGVPVSNFT    900
YSPDTKVLDI CVSLLMGEQF LVSWC                                         925

SEQ ID NO: 66          moltype = AA  length = 883
FEATURE                Location/Qualifiers
source                 1..883
                       mol_type = protein
                       organism = synthetic construct
SEQUENCE: 66
AHPGRPRAVP TQCDVPPNSR FDCAPDKAIT QEQCEARGCC YIPAKQGLQG AQMGQPWCFF     60
PPSYPSYKLE NLSSSEMGYT ATLTRTTPTF FPKDILTLRL DVMMETENRL HFTIKDPANR    120
RYEVPLETPR VHSRAPSPLY SVEFSEEPFG VIVHRQLDGR VLLNTTVAPL FFADQFLQLS    180
TSLPSQYITG LAEHLSPLML STSWTRITLW NRDLAPTPGA NLYGSHPFYL ALEDGGSAHG    240
VFLLNSNAMD VVLQPSPALS WRSTGGILDV YIFLGPEPKS VVQQYLDVVG YPFMPPYWGL    300
GFHLCRWGYS STAITRQVVE NMTRAHFPLD VQWNDLDYMD SRRDFTFNKD GFRDFPAMVQ    360
ELHQGGRRYM MIVDPAISSS GPAGSYRPYD EGLRRGVFIT NETGQPLIGK VWPGSTAFPD    420
FTNPTALAWW EDMVAEFHDQ VPFDGMWIDM NEPSNFIRGS EDGCPNNELE NPPYVPGVVG    480
GTLQAATICA SSHQFLSTHY NLHNLYGLTE AIASHRALVK ARGTRPFVIS RSTFAGHGRY    540
AGHWTGDVWS SWEQLASSVP EILQFNLLGV PLVGADVCGF LGNTSEELCV RWTQLGAFYP    600
FMRNHNSLLS LPQEPYSFSE PAQQAMRKAL TLRYALLPHL YTLFHQAHVA GETVARPLFL    660
EFPKDSSTWT VDHQLLWGEA LLITPVLQAG KAEVTGYFPL GTWYDLQTVP IEALGSLPPP    720
PAAPREPAIH SEGQWVTLPA PLDTINVHLR AGYIIPLQGP GLTTTESRQQ PMALAVALTK    780
GGEARGELFW DDGESLEVLE RGAYTQVIFL ARNNTIVNEL VRVTSEGAGL QLQKVTVLGV    840
ATAPQQVLSN GVPVSNFTYS PDTKVLDICV SLLMGEQFLV SWC                     883

SEQ ID NO: 67          moltype = AA  length = 1157
FEATURE                Location/Qualifiers
source                 1..1157
                       mol_type = protein
                       organism = synthetic construct
SEQUENCE: 67
DKTHTCPPCP APEAAGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLSCAVK GFYPSDIAVE WESNGQPENN YKTTPPVLDS    180
DGSFFLVSKL TVDKSRWQQG NVFSCSVMHE ALHNHYTQKS LSLSPGKGGG GSGHILLHDF    240
LLVPRELSGS SPVLEETHPA HQQGASRPGP RDAQAHPGRP RAVPTQCDVP PNSRFDCAPD    300
KAITQEQCEA RGCCYIPAKQ GLQGAQMGQP WCFFPPSYPS YKLENLSSSE MGYTATLTRT    360
TPTFFPKDIL TLRLDVMMET ENRLHFTIKD PANRRYEVPL ETPRVHSRAP SPLYSVEFSE    420
EPFGVIVHRQ LDGRVLLNTT VAPLFFADQF LQLSTSLPSQ YITGLAEHLS PLMLSTSWTR    480
ITLWNRDLAP TPGANLYGSH PFYLALEDGG SAHGVFLLNS NAMDVVLQPS PALSWRSTGG    540
ILDVYIFLGP EPKSVVQQYL DVVGYPFMPP YWGLGFHLCR WGYSSTAITR QVVENMTRAH    600
FPLDVQWNDL DYMDSRRDFT FNKDGFRDFP AMVQELHQGG RRYMMIVDPA ISSSGPAGSY    660
RPYDEGLRRG VFITNETGQP LIGKVWPGST AFPDFTNPTA LAWWEDMVAE FHDQVPFDGM    720
WIDMNEPSNF IRGSEDGCPN NELENPPYVP GVVGGTLQAA TICASSHQFL STHYNLHNLY    780
GLTEAIASHR ALVKARGTRP FVISRSTFAG HGRYAGHWTG DVWSSWEQLA SSVPEILQFN    840
```

```
LLGVPLVGAD VCGFLGNTSE ELCVRWTQLG AFYPFMRNHN SLLSLPQEPY SFSEPAQQAM   900
RKALTLRYAL LPHLYTLFHQ AHVAGETVAR PLFLEFPKDS STWTVDHQLL WGEALLITPV   960
LQAGKAEVTG YFPLGTWYDL QTVPIEALGS LPPPPAAPRE PAIHSEGQWV TLPAPLDTIN  1020
VHLRAGYIIP LQGPGLTTTE SRQQPMALAV ALTKGGEARG ELFWDDGESL EVLERGAYTQ  1080
VIFLARNNTI VNELVRVTSE GAGLQLQKVT VLGVATAPQQ VLSNGVPVSN FTYSPDTKVL  1140
DICVSLLMGE QFLVSWC                                                1157

SEQ ID NO: 68           moltype = AA  length = 1115
FEATURE                 Location/Qualifiers
source                  1..1115
                        mol_type = protein
                        organism = synthetic construct
SEQUENCE: 68
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGKGGG GSAHPGRPRA   240
VPTQCDVPPN SRFDCAPDKA ITQEQCEARG CCYIPAKQGL QGAQMGQPWC FFPPSYPSYK   300
LENLSSSEMG YTATLTRTTP TFFPKDILTL RLDVMMETEN RLHFTIKDPA NRRYEVPLET   360
PRVHSRAPSP LYSVEFSEEP FGVIVHRQLD GRVLLNTTVA PLFFADQFLQ LSTSLPSQYI   420
TGLAEHLSPL MLSTSWTRIT LWNRDLAPTP GANLYGSHPF YLALEDGGSA HGVFLLNSNA   480
MDVVLQPSPA LSWRSTGGIL DVYIFLGPEP KSVVQQYLDV VGYPFMPPYW GLGFHLCRWG   540
YSSTAITRQV VENMTRAHFP LDVQWNDLDY MDSRRDFTFN KDGFRDFPAM VQELHQGGRR   600
YMMIVDPAIS SSGPAGSYRP YDEGLRRGVF ITNETGQPLI GKVWPGSTAF PDFTNPTALA   660
WWEDMVAEFH DQVPFDGMWI DMNEPSNFIR GSEDGCPNNE LENPPYVPGV VGGTLQAATI   720
CASSHQFLST HYNLHNLYGL TEAIASHRAL VKARGTRPFV ISRSTFAGHG RYAGHWTGDV   780
WSSWEQLASS VPEILQFNLL GVPLVGADVC GFLGNTSEEL CVRWTQLGAF YPFMRNHNSL   840
LSLPQEPYSF SEPAQQAMRK ALTLRYALLP HLYTLFHQAH VAGETVARPL FLEFPKDSST   900
WTVDHQLLWG EALLITPVLQ AGKAEVTGYF PLGTWYDLQT VPIEALGSLP PPAAPREPA   960
IHSEGQWVTL PAPLDTINVH LRAGYIIPLQ GPGLTTTESR QQPMALAVAL TKGGEARGEL  1020
FWDDGESLEV LERGAYTQVI FLARNNTIVN ELVRVTSEGA GLQLQKVTVL GVATAPQQVL  1080
SNGVPVSNFT YSPDTKVLDI CVSLLMGEQF LVSWC                            1115

SEQ ID NO: 69           moltype = AA  length = 1157
FEATURE                 Location/Qualifiers
source                  1..1157
                        mol_type = protein
                        organism = synthetic construct
SEQUENCE: 69
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALSA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGKGGG GSGHILLHDF   240
LLVPRELSGS SPVLEETHPA HQQGASRPGP RDAQAHPGRP RAVPTQCDVP PNSRFDCAPD   300
KAITQEQCEA RGCCYIPAKQ GLQGAQMGQP WCFFPPSYPS YKLENLSSSE MGYTATLTRT   360
TPTFFPKDIL TLRLDVMMET ENRLHFTIKD PANRRYEVPL ETPRVHSRAP SPLYSVEFSE   420
EPFGVIVHRQ LDGRVLLNTT VAPLFFADQF LQLSTSLPSQ YIITGLAEHLS PLMLSTSWTR   480
ITLWNRDLAP TPGANLYGSH PFYLALEDGG SAHGVFLLNS NAMDVVLQPS PALSWRSTGG   540
ILDVYIFLGP EPKSVVQQYL DVVGYPFMPP YWGLGFHLCR WGYSSTAITR QVVENMTRAH   600
FPLDVQWNDL DYMDSRRDFT FNKDGFRDFP AMVQELHQGG RRYMMIVDPA ISSSGPAGSY   660
RPYDEGLRRG VFITNETGQP LIGKVWPGST AFPDFTNPTA LAWWEDMVAE FHDQVPFDGM   720
WIDMNEPSNF IRGSEDGCPN NELENPPYVP GVVGGTLQAA TICASSHQFL STHYNLHNLY   780
GLTEAIASHR ALVKARGTRP FVISRSTFAG HGRYAGHWTG DVWSSWEQLA SSVPEILQFN   840
LLGVPLVGAD VCGFLGNTSE ELCVRWTQLG AFYPFMRNHN SLLSLPQEPY SFSEPAQQAM   900
RKALTLRYAL LPHLYTLFHQ AHVAGETVAR PLFLEFPKDS STWTVDHQLL WGEALLITPV   960
LQAGKAEVTG YFPLGTWYDL QTVPIEALGS LPPPPAAPRE PAIHSEGQWV TLPAPLDTIN  1020
VHLRAGYIIP LQGPGLTTTE SRQQPMALAV ALTKGGEARG ELFWDDGESL EVLERGAYTQ  1080
VIFLARNNTI VNELVRVTSE GAGLQLQKVT VLGVATAPQQ VLSNGVPVSN FTYSPDTKVL  1140
DICVSLLMGE QFLVSWC                                                1157

SEQ ID NO: 70           moltype = AA  length = 1115
FEATURE                 Location/Qualifiers
source                  1..1115
                        mol_type = protein
                        organism = synthetic construct
SEQUENCE: 70
DKTHTCPPCP APEAAGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALSA PIEKTISKAK   120
GQPREPQVYT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLSPGKGGG GSAHPGRPRA   240
VPTQCDVPPN SRFDCAPDKA ITQEQCEARG CCYIPAKQGL QGAQMGQPWC FFPPSYPSYK   300
LENLSSSEMG YTATLTRTTP TFFPKDILTL RLDVMMETEN RLHFTIKDPA NRRYEVPLET   360
PRVHSRAPSP LYSVEFSEEP FGVIVHRQLD GRVLLNTTVA PLFFADQFLQ LSTSLPSQYI   420
TGLAEHLSPL MLSTSWTRIT LWNRDLAPTP GANLYGSHPF YLALEDGGSA HGVFLLNSNA   480
MDVVLQPSPA LSWRSTGGIL DVYIFLGPEP KSVVQQYLDV VGYPFMPPYW GLGFHLCRWG   540
YSSTAITRQV VENMTRAHFP LDVQWNDLDY MDSRRDFTFN KDGFRDFPAM VQELHQGGRR   600
YMMIVDPAIS SSGPAGSYRP YDEGLRRGVF ITNETGQPLI GKVWPGSTAF PDFTNPTALA   660
WWEDMVAEFH DQVPFDGMWI DMNEPSNFIR GSEDGCPNNE LENPPYVPGV VGGTLQAATI   720
CASSHQFLST HYNLHNLYGL TEAIASHRAL VKARGTRPFV ISRSTFAGHG RYAGHWTGDV   780
```

-continued

```
WSSWEQLASS  VPEILQFNLL  GVPLVGADVC  GFLGNTSEEL  CVRWTQLGAF  YPFMRNHNSL   840
LSLPQEPYSF  SEPAQQAMRK  ALTLRYALLP  HLYTLFHQAH  VAGETVARPL  FLEFPKDSST   900
WTVDHQLLWG  EALLITPVLQ  AGKAEVTGYF  PLGTWYDLQT  VPIEALGSLP  PPPAAPREPA   960
IHSEGQWVTL  PAPLDTINVH  LRAGYIIPLQ  GPGLTTTESR  QQPMALAVAL  TKGGEARGEL  1020
FWDDGESLEV  LERGAYTQVI  FLARNNTIVN  ELVRVTSEGA  GLQLQKVTVL  GVATAPQQVL  1080
SNGVPVSNFT  YSPDTKVLDI  CVSLLMGEQF  LVSWC                              1115
```

FUSION PROTEINS COMPRISING ACID ALPHA-GLUCOSIDASE ENZYMES AND METHODS THEREOF

CROSS-REFERENCE TO RELATED APPLICATIONS

This application is a continuation of International Application No. PCT/US2024/060936, filed Dec. 19, 2024, which claims priority to U.S. Provisional Application Ser. No. 63/612,862, filed Dec. 20, 2023. The entire content of the applications referenced above are hereby incorporated by reference herein.

SEQUENCE LISTING

The instant application contains a Sequence Listing which has been submitted electronically in XML file format and is hereby incorporated by reference in its entirety. Said XML copy, created on Mar. 6, 2025, is named 02900_057US1_SL.xml and is 93,455 bytes in size.

BACKGROUND

Pompe disease is a lysosomal storage disorder caused by genetic mutations in the GAA gene. These mutations reduce or largely eliminate acid alpha-glucosidase (GAA) enzyme function, which results in the accumulation of lysosomal glycogen in multiple organs and tissues, including the brain and muscle. While current treatments for Pompe disease may be administered intravenously, they have little effect on the brain due to difficulties in delivering the recombinant enzyme across the blood-brain barrier (BBB). Accordingly, there is a need for more effective therapies that treat both the peripheral (e.g., neuromuscular, respiratory, and/or cardiac) and central nervous system (CNS) symptoms of Pompe disease.

SUMMARY

Thus, provided herein is a specific enzyme replacement therapy, which has the capability of crossing the BBB and treating both the peripheral and CNS manifestations of Pompe disease. In particular, certain embodiments provide a protein comprising (a) a first Fc polypeptide linked to an acid alpha-glucosidase (GAA) enzyme; and (b) a second Fc polypeptide; wherein the first and/or second Fc polypeptide is a modified Fc that is capable of binding (e.g., specifically binding) to a blood-brain barrier (BBB) receptor, e.g., a transferrin receptor (TfR). In certain embodiments, the second Fc polypeptide forms an Fc dimer with the first Fc polypeptide.

In certain embodiments, the first Fc polypeptide is a modified Fc that is capable of binding (e.g., specifically binding) to TfR. In certain embodiments, the first Fc polypeptide is a modified Fc comprising a sequence having at least 90% identity to SEQ ID NO: 32 or 40 (e.g., SEQ ID NO:32) and is capable of specifically binding to a TfR.

In certain embodiments, the first Fc polypeptide 1) comprises a sequence having at least 90% identity to SEQ ID NO: 32 or 40 (e.g., SEQ ID NO:32); 2) is capable of specifically binding to a TfR; and 3) has Ala at position 389, according to EU numbering. In certain embodiments, the first Fc polypeptide further comprises Glu at position 380; and Asn at position 390, according to EU numbering. In certain embodiments, the first Fc polypeptide further comprises at the following positions, according to EU numbering: Tyr at position 384; Thr at position 386; Glu at position 387; Trp at position 388; Thr at position 413; Glu at position 415; Glu at position 416; and Phe at position 421.

In certain embodiments, the second Fc polypeptide is a modified Fc that is capable of binding (e.g., specifically binding) to TfR. In certain embodiments, the second Fc polypeptide is a modified Fc comprising a sequence having at least 90% identity to SEQ ID NO: 32 or 40 (e.g., SEQ ID NO:32) and is capable of specifically binding to a TfR.

In certain embodiments, the second Fc polypeptide 1) comprises a sequence having at least 90% identity to SEQ ID NO: 32 or 40 (e.g., SEQ ID NO:32); 2) is capable of specifically binding to a TfR; and 3) has Ala at position 389, according to EU numbering. In certain embodiments, the second Fc polypeptide further comprises Glu at position 380; and Asn at position 390, according to EU numbering. In certain embodiments, the second Fc polypeptide further comprises at the following positions, according to EU numbering: Tyr at position 384; Thr at position 386; Glu at position 387; Trp at position 388; Thr at position 413; Glu at position 415; Glu at position 416; and Phe at position 421.

Certain embodiments provide a protein comprising:
a. a first Fc polypeptide linked to an acid alpha-glucosidase (GAA) enzyme; and
b. a second Fc polypeptide that comprises a sequence having at least 90% identity to SEQ ID NO: 32 and that is capable of specifically binding to a transferrin receptor (TfR). In certain embodiments, the N-terminus of the first Fc polypeptide is linked to the GAA enzyme. In certain embodiments, the C-terminus of the first Fc polypeptide is linked to the GAA enzyme.

In certain embodiments, the second Fc polypeptide has Ala at position 389, according to EU numbering.

In certain embodiments, the second Fc polypeptide further comprises Glu at position 380; and Asn at position 390, according to EU numbering.

In certain embodiments, the second Fc polypeptide further comprises at the following positions, according to EU numbering: Tyr at position 384; Thr at position 386; Glu at position 387; Trp at position 388; Thr at position 413; Glu at position 415; Glu at position 416; and Phe at position 421.

In certain embodiments, the first Fc polypeptide comprises an amino acid sequence having at least 95% or 100% identity to any one of SEQ ID NOs: 9-16 and 21-24. In certain embodiments, the first Fc polypeptide comprises an amino acid sequence having at least 95% or 100% identity to any one of SEQ ID NOs: 11-16, and 21-24. In certain embodiments, the first Fc polypeptide comprises an amino acid sequence having at least 95% or 100% identity to any one of SEQ ID NOs: 11, 12, 21, and 22. In certain embodiments, the first Fc polypeptide comprises an amino acid sequence having at least 95% or 100% identity to any one of SEQ ID NOs:15, 16, 23, and 24. In certain embodiments, the first Fc polypeptide comprises an amino acid sequence having at least 95% or 100% identity to any one of SEQ ID NOs: 17-20 and 25-26.

In certain embodiments, the second Fc polypeptide comprises an amino acid sequence having at least 95% or 100% identity to any one of SEQ ID NOs: 29-36 and 41-44. In certain embodiments, the second Fc polypeptide comprises an amino acid sequence having at least 95% or 100% identity to any one of SEQ ID NOs: 31-36 and 41-44. In certain embodiments, the second Fc polypeptide comprises an amino acid sequence having at least 95% or 100% identity to any one of SEQ ID NOs: 31, 32, 41 and 42. In certain embodiments, the second Fc polypeptide comprises an amino acid sequence having at least 95% or 100% identity to any one of SEQ ID NOs:35, 36, 43 and 44. In certain embodiments, the second Fc polypeptide comprises an amino acid sequence having at least 95% or 100% identity to any one of SEQ ID NOs: 37-40.

In certain embodiments, the first Fc polypeptide comprises an amino acid sequence having at least 95% or 100% identity to any one of SEQ ID NOs: 9-16 and 21-24; and the second Fc polypeptide comprises an amino acid sequence having at least 95% or 100% identity to any one of SEQ ID NOs: 29-36 and 41-44.

In certain embodiments, the first Fc polypeptide comprises an amino acid sequence having at least 95% or 100% identity to any one of SEQ ID NOs: 17-20 and 25-26; and the second Fc polypeptide comprises an amino acid sequence having at least 95% or 100% identity to any one of SEQ ID NOs: 37-40.

In certain embodiments, the first Fc polypeptide linked to the GAA enzyme comprises the amino acid sequence of any one of SEQ ID NOs: 56-59 and 67-70; and the second Fc polypeptide comprises the amino acid sequence of any one of SEQ ID NOs: 41-44. In certain embodiments, the first Fc polypeptide linked to the GAA enzyme comprises the amino acid sequence of any one of SEQ ID NOs: 56-57 and 67-68; and the second Fc polypeptide comprises the amino acid sequence of any one of SEQ ID NOs: 41-42. In certain embodiments, the first Fc polypeptide linked to the GAA enzyme comprises an amino acid sequence of any one of SEQ ID NOs: 58-59 and 69-70; and the second Fc polypeptide comprises the amino acid sequence of any one of SEQ ID NOs: 43-44.

In certain embodiments, the first Fc polypeptide is not modified to bind to a blood-brain barrier (BBB) receptor and the second Fc polypeptide is modified to specifically bind to a TfR.

Certain embodiments provide a polypeptide comprising an Fc polypeptide that is linked to a GAA enzyme, wherein the Fc polypeptide comprises a sequence having at least 90% identity to SEQ ID NO: 12 and contains one or more modifications that promote its heterodimerization to another Fc polypeptide. In certain embodiments, the N-terminus of the Fc polypeptide is linked to the GAA enzyme. In certain embodiments, the C-terminus of the Fc polypeptide is linked to the GAA enzyme. In certain embodiments, the Fc polypeptide is linked to the GAA enzyme by a peptide bond or by a polypeptide linker. In certain embodiments, the polypeptide comprises from N- to C-terminus: the GAA enzyme; a polypeptide linker; and the Fc polypeptide. In certain embodiments, the polypeptide comprises from N- to C-terminus: the Fc polypeptide; a polypeptide linker; and the GAA enzyme. In certain embodiments, the Fc polypeptide comprises T366S, L368A, and Y407V substitutions, according to EU numbering. In certain embodiments, the Fc polypeptide comprises substitutions of Ala at position 234 and Ala at position 235; Ala at position 234, Ala at position 235 and Gly at position 329; or Ala at position 234, Ala at position 235 and Ser at position 329, according to EU numbering. In certain embodiments, the polypeptide comprises an amino acid sequence having at least 95% or 100% identity to any one of SEQ ID NOs:48-59 and 67-70 (e.g., any one of SEQ ID NOs: 56-59 and 67-70).

Certain embodiments provide a protein comprising 1) a polypeptide comprising an Fc polypeptide that is linked to an acid alpha-glucosidase (GAA) enzyme, wherein the Fc polypeptide comprises a sequence having at least 90% identity to SEQ ID NO: 12 and contains one or more modifications that promote its heterodimerization to another Fc polypeptide, and 2) the other Fc polypeptide.

Certain embodiments provide a pharmaceutical composition comprising a protein as described herein or a polypeptide as described herein and a pharmaceutically acceptable carrier and/or excipient.

Certain embodiments provide a polynucleotide comprising a nucleic acid sequence encoding a polypeptide as described herein (e.g., a GAA-Fc fusion polypeptide as described herein). Certain embodiments provide a vector comprising a polynucleotide as described herein. Certain embodiments provide a host cell comprising a polynucleotide as described herein or a vector as described herein. In certain embodiments, the host cell further comprises a polynucleotide comprising a nucleic acid sequence encoding another polypeptide described herein (e.g., the other Fc polypeptide, such as a TfR-binding modified Fc polypeptide). Certain embodiments provide a method for producing a polypeptide comprising an Fc polypeptide that is linked to a GAA enzyme, comprising culturing a host cell under conditions in which the polypeptide encoded by a polynucleotide as described herein is expressed.

Certain embodiments provide a pair of polynucleotides comprising a first and a second polynucleotide, wherein the first polynucleotide comprises a first nucleic acid sequence encoding a first Fc polypeptide linked to a GAA enzyme as described herein; and the second polynucleotide comprises a second nucleic acid sequence encoding a second Fc polypeptide as described herein. Certain embodiments provide one or more vectors comprising a pair of polynucleotides as described herein. For example, certain embodiments provide a single vector comprising the pair of polynucleotides. Other embodiments provide two vectors, wherein the first vector comprises the first polynucleotide from the pair and the second vector comprises the second polynucleotide from the pair. Certain embodiments provide a host cell comprising a pair of polynucleotides as described herein, or one or more vectors as described herein. Certain embodiments provide a method for producing a protein comprising a first Fc polypeptide linked to a GAA enzyme; and a second Fc polypeptide, comprising culturing a host cell under conditions in which the polypeptides encoded by a pair of polynucleotides as described herein are expressed.

Certain embodiments provide a method of treating Pompe disease, the method comprising administering a protein as described herein or a polypeptide as described herein to a patient in need thereof. In certain embodiments, a therapeutically effective amount of the protein or polypeptide is administered.

Certain embodiments provide a protein as described herein or a polypeptide as described herein for use in treating Pompe disease in a patient in need thereof.

Certain embodiments provide the use of a protein as described herein or a polypeptide as described herein in the preparation of a medicament for treating Pompe disease in a patient in need thereof.

Certain embodiments provide a method of decreasing the accumulation of a toxic metabolic product in a patient having Pompe disease, the method comprising administering a protein as described herein or a polypeptide as described herein to the patient. In certain embodiments, an effective amount (e.g., a therapeutically effective amount) of the protein or polypeptide is administered.

Certain embodiments provide a protein as described herein or a polypeptide as described herein for use in decreasing the accumulation of a toxic metabolic product in a patient having Pompe disease.

Certain embodiments provide the use of a protein as described herein or a polypeptide as described herein in the preparation of a medicament for decreasing the accumulation of a toxic metabolic product in a patient having Pompe disease.

In certain embodiments, the toxic metabolic product is glycogen.

DETAILED DESCRIPTION

Figures 1A, 1B:
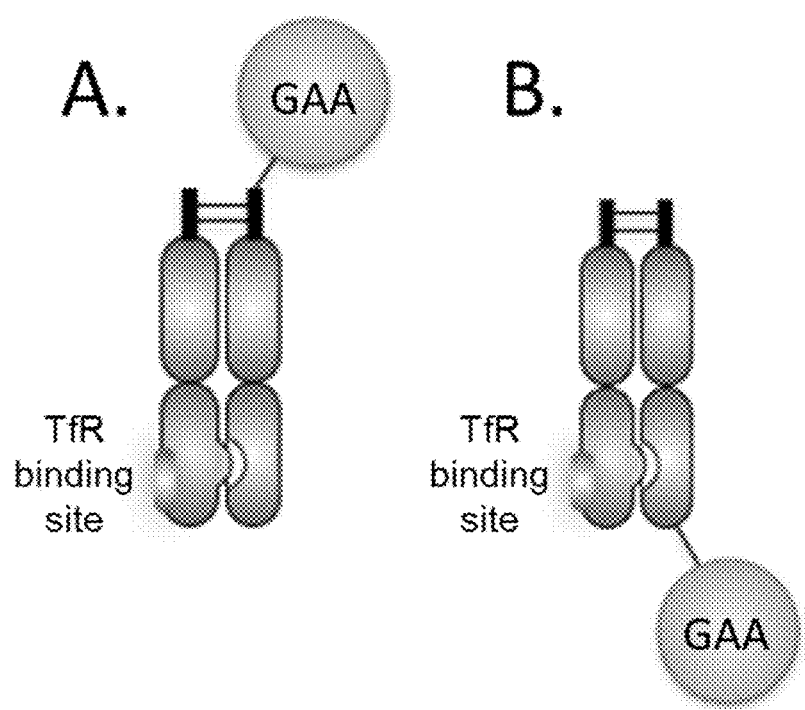
FIGS. 1A-1B. Illustration of exemplary ETV:GAA fusion proteins, wherein the GAA enzyme is fused to (FIG. 1A) the N-terminus of an Fc polypeptide; or to (FIG. 1B) the C-terminus of an Fc polypeptide.

There is currently a need for new therapeutics for the treatment of Pompe disease, specifically therapeutics that treat the neurological symptoms of the disease. Described herein is a specific enzyme replacement therapy termed ETV:GAA, which has the capability of crossing the BBB and treating both the peripheral and CNS manifestations of Pompe disease. As used herein, the term "ETV:GAA" refers to a protein (e.g., a dimeric protein) that is capable of being transported across the BBB and comprises a first Fc polypeptide linked (e.g., fused) to a GAA enzyme (e.g., a wild-type GAA enzyme, a GAA enzyme variant, or a catalytically active fragment of a wild-type GAA enzyme or GAA enzyme variant); and a second Fc polypeptide.

Protein Molecules Comprising a GAA Enzyme-Fc Fusion Polypeptide

As described herein, certain embodiments provide a protein molecule comprising a GAA enzyme-Fc fusion polypeptide. A GAA enzyme incorporated into the protein is catalytically active, i.e., it retains the enzymatic activity. In some aspects, a protein described herein comprises: (a) a first Fc polypeptide, which may contain modifications (e.g., one or more modifications that promote heterodimerization) or may be a wild-type Fc polypeptide; and a GAA enzyme; and (b) a second Fc polypeptide, which may contain modifications (e.g., one or more modifications that promote heterodimerization) or may be a wild-type Fc polypeptide; and optionally a GAA enzyme, wherein the first and/or second Fc polypeptide comprises modifications that result in binding to a blood-brain barrier (BBB) receptor, e.g., a transferrin receptor (TfR).

In some embodiments, a protein as described herein comprises a full-length GAA enzyme. In some embodiments, a protein as described herein comprises a mature GAA enzyme. In some embodiments, the GAA enzyme is a wild-type GAA enzyme. In some embodiments, the GAA enzyme is a GAA enzyme variant. In certain embodiments, the GAA enzyme variant comprises an amino acid sequence having about 85%-99%, 90%-99%, 95%-99%, 96%-99%, 97%-99%, 98%-99%, or 99% identity (e.g., 85% to 99%, 90% to 99% or 95% to 99% identity) to a wild-type GAA enzyme (e.g., SEQ ID NO:45). In certain embodiments, the GAA enzyme variant comprises H199R, R223H, and/or V780I substitutions, wherein the positions and residues are with respect to SEQ ID NO:45. In certain embodiments, the GAA enzyme variant comprises H199R, R223H, and V780I substitutions. In some embodiments, the GAA enzyme is a catalytically active fragment of a full-length GAA enzyme that is a wild-type GAA enzyme or a GAA enzyme variant. For example, the full-length GAA enzyme sequence may be truncated (e.g., no more than about 20%, 15%, 10%, 5% or less of the full-length, wild-type GAA enzyme or GAA enzyme variant has been truncated). In certain embodiments, the catalytically active fragment is a fragment of a full-length, wild-type GAA enzyme or GAA enzyme variant that has been truncated in length by about 200, 150, 100, or 50 or fewer amino acids. In certain embodiments, the GAA enzyme is truncated at the N-terminus. In certain embodiments, the GAA enzyme is truncated at the C-terminus. In certain embodiments, the catalytically active fragment is a fragment of a full-length, wild-type GAA enzyme or GAA enzyme variant that has been truncated in length by 69 amino acids at the N-terminus.

In some embodiments, the GAA enzyme comprises an amino acid sequence having at least 85%, at least 90%, at least 95% identity, at least 96% identity, at least 97% identity, at least 98% identity, or at least 99% identity (e.g., 85%, 90%, or 95% identity) to an amino acid sequence of any one of SEQ ID NOs:45-47 and 64-66, or comprises the amino acid sequence of any one of SEQ ID NOs:45-47 and 64-66. In some embodiments, the GAA enzyme comprises an amino acid sequence having at least 85%, at least 90%, at least 95% identity, at least 96% identity, at least 97% identity, at least 98% identity, or at least 99% identity (e.g., 85%, 90%, or 95% identity) to the amino acid sequence of SEQ ID NO:45, or comprises the amino acid sequence of SEQ ID NO:45. In some embodiments, the GAA enzyme comprises an amino acid sequence having at least 85%, at least 90%, at least 95% identity, at least 96% identity, at least 97% identity, at least 98% identity, or at least 99% identity (e.g., 85%, 90%, or 95% identity) to the amino acid sequence of SEQ ID NO:46, or comprises the amino acid sequence of SEQ ID NO:46. In some embodiments, the GAA enzyme comprises an amino acid sequence having at least 85%, at least 90%, at least 95% identity, at least 96% identity, at least 97% identity, at least 98% identity, or at least 99% identity (e.g., 85%, 90%, or 95% identity) to the amino acid sequence of SEQ ID NO: 47, or comprises the amino acid sequence of SEQ ID NO: 47. In some embodiments, the GAA enzyme comprises an amino acid sequence having at least 85%, at least 90%, at least 95% identity, at least 96% identity, at least 97% identity, at least 98% identity, or at least 99% identity (e.g., 85%, 90%, or 95% identity) to the amino acid sequence of SEQ ID NO: 64, or comprises the amino acid sequence of SEQ ID NO: 64. In some embodiments, the GAA enzyme comprises an amino acid sequence having at least 85%, at least 90%, at least 95% identity, at least 96% identity, at least 97% identity, at least 98% identity, or at least 99% identity (e.g., 85%, 90%, or 95% identity) to the amino acid sequence of SEQ ID NO: 65, or comprises the amino acid sequence of SEQ ID NO: 65. In some embodiments, the GAA enzyme comprises an amino acid sequence having at least 85%, at least 90%, at least 95% identity, at least 96% identity, at least 97% identity, at least 98% identity, or at least 99% identity (e.g., 85%, 90%, or 95% identity) to the amino acid sequence of SEQ ID NO: 66, or comprises the amino acid sequence of SEQ ID NO: 66.

As discussed above, in some embodiments, the GAA enzyme is a variant or a catalytically active fragment of a wild-type GAA enzyme or GAA enzyme variant (e.g., comprises a GAA amino acid sequence described herein). In some embodiments, a catalytically active variant or fragment of a GAA enzyme has at least 50%, at least 55%, at least 60%, at least 65%, at least 70%, at least 75%, at least 80%, at least 85%, at least 90%, at least 95%, or greater of the activity (e.g., at least 50% of the activity) of a corresponding wild-type GAA enzyme. In some embodiments, a catalytically active fragment has at least 50%, at least 55%, at least 60%, at least 65%, at least 70%, at least 75%, at least 80%, at least 85%, at least 90%, at least 95%, or greater of the activity (e.g., at least 50% of the activity) of a corresponding full-length, wild-type GAA enzyme or GAA enzyme variant.

In some embodiments, a GAA enzyme (e.g., a catalytically active GAA enzyme variant or fragment) that is present in a protein described herein, retains at least 25% of its activity compared to its activity when not joined to an Fc polypeptide or a TfR-binding Fc polypeptide. In some embodiments, a GAA enzyme retains at least 10%, or at least 15%, 20%, 25%, 30%, 35%, 40%, 45%, 50%, 55%, 60%, 65%, 70%, 75%, 80%, 85%, 90%, or 95%, of its activity compared to its activity when not joined to an Fc polypeptide or a TfR-binding Fc polypeptide. In some embodiments, a GAA enzyme retains at least 80%, 85%, 90%, or 95% of its activity compared to its activity when not joined to an Fc polypeptide or a TfR-binding Fc polypeptide. In some embodiments, fusion to an Fc polypeptide does not decrease the activity of the GAA enzyme. In some embodiments, fusion to a TfR-binding Fc polypeptide does not decrease the activity of the GAA enzyme.

Enzymatic activity may be measured using an assay known in the art or described herein (see, e.g., the Examples). For example, in certain embodiments, the enzymatic activity is measured by an in vitro reaction with a 4-Methylumbelliferyl α-D-glucopyranoside substrate.

Fc Polypeptide Modifications

An Fc polypeptide incorporated in a fusion protein described herein may comprise certain modifications. For example, an Fc polypeptide may comprise modifications that result in binding to a blood-brain barrier (BBB) receptor, e.g., a transferrin receptor (TfR). Additionally, an Fc polypeptide may comprise other modifications, such as modifications that promote heterodimerization, increase serum stability or serum half-life, modulate effector function, influence glycosylation, and/or reduce immunogenicity in humans. Thus, in certain embodiments, a fusion protein described herein comprises two Fc polypeptides, wherein one Fc is a wild-type Fc polypeptide, e.g., a human IgG1 Fc polypeptide; and the other Fc is modified to bind to a blood-brain barrier (BBB) receptor, e.g., transferrin receptor (TfR), and optionally further comprises one or more additional modifications. In certain other embodiments, both Fc polypeptides each comprise independently selected modifications (e.g., a modification described herein). For example, in certain embodiments, a fusion protein described herein comprises two Fc polypeptides, wherein one Fc is not modified to bind to a BBB receptor but comprises one or more other modifications described herein; and the other Fc is modified to bind to a blood-brain barrier (BBB) receptor, e.g., transferrin receptor (TfR), and optionally further comprises one or more additional modifications. In certain other embodiments, a fusion protein described herein comprises two Fc polypeptides, wherein both Fc polypeptides are modified to bind to a blood-brain barrier (BBB) receptor, e.g., transferrin receptor (TfR), and optionally each independently further comprise one or more additional modifications.

Amino acid residues designated in various Fc modifications, including those introduced in a modified Fc polypeptide that binds to a BBB receptor, e.g., TfR, are numbered herein using EU index numbering. Any Fc polypeptide, e.g., an IgG polypeptide (i.e., a IgG1, IgG2, IgG3, or IgG4 Fc polypeptide), may have modifications, e.g., amino acid substitutions, in one or more positions using EU index numbering as described herein. In some embodiments, the amino acid residues designated in various Fc modifications using EU index numbering are with respect to an IgG1 Fc polypeptide.

A modified (e.g., enhancing heterodimerization and/or BBB receptor-binding) Fc polypeptide present in a fusion protein described herein can have at least 70% identity, at least 75% identity, at least 80% identity, at least 85% identity, at least 90% identity, at least 95% identity, at least 96% identity, at least 97% identity, at least 98% identity, or at least 99% identity to a native Fc region sequence or a fragment thereof, e.g., a fragment of at least 50 amino acids or at least 100 amino acids, or greater in length. In some embodiments, the native Fc amino acid sequence is the Fc region sequence of SEQ ID NO:1. In some embodiments, the modified Fc polypeptide has at least 70% identity, at least 75% identity, at least 80% identity, at least 85% identity, at least 90% identity, at least 95% identity, at least 96% identity, at least 97% identity, at least 98% identity, or at least 99% identity to amino acids 1-110 of SEQ ID NO:1, or to amino acids 111-217 of SEQ ID NO:1, or a fragment thereof, e.g., a fragment of at least 50 amino acids or at least 100 amino acids, or greater in length.

In some embodiments, a modified (e.g., enhancing heterodimerization and/or BBB receptor-binding) Fc polypeptide comprises at least 50 amino acids, or at least 60, 65, 70, 75, 80, 85, 90, or 95 or more, or at least 100 amino acids, or more, that correspond to a native Fc region amino acid sequence. In some embodiments, the modified Fc polypeptide comprises at least 25 contiguous amino acids, or at least 30, 35, 40, or 45 contiguous amino acids, or 50 contiguous amino acids, or at least 60, 65, 70, 75, 80 85, 90, or 95 or more contiguous amino acids, or 100 or more contiguous amino acids, that correspond to a native Fc region amino acid sequence, such as SEQ ID NO:1.

Modifications for Blood-Brain Barrier (BBB) Receptor Binding

In some aspects, provided herein are fusion proteins that are capable of being transported across the blood-brain barrier (BBB) of a subject. Such a protein comprises a modified Fc polypeptide that binds to a BBB receptor. BBB receptors are expressed on BBB endothelia, as well as other cell and tissue types. In some embodiments, the BBB receptor is a transferrin receptor (TfR).

In some embodiments a fusion protein described herein specifically binds to TfR. In some embodiments a fusion protein described herein specifically binds to TfR with an affinity of from about 50 nM to about 500 nM. In some embodiments, the protein binds (e.g., specifically binds) to a TfR with an affinity of about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 nM. In some embodiments, the protein binds to a TfR with an affinity of from about 100 to about 500 nM. In some embodiments, the protein binds to a TfR with an affinity of from about 100 nM to about 300 nM, or from about 200 nM to about 300 nM, or from about 200 nM to about 450 nM. In some embodiments, the protein binds to a TfR with an affinity of about 250 nM. In some embodiments, the protein binds to a TfR with an affinity of about 300 nM. In some embodiments, the protein binds to a TfR with an affinity of from about 150 to about 400 nM, or from about 200 to about 400 nM, or from about 250 nM to about 350 nM, or from about 250 nM to about 300 nM, or from about 300 to about 350 nM. In some embodiments, the protein binds to a TfR with an affinity of from about 200 to about 400 nM.

In some embodiments, a modified Fc polypeptide that specifically binds to TfR comprises substitutions in a CH3 domain. In some embodiments, a modified Fc polypeptide comprises a human Ig CH3 domain, such as an IgG CH3 domain, that is modified for TfR-binding activity. The CH3 domain can be of any IgG subtype, i.e., from IgG1, IgG2, IgG3, or IgG4. In the context of IgG antibodies, a CH3 domain refers to the segment of amino acids from about position 341 to about position 447 as numbered according to the EU numbering scheme.

In some embodiments, a modified Fc polypeptide that specifically binds to TfR binds to the apical domain of TfR and may, e.g., bind to TfR without blocking or otherwise inhibiting binding of transferrin to TfR. In some embodiments, binding of transferrin to TfR is not substantially inhibited. In some embodiments, binding of transferrin to TfR is inhibited by less than about 50% (e.g., less than about 45%, 40%, 35%, 30%, 25%, 20%, 15%, 10%, or 5%). In some embodiments, binding of transferrin to TfR is inhibited by less than about 20% (e.g., less than about 15%, 10%, 9%, 8%, 7%, 6%, 5%, 4%, 3%, 2%, or 1%).

In some embodiments, a modified (e.g., BBB receptor-binding) Fc polypeptide present in a fusion protein described herein comprises substitutions at amino acid positions 384, 386, 387, 388, 389, 413, 415, 416, and 421, according to the EU numbering scheme.

In some embodiments, a modified Fc polypeptide that specifically binds to TfR comprises Ala at position 389, according to EU numbering. In some embodiments, a modified Fc polypeptide that specifically binds to TfR comprises at the following positions, according to EU numbering: Glu at position 380; Ala at position 389; and Asn at position 390. In some embodiments, a modified Fc polypeptide that specifically binds to TfR comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421.

In additional embodiments, the modified Fc polypeptide further comprises one, two, or three substitutions at positions comprising 414, 424, and 426, according to the EU numbering scheme. In some embodiments, position 414 is Lys, Arg, Gly, or Pro; position 424 is Ser, Thr, Glu, or Lys; and/or position 426 is Ser, Trp, or Gly.

In some embodiments, the modified Fc polypeptide has at least 70% identity, at least 75% identity, at least 80% identity, at least 85% identity, at least 90% identity, at least 95% identity, at least 96% identity, at least 97% identity, at least 98% identity, or at least 99% identity to amino acids 111-217 of SEQ ID NO:27; and comprises the amino acids at EU index positions 380, 384-390 and/or 413-421 of SEQ ID NO:27. In some embodiments, the modified Fc polypeptide has at least 70% identity, at least 75% identity, at least 80% identity, at least 85% identity, at least 90% identity, at least 95% identity, at least 96% identity, at least 97% identity, at least 98% identity, or at least 99% identity to amino acids 111-216 of SEQ ID NO: 28; and comprises the amino acids at EU index positions 380, 384-390 and/or 413-421 of SEQ ID NO:27 or 28. In some embodiments, the modified Fc polypeptide has at least 70% identity, at least 75% identity, at least 80% identity, at least 85% identity, at least 90% identity, at least 95% identity, at least 96% identity, at least 97% identity, at least 98% identity, or at least 99% identity to SEQ ID NO:27 or 28; and comprises the amino acids at EU index positions 380, 384-390 and/or 413-421 of SEQ ID NO:27 or 28.

In some embodiments, the modified Fc polypeptide has at least 75% identity, at least 80% identity, at least 85% identity, at least 90% identity, at least 95% identity, at least 96% identity, at least 97% identity, at least 98% identity, or at least 99% identity to SEQ ID NO:27 or 28, and has Ala at position 389, according to EU numbering. In some embodiments, the modified Fc polypeptide has at least 75% identity, at least 80% identity, at least 85% identity, at least 90% identity, at least 95% identity, at least 96% identity, at least 97% identity, at least 98% identity, or at least 99% identity to SEQ ID NO:27 or 28 and comprises at the following positions, according to EU numbering: Glu at position 380; Ala at position 389; and Asn at position 390. In some embodiments, the modified Fc polypeptide has at least 75% identity, at least 80% identity, at least 85% identity, at least 90% identity, at least 95% identity, at least 96% identity, at least 97% identity, at least 98% identity, or at least 99% identity to SEQ ID NO:27 or 28 and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421.

In some embodiments, the modified Fc polypeptide comprises the amino acid sequence of SEQ ID NO:27 or 28.

Additional Fc Polypeptide Mutations

In some aspects, a fusion protein described herein comprises two Fc polypeptides, wherein one or both Fc polypeptides each comprise independently selected modifications (e.g., a modification described herein). Non-limiting examples of other mutations that can be introduced into one or both Fc polypeptides include, e.g., mutations to increase serum stability or serum half-life, to modulate effector function, to influence glycosylation, to reduce immunogenicity in humans, and/or to provide for knob and hole heterodimerization of the Fc polypeptides. Examples of various modifications that may be included in an Fc polypeptide are described in WO2019/070577, which is incorporated by reference herein in its entirety for all purposes.

In some embodiments, the Fc polypeptides present in the fusion protein each independently have an amino acid sequence identity of at least about 75%, 80%, 85%, 90%, 95%, 96%, 97%, 98%, or 99% to a corresponding wild-type Fc polypeptide (e.g., a human IgG polypeptide (i.e., a IgG1, IgG2, IgG3, or IgG4 Fc polypeptide)).

In some embodiments, the Fc polypeptides present in the fusion protein include knob and hole mutations to promote heterodimer formation and hinder homodimer formation. Generally, the modifications introduce a protuberance ("knob") at the interface of one polypeptide and a corresponding cavity ("hole") in the interface of another polypeptide, such that the protuberance can be positioned in the cavity so as to promote heterodimer formation and thus hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). In some embodiments, such additional mutations are at a position in the Fc polypeptide that does not have a negative effect on binding of the polypeptide to a BBB receptor, e.g., TfR.

In one illustrative embodiment of a knob and hole approach for dimerization, position 366 (numbered according to the EU numbering scheme) of one of the Fc polypeptides present in the fusion protein comprises a tryptophan in place of a native threonine. The other Fc polypeptide in the dimer has a valine at position 407 (numbered according to the EU numbering scheme) in place of the native tyrosine. The other Fc polypeptide may further comprise a substitution in which the native threonine at position 366 (numbered according to the EU numbering scheme) is substituted with a serine and a native leucine at position 368 (numbered according to the EU numbering scheme) is substituted with an alanine. Thus, one of the Fc polypeptides of a fusion protein described herein has the T366W knob mutation and the other Fc polypeptide has the Y407V mutation, which is typically accompanied by the T366S and L368A hole mutations. In certain embodiments, the first Fc polypeptide contains the T366S, L368A, and Y407V substitutions and the second Fc polypeptide contains the T366W substitution. In certain other embodiments, the first Fc polypeptide contains the T366W substitution and the second Fc polypeptide contains the T366S, L368A, and Y407V substitutions.

In some embodiments, modifications to enhance serum half-life may be introduced. For example, in some embodiments, one or both Fc polypeptides present in a fusion protein described herein may comprise a tyrosine at position 252, a threonine at position 254, and a glutamic acid at position 256, as numbered according to the EU numbering scheme. Thus, one or both Fc polypeptides may have M252Y, S254T, and T256E substitutions. Alternatively, one or both Fc polypeptides may have M428L and N434S substitutions, as numbered according to the EU numbering scheme. Alternatively, one or both Fc polypeptides may have an N434S or N434A substitution.

In some embodiments, one or both Fc polypeptides present in a fusion protein described herein may comprise modifications that reduce effector function, i.e., having a reduced ability to induce certain biological functions upon binding to an Fc receptor expressed on an effector cell that mediates the effector function. Examples of antibody effector functions include, but are not limited to, C1q binding and complement dependent cytotoxicity (CDC), Fc receptor binding, antibody-dependent cell-mediated cytotoxicity (ADCC), antibody-dependent cell-mediated phagocytosis (ADCP), down-regulation of cell surface receptors (e.g., B cell receptor), and B-cell activation. Effector functions may vary with the antibody class. For example, native human IgG1 and IgG3 antibodies can elicit ADCC and CDC activities upon binding to an appropriate Fc receptor present on an immune system cell; and native human IgG1, IgG2, IgG3, and IgG4 can elicit ADCP functions upon binding to the appropriate Fc receptor present on an immune cell.

In some embodiments, one or both Fc polypeptides present in a fusion protein described herein may also be engineered to contain other modifications for heterodimerization, e.g., electrostatic engineering of contact residues within a CH3-CH3 interface that are naturally charged or hydrophobic patch modifications.

In some embodiments, one or both Fc polypeptides present in a fusion protein described herein may include additional modifications that modulate effector function.

In some embodiments, one or both Fc polypeptides present in a fusion protein described herein may comprise modifications that reduce or eliminate effector function. In certain embodiments, one or both Fc polypeptides (e.g., both) do not have effector function. In some embodiments, one or both Fc polypeptides comprise modifications that reduce effector function. Illustrative Fc polypeptide mutations that reduce effector function include, but are not limited to, substitutions in a CH2 domain, e.g., at positions 234 and 235, according to the EU numbering scheme. For example, in some embodiments, one or both Fc polypeptides can comprise alanine residues at positions 234 and 235. Thus, one or both Fc polypeptides may have L234A and L235A (LALA) substitutions.

Additional Fc polypeptide mutations that modulate an effector function include, but are not limited to, the following: position 329 may have a mutation in which proline is substituted with a glycine, serine or arginine or an amino acid residue large enough to destroy the Fc/Fcγ receptor interface that is formed between proline 329 of the Fc and tryptophan residues Trp 87 and Trp 110 of FcγRIII. Additional illustrative substitutions include S228P, E233P, L235E, N297A, N297D, and P331S, according to the EU numbering scheme. Multiple substitutions may also be present, e.g., L234A and L235A of a human IgG1 Fc region; L234A, L235A, and P329G of a human IgG1 Fc region; L234A, L235A, and P329S of a human IgG1 Fc region; S228P and L235E of a human IgG4 Fc region; L234A and G237A of a human IgG1 Fc region; L234A, L235A, and G237A of a human IgG1 Fc region; V234A and G237A of a human IgG2 Fc region; L235A, G237A, and E318A of a human IgG4 Fc region; and S228P and L236E of a human IgG4 Fc region, according to the EU numbering scheme. In some embodiments, one or both Fc polypeptides may have one or more amino acid substitutions that modulate ADCC, e.g., substitutions at positions 298, 333, and/or 334, according to the EU numbering scheme.

In certain embodiments, one or both Fc polypeptides comprise the substitutions of Ala at position 234 and Ala at position 235; Ala at position 234, Ala at position 235 and Gly at position 329; or Ala at position 234, Ala at position 235 and Ser at position 329, according to EU numbering.

In some embodiments, the C-terminal Lys residue is removed in an Fc polypeptide described herein (i.e., the Lys residue at position 447, according to the EU numbering scheme).

Illustrative Fc Polypeptides Comprising Additional Mutations

As described herein, and by way of non-limiting example, one or both Fc polypeptides present in a fusion protein described herein may comprise additional mutations, including: a knob mutation (e.g., T366W as numbered according to the EU numbering scheme), hole mutations (e.g., T366S, L368A, and Y407V as numbered according to the EU numbering scheme), mutations that modulate effector function (e.g., L234A, L235A, and/or P329G or P329S (e.g., L234A and L235A; L234A, L235A, and P329G; or L234A, L235A, and P329S) as numbered according to the EU numbering scheme), and/or mutations that increase serum stability or serum half-life (e.g., (i) M252Y, S254T, and T256E as numbered with reference to EU numbering, or (ii) N434S with or without M428L as numbered according to the EU numbering scheme). By way of illustration, SEQ ID NOs:9-26 and 29-44 provide non-limiting examples of modified Fc polypeptides comprising one or more of these additional mutations.

In some embodiments, an Fc polypeptide or a modified Fc polypeptide may have a knob mutation (e.g., T366W as numbered according to the EU numbering scheme) and at least 85% identity, at least 90% identity, at least 95% identity, at least 96% identity, at least 97% identity, at least 98% identity, or at least 99% identity to the sequence of any one of SEQ ID NOs:1, 2, 27 and 28. In some embodiments, an Fc polypeptide or modified Fc polypeptide having the sequence of any one of SEQ ID NOs: 1, 2, 27 and 28 may be modified to have a knob mutation.

In some embodiments, a modified Fc polypeptide comprises a knob mutation (e.g., T366W as numbered with reference to EU numbering) and has at least 85% identity, at least 90% identity, at least 95% identity, at least 96% identity, at least 97% identity, at least 98% identity, or at least 99% identity to the sequence of any one of SEQ ID NOs: 17 and 18. In some embodiments, the modified Fc polypeptide comprises the sequence of any one of SEQ ID NOs: 17 and 18.

In some embodiments, a modified Fc polypeptide comprises a knob mutation (e.g., T366W as numbered with reference to EU numbering) and has at least 85% identity, at least 90% identity, at least 95% identity, at least 96% identity, at least 97% identity, at least 98% identity, or at least 99% identity to the sequence of any one of SEQ ID NOs: 29 and 30. In some embodiments, a modified Fc polypeptide comprises a knob mutation (e.g., T366W as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 29 and 30, and comprises Ala at position 389, according to EU numbering. In some embodiments, a modified Fc polypeptide comprises a knob mutation (e.g., T366W as numbered with reference to EU numbering), has at least 85% identity, at least 90% identity, at least 95% identity, at least 96% identity, at least 97% identity, at least 98% identity, or at least 99% identity to SEQ ID NO:29 or 30, and comprises at the following positions, according to EU numbering: Glu at position 380; Ala at position 389; and Asn at position 390. In some embodiments, a modified Fc polypeptide comprises a knob mutation (e.g., T366W as numbered with reference to EU numbering), has at least 85% identity, at least 90% identity, at least 95% identity, at least 96% identity, at least 97% identity, at least 98% identity, or at least 99% identity to SEQ ID NO:29 or 30, and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some embodiments, the modified Fc polypeptide comprises the sequence of any one of SEQ ID NOs: 29 and 30.

In some embodiments, an Fc polypeptide or a modified Fc polypeptide may have a knob mutation (e.g., T366W as numbered according to the EU numbering scheme), mutations that modulate effector function (e.g., L234A, L235A, and/or P329G or P329S (e.g., L234A and L235A; L234A, L235A, and P329G; or L234A, L235A, and P329S)) as numbered according to the EU numbering scheme), and at least 85% identity, at least 90% identity, at least 95% identity, at least 96% identity, at least 97% identity, at least 98% identity, or at least 99% identity to the sequence of any one of SEQ ID NOs: 1, 2, 27, and 28. In some embodiments, an Fc polypeptide or a modified Fc polypeptide having the sequence of any one of SEQ ID NOs: 1, 2, 27, and 28 may be modified to have a knob mutation and mutations that modulate effector function.

In some embodiments, a modified Fc polypeptide comprises a knob mutation (e.g., T366W as numbered with reference to EU numbering) and mutations that modulate effector function (e.g., L234A, L235A, and/or P329G or P329S (e.g., L234A and L235A; L234A, L235A, and P329G; or L234A, L235A, and P329S)) as numbered with reference to EU numbering), and has at least 85% identity, at least 90% identity, at least 95% identity, at least 96% identity, at least 97% identity, at least 98% identity, or at least 99% identity to the sequence of any one of SEQ ID NOs:19-20 and 25-26. In some embodiments, the modified Fc polypeptide comprises the sequence of any one of SEQ ID NOs: 19-20 and 25-26.

In some embodiments, a modified Fc polypeptide comprises a knob mutation (e.g., T366W as numbered with reference to EU numbering) and mutations that modulate effector function (e.g., L234A, L235A, and/or P329G or P329S (e.g., L234A and L235A; L234A, L235A, and P329G; or L234A, L235A, and P329S) as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 31-36 and 41-44. In some embodiments, a modified Fc polypeptide comprises a knob mutation (e.g., T366W as numbered with reference to EU numbering) and mutations that modulate effector function (e.g., L234A, L235A, and/or P329G or P329S (e.g., L234A and L235A; L234A, L235A, and P329G; or L234A, L235A, and P329S) as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 31-36 and 41-44, and comprises Ala at position 389, according to EU numbering. In some embodiments, a modified Fc polypeptide comprises a knob mutation (e.g., T366W as numbered with reference to EU numbering) and mutations that modulate effector function (e.g., L234A, L235A, and/or P329G or P329S (e.g., L234A and L235A; L234A, L235A, and P329G; or L234A, L235A, and P329S) as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 31-36 and 41-44 and comprises at the following positions, according to EU numbering: Glu at position 380; Ala at position 389; and Asn at position 390. In some embodiments, a modified Fc polypeptide comprises a knob mutation (e.g., T366W as numbered with reference to EU numbering) and mutations that modulate effector function (e.g., L234A, L235A, and/or P329G or P329S (e.g., L234A and L235A; L234A, L235A, and P329G; or L234A, L235A, and P329S) as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 31-36 and 41-44 and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some embodiments, the modified Fc polypeptide comprises the sequence of any one of SEQ ID NOs: 31-36 and 41-44.

In some embodiments, an Fc polypeptide or a modified Fc polypeptide may have hole mutations (e.g., T366S, L368A, and Y407V as numbered according to the EU numbering scheme) and at least 85% identity, at least 90% identity, at least 95% identity, at least 96% identity, at least 97% identity, at least 98% identity, or at least 99% identity to the sequence of any one of SEQ ID NOs: 1, 2, 27 and 28. In some embodiments, an Fc polypeptide or a modified Fc polypeptide having the sequence of any one of SEQ ID NOs: 1, 2, 27, and 28 may be modified to have hole mutations.

In some embodiments, a modified Fc polypeptide comprises hole mutations (e.g., T366S, L368A, and Y407V as numbered with reference to EU numbering) and has at least 85% identity, at least 90% identity, at least 95% identity, at least 96% identity, at least 97% identity, at least 98% identity, or at least 99% identity to the sequence of any one of SEQ ID NOs: 9 and 10. In some embodiments, the modified Fc polypeptide comprises the sequence of any one of SEQ ID NOs: 9 and 10.

In some embodiments, a modified Fc polypeptide comprises hole mutations (e.g., T366S, L368A, and Y407V as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 37 and 38. In some embodiments, a modified Fc polypeptide comprises hole mutations (e.g., T366S, L368A, and Y407V as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 37 and 38, and comprises Ala at position 389, according to EU numbering. In some embodiments, a modified Fc polypeptide comprises hole mutations (e.g., T366S, L368A, and Y407V as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 37 and 38 and comprises at the following positions, according to EU numbering: Glu at position 380; Ala at position 389; and Asn at position 390. In some embodiments, a modified Fc polypeptide comprises hole mutations (e.g., T366S, L368A, and Y407V as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 37 and 38 and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some embodiments, the modified Fc polypeptide comprises the sequence of any one of SEQ ID NOs: 37 and 38.

In some embodiments, an Fc polypeptide or a modified Fc polypeptide may have hole mutations (e.g., T366S, L368A, and Y407V as numbered according to the EU numbering scheme), mutations that modulate effector function (e.g., L234A, L235A, and/or P329G or P329S (e.g., L234A and L235A; L234A, L235A, and P329G; or L234A, L235A, and P329S)) as numbered according to the EU numbering scheme), and at least 85% identity, at least 90% identity, at least 95% identity, at least 96% identity, at least 97% identity, at least 98% identity, or at least 99% identity to the sequence of any one of SEQ ID NOs: 1, 2, 27 and 28. In some embodiments, an Fc polypeptide or a modified Fc polypeptide having the sequence of any one of SEQ ID NOs: 1, 2, 27, and 28 may be modified to have hole mutations and mutations that modulate effector function.

In some embodiments, a modified Fc polypeptide comprises hole mutations (e.g., T366S, L368A, and Y407V as numbered with reference to EU numbering) and mutations that modulate effector function (e.g., L234A, L235A, and/or P329G or P329S (e.g., L234A and L235A; L234A, L235A, and P329G; or L234A, L235A, and P329S)) as numbered with reference to EU numbering), and has at least 85% identity, at least 90% identity, at least 95% identity, at least 96% identity, at least 97% identity, at least 98% identity, or at least 99% identity to the sequence of any one of SEQ ID NOs: 11-16 and 21-24. In some embodiments, the modified Fc polypeptide comprises the sequence of any one of SEQ ID NOs: 11-16 and 21-24.

In some embodiments, a modified Fc polypeptide comprises hole mutations (e.g., T366S, L368A, and Y407V as numbered with reference to EU numbering) and mutations that modulate effector function (e.g., L234A, L235A, and/or P329G or P329S (e.g., L234A and L235A; L234A, L235A, and P329G; or L234A, L235A, and P329S)) as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 39-40. In some embodiments, a modified Fc polypeptide comprises hole mutations (e.g., T366S, L368A, and Y407V as numbered with reference to EU numbering) and mutations that modulate effector function (e.g., L234A, L235A, and/or P329G or P329S (e.g., L234A and L235A; L234A, L235A, and P329G; or L234A, L235A, and P329S)) as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 39-40, and comprises Ala at position 389, according to EU numbering. In some embodiments, a modified Fc polypeptide comprises hole mutations (e.g., T366S, L368A, and Y407V as numbered with reference to EU numbering) and mutations that modulate effector function (e.g., L234A, L235A, and/or P329G or P329S (e.g., L234A and L235A; L234A, L235A, and P329G; or L234A, L235A, and P329S)) as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 39-40 and comprises at the following positions, according to EU numbering: Glu at position 380; Ala at position 389; and Asn at position 390. In some embodiments, a modified Fc polypeptide comprises hole mutations (e.g., T366S, L368A, and Y407V as numbered with reference to EU numbering) and mutations that modulate effector function (e.g., L234A, L235A, and/or P329G or P329S (e.g., L234A and L235A; L234A, L235A, and P329G; or L234A, L235A, and P329S)) as numbered with reference to EU numbering), has at least 85% identity, at least 90% identity, at least 95% identity, at least 96% identity, at least 97% identity, at least 98% identity, or at least 99% identity to the sequence of any one of SEQ ID NOs: 39-40 and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some embodiments, the modified Fc polypeptide comprises the sequence of any one of SEQ ID NOs: 39-40.

FcRn Binding Sites

In certain aspects, modified (e.g., BBB receptor-binding) Fc polypeptides, or Fc polypeptides present in a fusion protein described herein that do not specifically bind to a BBB receptor, can comprise an FcRn binding site. In some embodiments, the FcRn binding site is within the Fc polypeptide or a fragment thereof.

In some embodiments, the FcRn binding site comprises a native FcRn binding site. In some embodiments, the FcRn binding site does not comprise amino acid changes relative to the amino acid sequence of a native FcRn binding site. In some embodiments, the native FcRn binding site is an IgG binding site, e.g., a human IgG binding site. In some embodiments, the FcRn binding site comprises a modification that alters FcRn binding.

In some embodiments, an FcRn binding site has one or more amino acid residues that are mutated, e.g., substituted, wherein the mutation(s) increase serum half-life or do not substantially reduce serum half-life (i.e., reduce serum half-life by no more than 25% compared to a counterpart modified Fc polypeptide having the wild-type residues at the mutated positions when assayed under the same conditions). In some embodiments, an FcRn binding site has one or more amino acid residues that are substituted at positions 250-256, 307, 380, 428, and 433-436, according to the EU numbering scheme.

In some embodiments, one or more residues at or near an FcRn binding site are mutated, relative to a native human IgG sequence, to extend serum half-life of the modified polypeptide. In some embodiments, mutations are introduced into one, two, or three of positions 252, 254, and 256. In some embodiments, the mutations are M252Y, S254T, and T256E. In some embodiments, a modified Fc polypeptide further comprises the mutations M252Y, S254T, and T256E. In some embodiments, a modified Fc polypeptide comprises a substitution at one, two, or all three of positions T307, E380, and N434, according to the EU numbering scheme. In some embodiments, the mutations are T307Q and N434A. In some embodiments, a modified Fc polypeptide comprises mutations T307A, E380A, and N434A. In some embodiments, a modified Fc polypeptide comprises substitutions at positions T250 and M428, according to the EU numbering scheme. In some embodiments, the modified Fc polypeptide comprises mutations T250Q and/or M428L. In some embodiments, a modified Fc polypeptide comprises substitutions at positions M428 and N434, according to the EU numbering scheme. In some embodiments, the modified Fc polypeptide comprises mutations M428L and N434S. In some embodiments, a modified Fc polypeptide comprises an N434S or N434A mutation.

GAA Enzymes Linked to Fc Polypeptides

In some embodiments, a fusion protein described herein comprises two Fc polypeptides as described herein and one or both of the Fc polypeptides may further comprise a partial or full hinge region. The hinge region can be from any immunoglobulin subclass or isotype. An illustrative immunoglobulin hinge is an IgG hinge region, such as an IgG1 hinge region, e.g., human IgG1 hinge amino acid sequence EPKSCDKTHTCPPCP (SEQ ID NO:5) or a portion thereof (e.g., DKTHTCPPCP; SEQ ID NO:6). In some embodiments, the hinge region is at the N-terminal region of the Fc polypeptide.

In some embodiments, the first Fc polypeptide is linked to a first GAA enzyme (e.g., a wild-type GAA enzyme, a GAA enzyme variant, or a catalytically active fragment of a GAA wild-type enzyme or GAA enzyme variant). For example, in certain embodiments, the N-terminus of the first Fc polypeptide is linked to the GAA enzyme. In certain embodiments, the C-terminus of the first Fc polypeptide is linked to the GAA enzyme.

In certain embodiments, a fusion protein described herein comprises a single GAA enzyme.

In some embodiments, a fusion protein as described herein comprises a second GAA enzyme, which may be the same or different from the first GAA enzyme (e.g., a wild-type GAA enzyme, a GAA enzyme variant, or a catalytically active fragment of a GAA wild-type enzyme or GAA enzyme variant). For example, in certain embodiments, the second Fc polypeptide is linked to a GAA enzyme. In certain embodiments, the N-terminus of the second Fc polypeptide is linked to the second GAA enzyme. In certain embodiments, the C-terminus of the second Fc polypeptide is linked to the second GAA enzyme.

In certain embodiments, the N-terminus of the first Fc polypeptide is linked to a first GAA enzyme; and the N-terminus of the second Fc polypeptide is linked to a second GAA enzyme.

In certain embodiments, the C-terminus of the first Fc polypeptide is linked to a first GAA enzyme; and the C-terminus of the second Fc polypeptide is linked to a second GAA enzyme.

In certain embodiments, the N-terminus of the first Fc polypeptide is linked to a first GAA enzyme; and the C-terminus of the second Fc polypeptide is linked to a second GAA enzyme.

In certain embodiments, the C-terminus of the first Fc polypeptide is linked to a first GAA enzyme; and the N-terminus of the second Fc polypeptide is linked to a second GAA enzyme.

In some embodiments, an Fc polypeptide (e.g., the first Fc polypeptide) is joined to a GAA enzyme by a linker, e.g., a peptide linker or polypeptide linker. In some embodiments, the Fc polypeptide (e.g., the first Fc polypeptide) is joined to the GAA enzyme by a peptide bond or by a peptide linker/polypeptide linker, e.g., is a fusion polypeptide. The linker may be configured such that it allows for the rotation of the GAA enzyme relative to the Fc polypeptide to which it is joined; and/or is resistant to digestion by proteases. Peptide/polypeptide linkers may contain natural amino acids, unnatural amino acids, or a combination thereof. In some embodiments, the peptide/polypeptide linker may be a flexible linker, e.g., containing amino acids such as Gly, Asn, Ser, Thr, Ala, and the like (e.g., a glycine-rich linker). Such linkers are designed using known parameters and may be of any length and contain any number of repeat units of any length (e.g., repeat units of Gly and Ser residues). For example, the linker may have repeats, such as two, three, four, five, or more $Gly_4$-Ser (SEQ ID NO:62) repeats or a single $Gly_4$-Ser (SEQ ID NO:62). In other aspects, the linker may be Gly-Ser. In some embodiments, the linker may include a protease cleavage site, e.g., that is cleavable by an enzyme present in the central nervous system.

In some embodiments, the GAA enzyme is joined to the Fc polypeptide by a Gly-Ser linker, a $Gly_4$-Ser linker (SEQ ID NO:62) or a $(Gly_4$-Ser$)_2$ linker (SEQ ID NO:63). In some embodiments, the Fc polypeptide may comprise a hinge sequence or partial hinge sequence at the N-terminus that is joined to the linker or that is directly joined to the GAA enzyme.

In some embodiments, the GAA enzyme is joined to the N-terminus of the Fc polypeptide, e.g., by a Gly-Ser linker, a $Gly_4$-Ser linker (SEQ ID NO:62) or a $(Gly_4$-Ser$)_2$ linker (SEQ ID NO:63). In some embodiments, the Fc polypeptide may comprise a hinge sequence or partial hinge sequence at the N-terminus that is joined to the linker or that is directly joined to the GAA enzyme.

In some embodiments, the GAA enzyme is joined to the C-terminus of the Fc polypeptide, e.g., by a Gly-Ser linker, a $Gly_4$-Ser linker (SEQ ID NO:62) or a $(Gly_4$-Ser$)_2$ linker (SEQ ID NO:63). In some embodiments, the C-terminus of the Fc polypeptide is directly joined to the GAA enzyme.

In some embodiments, the GAA enzyme is joined to the Fc polypeptide by a chemical cross-linking agent. Such conjugates can be generated using well-known chemical cross-linking reagents and protocols. For example, there are a large number of chemical cross-linking agents that are known to those skilled in the art and useful for cross-linking the polypeptide with an agent of interest. For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including N-hydroxysuccinimide (NHS) or its water soluble analog N-hydroxysulfosuccinimide (sulfo-NHS), succinimidyl 4-(N-maleimidomethyl)cyclohexane-1-carboxylate (SMCC), m-maleimidobenzoyl-N-hydroxysuccinimide ester (MBS); N-succinimidyl (4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-toluene (SMPT), N-succinimidyl 3-(2-pyridyldithio)propionate (SPDP), and succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exist a number of other cross-linking agents including homobifunctional and photoreactive cross-linkers. Disuccinimidyl subcrate (DSS), bismaleimidohexane (BMH) and dimethylpimelimidate. 2HCl (DMP) are examples of useful homobifunctional cross-linking agents, and bis-[B-(4-azidosalicylamido) ethyl]disulfide (BASED) and N-succinimidyl-6(4'-azido-2'-nitrophenylamino)hexanoate (SANPAH) are examples of useful photoreactive cross-linkers.

Illustrative Protein Molecules Comprising GAA Enzyme-Fc Fusion Polypeptides

In some aspects, a fusion protein described herein comprises a first Fc polypeptide that is linked to a GAA enzyme (e.g., a wild-type GAA enzyme, a GAA enzyme variant or a catalytically active fragment of a wild-type GAA enzyme or GAA enzyme variant); and a second Fc polypeptide; wherein the first and/or second Fc polypeptide is a modified Fc that is capable of binding (e.g., specifically binding) to a blood-brain barrier (BBB) receptor, e.g., a transferrin receptor (TfR). In certain embodiments, the second Fc polypeptide forms an Fc dimer with the first Fc polypeptide. In some embodiments, the first Fc polypeptide and/or the second Fc polypeptide does not include an immunoglobulin heavy and/or light chain variable region sequence or an antigen-binding portion thereof. In some embodiments, the fusion protein does not include an immunoglobulin heavy and/or light chain variable region sequence or an antigen-binding portion thereof. In certain embodiments, a fusion protein described herein comprises a single GAA enzyme. In some other aspects, the fusion protein further comprises a second, independently selected, GAA enzyme (e.g., which may be linked to the second Fc polypeptide).

In some embodiments, the first Fc polypeptide is a modified Fc polypeptide and/or the second Fc polypeptide is a modified Fc polypeptide (e.g., comprises one or more modifications described herein). For example, in some embodiments, a modified Fc polypeptide contains one or more modifications that promote its heterodimerization to the other Fc polypeptide. In some embodiments, a modified Fc polypeptide contains one or more modifications that reduce effector function. In some embodiments, a modified Fc polypeptide contains one or more modifications that extend serum half-life. In some embodiments, a modified Fc polypeptide comprises one or more modifications that confer binding BBB) receptor, e.g., transferrin receptor (TfR). For example, in certain embodiments, an Fc polypeptide that is capable of binding to a TfR comprises Ala at position 389, according to EU numbering. In some embodiments, an Fc polypeptide that is capable of binding to a TfR receptor comprises at the following positions, according to EU numbering: Glu at position 380; Ala at position 389; and Asn at position 390. In some embodiments, an Fc polypeptide that is capable of binding to a TfR receptor comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some embodiments, such an Fc polypeptide specifically binds to TfR.

In some embodiments, the first Fc polypeptide is a modified Fc polypeptide. In some embodiments, the second Fc polypeptide is a modified Fc polypeptide. In some embodiments, the first and the second Fc polypeptide are each a modified Fc polypeptide. In some embodiments, the first Fc polypeptide is a modified polypeptide but does not specifically bind to TfR; and the second Fc polypeptide is a modified polypeptide that is capable of specifically binding to TfR, and optionally, further comprises one or more further modifications described herein. In other embodiments, the first Fc polypeptide is a modified polypeptide that is capable of specifically binding to TfR, and optionally, further comprises one or more further modifications described herein; and the second Fc polypeptide is a modified polypeptide but does not specifically binding to TfR. In some embodiments, the first Fc polypeptide is a modified polypeptide that is capable of specifically binding to TfR, and optionally, further comprises one or more further modifications described herein; and the second Fc polypeptide is a modified polypeptide that is capable of specifically binding to TfR, and optionally, further comprises one or more further modifications described herein.

In some embodiments, a fusion protein described herein comprises a first polypeptide chain that comprises a first Fc polypeptide comprising T366S, L368A, and Y407V (hole) substitutions linked to a GAA enzyme; and a second polypeptide chain that comprises a second Fc polypeptide that comprises a T366W (knob) substitution, wherein the first and/or second Fc polypeptide is a modified polypeptide that is capable of binding to TfR. In some embodiments, the first Fc polypeptide and/or the second Fc polypeptide further comprises L234A and L235A (LALA) substitutions. In some embodiments, the first Fc polypeptide and/or the second Fc polypeptide further comprises L234A, L235A, and P329G (LALAPG) substitutions or further comprises L234A, L235A, and P329S (LALAPS) substitutions. In some embodiments, the first Fc polypeptide and/or the second Fc polypeptide further comprises M252Y, S254T, and T256E (YTE) substitutions. In some embodiments, the first Fc polypeptide and/or the second Fc polypeptide further comprises: 1) L234A and L235A (LALA) substitutions; L234A, L235A, and P329G (LALAPG) substitutions; or L234A, L235A, and P329S (LALAPS) substitutions; and 2) M252Y, S254T, and T256E (YTE) substitutions. In some embodiments, the first Fc polypeptide and/or the second Fc polypeptide comprises human IgG1 wild-type residues at positions 234, 235, 252, 254, 256, and 366.

In some embodiments, the second Fc polypeptide is a modified polypeptide that is capable of binding to TfR. In some embodiments, the first Fc polypeptide linked to a GAA enzyme is not modified to bind to TfR. In some embodiments, the second Fc polypeptide comprises the knob, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:29-36. In some embodiments, the second Fc polypeptide comprises the knob, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:29-36, and comprises Ala at position 389, according to EU numbering. In some embodiments, the second Fc polypeptide has at least 85% identity, at least 90% identity, at least 95% identity, at least 96% identity, at least 97% identity, at least 98% identity, or at least 99% identity to the sequence of any one of SEQ ID NOs: 29-36 and comprises at the following positions, according to EU numbering: Glu at position 380; Ala at position 389; and Asn at position 390. In some embodiments, the second Fc polypeptide has at least 85% identity, at least 90% identity, at least 95% identity, at least 96% identity, at least 97% identity, at least 98% identity, or at least 99% identity to the sequence of any one of SEQ ID NOs: 29-36 and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421; or comprises the sequence of any one of SEQ ID NOs: 29-36. In some embodiments, the first Fc polypeptide comprises the hole, LALA/LALAPG/LALAPS, and/or YTE mutations, and has at least 85% identity, at least 90% identity, at least 95% identity, at least 96% identity, at least 97% identity, at least 98% identity, or at least 99% identity to any one of SEQ ID NOs:9-16; or comprises the sequence of any one of SEQ ID NOs:9-16. In some embodiments, the second Fc polypeptide comprises any one of SEQ ID NOs:29-36, and the first Fc polypeptide comprises any one of SEQ ID NOs:9-16. In some embodiments, the N-terminus of the first Fc polypeptide and/or the second Fc polypeptide includes a portion of an IgG1 hinge region (e.g., DKTHTCPPCP; SEQ ID NO:6). In some embodiments, the second Fc polypeptide has at least 85%, at least 90%, at least 95% identity, at least 96% identity, at least 97% identity, at least 98% identity, or at least 99% identity to any one of SEQ ID NOs: 41-44. In some embodiments, the second Fc polypeptide has at least 85%, at least 90%, at least 95% identity, at least 96% identity, at least 97% identity, at least 98% identity, or at least 99% identity to any one of SEQ ID NOs: 41-44, and comprises Ala at position 389, according to EU numbering. In some embodiments, the second Fc polypeptide has at least 85% identity, at least 90% identity, at least 95% identity, at least 96% identity, at least 97% identity, at least 98% identity, or at least 99% identity to the sequence of any one of SEQ ID NOs: 41-44 and comprises at the following positions, according to EU numbering: Glu at position 380; Ala at position 389; and Asn at position 390. In some embodiments, the second Fc polypeptide has at least 85% identity, at least 90% identity, at least 95% identity, at least 96% identity, at least 97% identity, at least 98% identity, or at least 99% identity to the sequence of any one of SEQ ID NOs: 41-44 and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421, or comprises the sequence of any one of SEQ ID NOs:41-44. In some embodiments, the first Fc polypeptide has at least 85%, at least 90%, at least 95% identity, at least 96% identity, at least 97% identity, at least 98% identity, or at least 99% identity to any one of SEQ ID NOs: 21-24, or comprises the sequence of any one of SEQ ID NOs:21-24.

In some embodiments, the second Fc polypeptide is not modified to bind to TfR. In some embodiments, the first Fc polypeptide linked to a GAA enzyme is a modified polypeptide that is capable of binding to TfR. In some embodiments, the second Fc polypeptide comprises the knob, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:17-20; or comprises the sequence of any one of SEQ ID NOs: 17-20. In some embodiments, the first Fc polypeptide comprises the hole, LALA/LALAPG/LALAPS, and/or YTE mutations, and has at least 85% identity, at least 90% identity, at least 95% identity, at least 96% identity, at least 97% identity, at least 98% identity or at least 99% identity to any one of SEQ ID NOs:37-40. In some embodiments, the first Fc polypeptide comprises the hole, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:37-40, and comprises Ala at position 389, according to EU numbering. In some embodiments, the first Fc polypeptide comprises the hole, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:37-40, and comprises at the following positions, according to EU numbering: Glu at position 380; Ala at position 389; and Asn at position 390. In some embodiments, the first Fc polypeptide comprises the hole, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:37-40, and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421, or comprises the sequence of any one of SEQ ID NOs: 37-40. In some embodiments, the second Fc polypeptide comprises any one of SEQ ID NOs:17-20, and the first Fc polypeptide comprises any one of SEQ ID NOs: 37-40. In some embodiments, the N-terminus of the first Fc polypeptide and/or the second Fc polypeptide includes a portion of an IgG1 hinge region (e.g., DKTH-TCPPCP; SEQ ID NO:6). In some embodiments, the second Fc polypeptide has at least 85%, at least 90%, at least 95% identity, at least 96% identity, at least 97% identity, at least 98% identity, or at least 99% identity to any one of SEQ ID NOs: 25-26; or comprises the sequence of any one of SEQ ID NOs:25-26.

In some embodiments, a fusion protein described herein comprises a first polypeptide chain that comprises a first Fc polypeptide comprising a T366W (knob) substitution linked to a GAA enzyme; and a second polypeptide chain that comprises a second Fc polypeptide that comprises T366S, L368A, and Y407V (hole) substitutions, wherein the first and/or second Fc polypeptide is a modified polypeptide that is capable of binding to TfR. In some embodiments, the first Fc polypeptide and/or the second Fc polypeptide further comprises L234A and L235A (LALA) substitutions. In some embodiments, the first Fc polypeptide and/or the second Fc polypeptide further comprises L234A, L235A, and P329G (LALAPG) substitutions or further comprises L234A, L235A, and P329S (LALAPS) substitutions. In some embodiments, the first Fc polypeptide and/or the second Fc polypeptide further comprises M252Y, S254T, and T256E (YTE) substitutions. In some embodiments, the first Fc polypeptide and/or the second Fc polypeptide further comprises: 1) L234A and L235A (LALA) substitutions; L234A, L235A, and P329G (LALAPG) substitutions; or L234A, L235A, and P329S (LALAPS) substitutions; and 2) M252Y, S254T, and T256E (YTE) substitutions. In some embodiments, the first Fc polypeptide and/or the second Fc polypeptide comprises human IgG1 wild-type residues at positions 234, 235, 252, 254, 256, and 366.

In some embodiments, the second Fc polypeptide is a modified polypeptide that is capable of binding to TfR. In some embodiments, the first Fc polypeptide linked to a GAA enzyme is not modified to bind to TfR. In some embodiments, the second Fc polypeptide comprises the hole, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:37-40. In some embodiments, the second Fc polypeptide comprises the hole, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:37-40, and comprises Ala at position 389, according to EU numbering. In some of the foregoing embodiments, the second Fc polypeptide further comprises at the following positions, according to EU numbering: Glu at position 380 and Asn at position 390. In some of the foregoing embodiments, the second Fc polypeptide comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some embodiments, the second Fc polypeptide comprises the sequence of any one of SEQ ID NOs:37-40. In some embodiments, the first Fc polypeptide comprises the knob, LALA/LALAPG/LALAPS, and/or YTE mutations and has at least 85% identity, at least 90% identity, at least 95% identity, at least 96% identity, at least 97% identity, at least 98% identity, or at least 99% identity to any one of SEQ ID NOs:17-20; or comprises the sequence of any one of SEQ ID NOs: 17-20. In some embodiments, the second Fc polypeptide comprises any one of SEQ ID NOs: 37-40, and the first Fc polypeptide comprises any one of SEQ ID NOs:17-20. In some embodiments, the N-terminus of the first Fc polypeptide and/or the second Fc polypeptide includes a portion of an IgG1 hinge region (e.g., DKTHTCPPCP; SEQ ID NO:6). In some embodiments, the first Fc polypeptide has at least 85%, at least 90%, at least 95% identity, at least 96% identity, at least 97% identity, at least 98% identity, or at least 99% identity to any one of SEQ ID NOs: 25-26, or comprises the sequence of any one of SEQ ID NOs:25-26.

In some embodiments, the second Fc polypeptide is not modified to bind to TfR. In some embodiments, the first Fc polypeptide linked to a GAA enzyme is a modified polypeptide that is capable of binding to TfR. In some embodiments, the second Fc polypeptide comprises the hole, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:9-16; or comprises the sequence of any one of SEQ ID NOs: 9-16. In some embodiments, the first Fc polypeptide comprises the knob, LALA/LALAPG/LALAPS, and/or YTE mutations, and has at least 85% identity, at least 90% identity, at least 95% identity, at least 96% identity, at least 97% identity, at least 98% identity, or at least 99% identity to any one of SEQ ID NOs:29-36. In some embodiments, the first Fc polypeptide comprises the knob, LALA/LALAPG/LALAPS, and/or YTE mutations, has at least 85% identity, at least 90% identity, at least 95% identity, at least 96% identity, at least 97% identity, at least 98% identity, or at least 99% identity to any one of SEQ ID NOs:29-36, and comprises Ala at position 389, according to EU numbering. In some of the foregoing embodiments, the first Fc polypeptide further comprises at the following positions, according to EU numbering: Glu at position 380 and Asn at position 390. In some of the foregoing embodiments, the first Fc polypeptide comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some embodiments, the first Fc polypeptide comprises the sequence of any one of SEQ ID NOs: 29-36. In some embodiments, the second Fc polypeptide comprises any one of SEQ ID NOs:9-16, and the first Fc polypeptide comprises any one of SEQ ID NOs: 29-36. In some embodiments, the N-terminus of the first Fc polypeptide and/or the second Fc polypeptide includes a portion of an IgG1 hinge region (e.g., DKTHTCPPCP; SEQ ID NO:6). In some embodiments, the second Fc polypeptide has at least 85%, at least 90%, at least 95% identity, at least 96% identity, at least 97% identity, at least 98% identity, or at least 99% identity to any one of SEQ ID NOs: 21-24; or comprises the sequence of any one of SEQ ID NOs:21-24. In some embodiments, the first Fc polypeptide has at least 85%, at least 90%, at least 95% identity, at least 96% identity, at least 97% identity, at least 98% identity, or at least 99% identity to any one of SEQ ID NOs: 41-44; or comprises the sequence of any one of SEQ ID NOs:41-44.

In some embodiments, a GAA enzyme (e.g., a wild-type GAA enzyme, a GAA enzyme variant, or a catalytically active fragment of a wild-type GAA enzyme or GAA enzyme variant), present in a fusion protein described herein is linked to a first polypeptide chain that comprises a first Fc polypeptide having at least 85%, at least 90%, at least 95% identity, at least 96% identity, at least 97% identity, at least 98% identity, or at least 99% identity to any one of SEQ ID NOs: 9-16, or comprises the sequence of any one of SEQ ID NOs: 9-16 (e.g., as a fusion polypeptide). In some embodiments, the GAA enzyme is linked to the first Fc polypeptide by a linker, such as a flexible linker, and/or a hinge region or portion thereof (e.g., DKTHTCPPCP; SEQ ID NO:6). In some embodiments, the N-terminus of the first Fc polypeptide includes a portion of an IgG1 hinge region (e.g., DKTHTCPPCP; SEQ ID NO:6). In some embodiments, the first Fc polypeptide has at least 85%, at least 90%, at least 95% identity, at least 96% identity, at least 97% identity, at least 98% identity, or at least 99% identity to any one of SEQ ID NOs:21-24, or comprises the sequence of any one of SEQ ID NOs:21-24. In some embodiments, the GAA enzyme comprises an amino acid sequence having at least 85%, at least 90%, at least 95% identity, at least 96% identity, at least 97% identity, at least 98% identity, or at least 99% identity to any one of SEQ ID NOs:45-47 and 64-66, or comprises the sequence of any one of SEQ ID NOs:45-47 and 64-66. In some embodiments, the GAA enzyme linked to the first Fc polypeptide has at least 85%, at least 90%, at least 95% identity, at least 96% identity, at least 97% identity, at least 98% identity, or at least 99% identity to any one of SEQ ID NOs:48-59 and 67-70, or comprises the sequence of any one of SEQ ID NOs:48-59 and 67-70. In some embodiments, the fusion protein comprises a second Fc polypeptide having at least 85%, at least 90%, at least 95% identity, at least 96% identity, at least 97% identity, at least 98% identity, or at least 99% identity to any one of SEQ ID NOs: 29-36. In some embodiments, the fusion protein comprises a second Fc polypeptide having at least 85%, at least 90%, at least 95% identity, at least 96% identity, at least 97% identity, at least 98% identity, or at least 99% identity to any one of SEQ ID NOs: 29-36, and comprises Ala at position 389, according to EU numbering. In some embodiments, the second Fc polypeptide has at least 85% identity, at least 90% identity, at least 95% identity, at least 96% identity, at least 97% identity, at least 98% identity, or at least 99% identity to the sequence of any one of SEQ ID NOs: 29-36 and comprises at the following positions, according to EU numbering: Glu at position 380; Ala at position 389; and Asn at position 390. In some embodiments, the second polypeptide has at least 85% identity, at least 90% identity, at least 95% identity, at least 96% identity, at least 97% identity, at least 98% identity, or at least 99% identity to the sequence of any one of SEQ ID NOs: 29-36 and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421, or comprises the sequence of any one of SEQ ID NOs: 29-36. In some embodiments, the N-terminus of the second Fc polypeptide includes a portion of an IgG1 hinge region (e.g., DKTHTCPPCP; SEQ ID NO:6). In some embodiments, the second Fc polypeptide has at least 85%, at least 90%, at least 95% identity, at least 96% identity, at least 97% identity, at least 98% identity, or at least 99% identity to any one of SEQ ID NOs:41-44. In some embodiments, the second Fc polypeptide has at least 85%, at least 90%, at least 95% identity, at least 96% identity, at least 97% identity, at least 98% identity, or at least 99% identity to any one of SEQ ID NOs:41-44, and comprises Ala at position 389, according to EU numbering. In some embodiments, the second Fc polypeptide has at least 85% identity, at least 90% identity, at least 95% identity, at least 96% identity, at least 97% identity, at least 98% identity, or at least 99% identity to the sequence of any one of SEQ ID NOs: 41-44 and comprises at the following positions, according to EU numbering: Glu at position 380; Ala at position 389; and Asn at position 390. In some embodiments, the second Fc polypeptide has at least 85% identity, at least 90% identity, at least 95% identity, at least 96% identity, at least 97% identity, at least 98% identity, or at least 99% identity to the sequence of any one of SEQ ID NOs: 41-44 and comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421, or comprises the sequence of any one of SEQ ID NOs:41-44. In some embodiments, a second GAA enzyme is linked to the second Fc polypeptide by a linker, such as a flexible linker, and/or a hinge region or portion thereof (e.g., DKTHTCPPCP; SEQ ID NO:6).

In certain embodiments, the fusion protein comprises a first Fc polypeptide linked to a GAA enzyme comprising an amino acid sequence having at least 95% or 100% identity to any one of SEQ ID NOs: 48-59 and 67-70. In certain embodiments, the fusion protein comprises a second Fc polypeptide comprising an amino acid sequence having at least 95% or 100% identity to any one of SEQ ID NOs: 31-36 and 41-44 (e.g., SEQ ID NOs:41-44). For example, in certain embodiments, the second Fc polypeptide comprises an amino acid sequence having at least 95% or 100% identity to any one of SEQ ID NOs: 31, 32, 41 and 42. In certain embodiments, the second Fc polypeptide comprises an amino acid sequence having at least 95% or 100% identity to any one of SEQ ID NOs:35, 36, 43 and 44. In certain embodiments, the second Fc polypeptide comprises an amino acid sequence having at least 95% or 100% identity to SEQ ID NO: 41. In certain embodiments, the second Fc polypeptide comprises an amino acid sequence having at least 95% or 100% identity to SEQ ID NO: 42. In certain embodiments, the second Fc polypeptide comprises an amino acid sequence having at least 95% or 100% identity to SEQ ID NO: 43. In certain embodiments, the second Fc polypeptide comprises an amino acid sequence having at least 95% or 100% identity to SEQ ID NO: 44.

In certain embodiments, the fusion protein comprises a first Fc polypeptide linked to a GAA amino acid sequence comprising an amino acid sequence having at least 95% or 100% identity to any one of SEQ ID NOs: 48-55. For example, in certain embodiments, the first Fc polypeptide linked to a GAA amino acid sequence comprises an amino acid sequence having at least 95% or 100% identity to any one of SEQ ID NOs: 48-49. In certain embodiments, the first Fc polypeptide linked to a GAA amino acid sequence comprises an amino acid sequence having at least 95% or 100% identity to any one of SEQ ID NOs: 50-51. In certain embodiments, the first Fc polypeptide linked to a GAA amino acid sequence comprises an amino acid sequence having at least 95% or 100% identity to any one of SEQ ID NOs: 52-53. In certain embodiments, the first Fc polypeptide linked to a GAA amino acid sequence comprises an amino acid sequence having at least 95% or 100% identity to any one of SEQ ID NOs:54-55. In certain embodiments, the second Fc polypeptide comprises an amino acid sequence having at least 95% or 100% identity to any one of SEQ ID NOs: 31-36 and 41-44 (e.g., SEQ ID NOs: 41-44). For example, in certain embodiments, the second Fc polypeptide comprises an amino acid sequence having at least 95% or 100% identity to any one of SEQ ID NOs: 31, 32, 41 and 42. In certain embodiments, the second Fc polypeptide comprises an amino acid sequence having at least 95% or 100% identity to any one of SEQ ID NOs:35, 36, 43 and 44. In certain embodiments, the second Fc polypeptide comprises an amino acid sequence having at least 95% or 100% identity to SEQ ID NO: 41. In certain embodiments, the second Fc polypeptide comprises an amino acid sequence having at least 95% or 100% identity to SEQ ID NO: 42. In certain embodiments, the second Fc polypeptide comprises an amino acid sequence having at least 95% or 100% identity to SEQ ID NO: 43. In certain embodiments, the second Fc polypeptide comprises an amino acid sequence having at least 95% or 100% identity to SEQ ID NO: 44.

In some embodiments, the fusion protein comprises a first Fc polypeptide linked to a GAA enzyme comprising an amino acid sequence of any one of SEQ ID NOs: 48-55; and a second Fc polypeptide comprising an amino acid sequence of any one of SEQ ID NOs: 41-44.

In some embodiments, the fusion protein comprises a first Fc polypeptide linked to a GAA enzyme comprising the amino acid sequence of any one of SEQ ID NOs: 48-49; and a second Fc polypeptide comprising the amino acid sequence of any one of SEQ ID NOs: 41-42.

In some embodiments, the fusion protein comprises a first Fc polypeptide linked to a GAA enzyme comprising the amino acid sequence of any one of SEQ ID NOs:50-51, and a second Fc polypeptide comprising the amino acid sequence of any one of SEQ ID NOs:41-42.

In some embodiments, the fusion protein comprises a first Fc polypeptide linked to a GAA enzyme comprising the amino acid sequence of any one of SEQ ID NOs: 52-53; and a second Fc polypeptide comprising the amino acid sequence of any one of SEQ ID NOs: 43-44.

In some embodiments, the fusion protein comprises a first Fc polypeptide linked to a GAA enzyme comprising the amino acid sequence of SEQ ID NO: 53; and a second Fc polypeptide comprising the amino acid sequence of SEQ ID NO: 44.

In some embodiments, the fusion protein comprises a first Fc polypeptide linked to a GAA enzyme comprising the amino acid sequence of any one of SEQ ID NOs:54-55, and a second Fc polypeptide comprising the amino acid sequence of any one of SEQ ID NOs:43-44.

In some embodiments, the fusion protein comprises a first Fc polypeptide linked to a GAA enzyme comprising the amino acid sequence of SEQ ID NO: 55; and a second Fc polypeptide comprising the amino acid sequence of SEQ ID NO: 44.

In some embodiments, the fusion protein comprises a first Fc polypeptide linked to a GAA enzyme comprising an amino acid sequence having at least 95% or 100% identity to any one of SEQ ID NOs: 56-59 and 67-70. For example, in certain embodiments, the first Fc polypeptide linked to a GAA enzyme comprises an amino acid sequence having at least 95% or 100% identity to SEQ ID NO: 56. In certain embodiments, the first Fc polypeptide linked to a GAA enzyme comprises an amino acid sequence having at least 95% or 100% identity to SEQ ID NO: 57. In certain embodiments, the first Fc polypeptide linked to a GAA enzyme comprises an amino acid sequence having at least 95% or 100% identity to SEQ ID NO: 58. In certain embodiments, the first Fc polypeptide linked to a GAA enzyme comprises an amino acid sequence having at least 95% or 100% identity to SEQ ID NO: 59. In certain embodiments, the first Fc polypeptide linked to a GAA enzyme comprises an amino acid sequence having at least 95% or 100% identity to SEQ ID NO: 67. In certain embodiments, the first Fc polypeptide linked to a GAA enzyme comprises an amino acid sequence having at least 95% or 100% identity to SEQ ID NO: 68. In certain embodiments, the first Fc polypeptide linked to a GAA enzyme comprises an amino acid sequence having at least 95% or 100% identity to SEQ ID NO: 69. In certain embodiments, the first Fc polypeptide linked to a GAA enzyme comprises an amino acid sequence having at least 95% or 100% identity to SEQ ID NO: 70. In certain embodiments, the fusion protein comprises a second Fc polypeptide comprising an amino acid sequence having at least 95% or 100% identity to any one of SEQ ID NOs: 31-36 and 41-44 (e.g., SEQ ID NOs:41-44). For example, in certain embodiments, the second Fc polypeptide comprises an amino acid sequence having at least 95% or 100% identity to any one of SEQ ID NOs: 31, 32, 41 and 42. In certain embodiments, the second Fc polypeptide comprises an amino acid sequence having at least 95% or 100% identity to any one of SEQ ID NOs:35, 36, 43 and 44. In certain embodiments, the second Fc polypeptide comprises an amino acid sequence having at least 95% or 100% identity to SEQ ID NO: 41. In certain embodiments, the second Fc polypeptide comprises an amino acid sequence having at least 95% or 100% identity to SEQ ID NO: 42. In certain embodiments, the second Fc polypeptide comprises an amino acid sequence having at least 95% or 100% identity to SEQ ID NO: 43. In certain embodiments, the second Fc polypeptide comprises an amino acid sequence having at least 95% or 100% identity to SEQ ID NO: 44.

In some embodiments, the fusion protein comprises a first Fc polypeptide linked to a GAA enzyme comprising the amino acid sequence of any one of SEQ ID NOs: 56-59 and 67-70 and a second Fc polypeptide comprising the amino acid sequence of any one of SEQ ID NOs: 41-44.

In some embodiments, the fusion protein comprises a first Fc polypeptide linked to a GAA enzyme comprising the amino acid sequence of any one of SEQ ID NOs: 56-57 and 67-68; and a second Fc polypeptide comprising the amino acid sequence of any one of SEQ ID NOs: 41-42.

In some embodiments, the fusion protein comprises a first Fc polypeptide linked to a GAA enzyme comprising the amino acid sequence of SEQ ID NO: 56; and a second Fc polypeptide comprising the amino acid sequence of any one of SEQ ID NOs: 41-42.

In some embodiments, the fusion protein comprises a first Fc polypeptide linked to a GAA enzyme comprising the amino acid sequence of SEQ ID NO: 57; and a second Fc polypeptide comprising the amino acid sequence of any one of SEQ ID NOs: 41-42.

In some embodiments, the fusion protein comprises a first Fc polypeptide linked to a GAA enzyme comprising the amino acid sequence of SEQ ID NO: 67; and a second Fc polypeptide comprising the amino acid sequence of any one of SEQ ID NOs: 41-42.

In some embodiments, the fusion protein comprises a first Fc polypeptide linked to a GAA enzyme comprising the amino acid sequence of SEQ ID NO: 68; and a second Fc polypeptide comprising the amino acid sequence of any one of SEQ ID NOs: 41-42.

In some embodiments, the fusion protein comprises a first Fc polypeptide linked to a GAA enzyme comprising the amino acid sequence of any one of SEQ ID NOs: 58-59 and 69-70; and a second Fc polypeptide comprising the amino acid sequence of any one of SEQ ID NOs: 43-44.

In some embodiments, the fusion protein comprises a first Fc polypeptide linked to a GAA enzyme comprising the amino acid sequence of SEQ ID NO: 58; and a second Fc polypeptide comprising the amino acid sequence of any one of SEQ ID NOs: 43-44.

In some embodiments, the fusion protein comprises a first Fc polypeptide linked to a GAA enzyme comprising the amino acid sequence of SEQ ID NO: 58; and a second Fc polypeptide comprising the amino acid sequence of any one of SEQ ID NO: 44.

In some embodiments, the fusion protein comprises a first Fc polypeptide linked to a GAA enzyme comprising the amino acid sequence of SEQ ID NO: 59; and a second Fc polypeptide comprising the amino acid sequence of any one of SEQ ID NOs: 43-44.

In some embodiments, the fusion protein comprises a first Fc polypeptide linked to a GAA enzyme comprising the amino acid sequence of SEQ ID NO: 59; and a second Fc polypeptide comprising the amino acid sequence of SEQ ID NO: 44.

In some embodiments, the fusion protein comprises a first Fc polypeptide linked to a GAA enzyme comprising the amino acid sequence of SEQ ID NO: 69; and a second Fc polypeptide comprising the amino acid sequence of any one of SEQ ID NOs: 43-44.

In some embodiments, the fusion protein comprises a first Fc polypeptide linked to a GAA enzyme comprising the amino acid sequence of SEQ ID NO: 69; and a second Fc polypeptide comprising the amino acid sequence of SEQ ID NO: 44.

In some embodiments, the fusion protein comprises a first Fc polypeptide linked to a GAA enzyme comprising the amino acid sequence of SEQ ID NO: 70; and a second Fc polypeptide comprising the amino acid sequence of any one of SEQ ID NOs: 43-44.

In some embodiments, the fusion protein comprises a first Fc polypeptide linked to a GAA enzyme comprising the amino acid sequence of SEQ ID NO: 70; and a second Fc polypeptide comprising the amino acid sequence of SEQ ID NO: 43.

In some embodiments, the fusion protein comprises a first Fc polypeptide linked to a GAA enzyme comprising the amino acid sequence of SEQ ID NO: 70; and a second Fc polypeptide comprising the amino acid sequence of SEQ ID NO: 44.

In some embodiments, a GAA enzyme (e.g., a wild-type GAA enzyme, a GAA enzyme variant, or a catalytically active fragment of a wild-type GAA enzyme or GAA enzyme variant), present in a fusion protein described herein is linked to a first polypeptide chain that comprises a first Fc polypeptide having at least 85%, at least 90%, at least 95% identity, at least 96% identity, at least 97% identity, at least 98% identity, or at least 99% identity to any one of SEQ ID NOs: 17-20, or comprises the sequence of any one of SEQ ID NOs: 17-20 (e.g., as a fusion polypeptide). In some embodiments, the first GAA enzyme is linked to the first Fc polypeptide by a linker, such as a flexible linker, and/or a hinge region or portion thereof (e.g., DKTHTCPPCP; SEQ ID NO:6). In some embodiments, the N-terminus of the first Fc polypeptide includes a portion of an IgG1 hinge region (e.g., DKTHTCPPCP; SEQ ID NO:6). In some embodiments, the first Fc polypeptide has at least 85%, at least 90%, at least 95% identity, at least 96% identity, at least 97% identity, at least 98% identity, or at least 99% identity to any one of SEQ ID NOs:25-26, or comprises the sequence of any one of SEQ ID NOs:25-26. In some embodiments, the GAA enzyme comprises an amino acid sequence having at least 85%, at least 90%, at least 95% identity, at least 96% identity, at least 97% identity, at least 98% identity, or at least 99% identity to any one of SEQ ID NOs: 45-47 and 64-66, or comprises the sequence of any one of SEQ ID NOs: 45-47 and 64-66. In some embodiments, the fusion protein comprises a second Fc polypeptide having at least 85%, at least 90%, at least 95% identity, at least 96% identity, at least 97% identity, at least 98% identity, or at least 99% identity to any one of SEQ ID NOs: 37-40. In some embodiments, the fusion protein comprises a second Fc polypeptide having at least 85%, at least 90%, at least 95% identity, at least 96% identity, at least 97% identity, at least 98% identity, or at least 99% identity to any one of SEQ ID NOs: 37-40, and comprises Ala at position 389, according to EU numbering. In some of the foregoing embodiments, the second polypeptide further comprises at the following positions, according to EU numbering: Glu at position 380 and Asn at position 390. In some of the foregoing embodiments, the second Fc polypeptide comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some of the foregoing embodiments, the second Fc polypeptide comprises the sequence of any one of SEQ ID NOs:37-40. In some embodiments, the N-terminus of the second Fc polypeptide includes a portion of an IgG1 hinge region (e.g., DKTHTCPPCP; SEQ ID NO:6). In some embodiments, a second GAA enzyme is linked to the second Fc polypeptide by a linker, such as a flexible linker, and/or a hinge region or portion thereof (e.g., DKTHTCPPCP; SEQ ID NO:6).

In some embodiments, a GAA enzyme (e.g., a wild-type GAA enzyme, a GAA enzyme variant, or a catalytically active fragment of a wild-type GAA enzyme or GAA enzyme variant), present in a fusion protein described herein is linked to a first polypeptide chain that comprises a first Fc polypeptide having at least 85%, at least 90%, at least 95% identity, at least 96% identity, at least 97% identity, at least 98% identity, or at least 99% identity to any one of SEQ ID NOs: 29-36 (e.g., as a fusion polypeptide). In some embodiments, the first Fc polypeptide has at least 85%, at least 90%, at least 95% identity, at least 96% identity, at least 97% identity, at least 98% identity, or at least 99% identity to any one of SEQ ID NOs: 29-36, and comprises Ala at position 389, according to EU numbering. In some of the foregoing embodiments, the first polypeptide further comprises at the following positions, according to EU numbering: Glu at position 380 and Asn at position 390. In some of the foregoing embodiments, the first Fc polypeptide comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some of the foregoing embodiments, the first Fc polypeptide comprises the sequence of any one of SEQ ID NOs:29-36. In some embodiments, the GAA enzyme is linked to the first Fc polypeptide by a linker, such as a flexible linker, and/or a hinge region or portion thereof (e.g., DKTHTCPPCP; SEQ ID NO:6). In some embodiments, the N-terminus of the first Fc polypeptide includes a portion of an IgG1 hinge region (e.g., DKTHTCPPCP; SEQ ID NO:6). In some embodiments, the first Fc polypeptide has at least 85%, at least 90%, at least 95% identity, at least 96% identity, at least 97% identity, at least 98% identity, or at least 99% identity to any one of SEQ ID NOs:41-44. In some embodiments, the first Fc polypeptide has at least 85%, at least 90%, at least 95% identity, at least 96% identity, at least 97% identity, at least 98% identity, or at least 99% identity to any one of SEQ ID NOs: 41-44, and comprises Ala at position 389, according to EU numbering. In some of the foregoing embodiments, the first polypeptide further comprises at the following positions, according to EU numbering: Glu at position 380 and Asn at position 390. In some of the foregoing embodiments, the first Fc polypeptide comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some of the foregoing embodiments, the first Fc polypeptide comprises the sequence of any one of SEQ ID NOs:41-44. In some embodiments, the GAA enzyme comprises an amino acid sequence having at least 85%, at least 90%, at least 95% identity, at least 96% identity, at least 97% identity, at least 98% identity, or at least 99% identity to any one of SEQ ID NOs:45-47 and 64-66 or comprises the sequence of any one of SEQ ID NOs:45-47 and 64-66. In some embodiments, the fusion protein comprises a second Fc polypeptide having at least 85%, at least 90%, at least 95% identity, at least 96% identity, at least 97% identity, at least 98% identity, or at least 99% identity to any one of SEQ ID NOs: 9-16, or comprises the sequence of any one of SEQ ID NOs:9-16. In some embodiments, the N-terminus of the second Fc polypeptide includes a portion of an IgG1 hinge region (e.g., DKTHTCPPCP; SEQ ID NO:6). In some embodiments, the second Fc polypeptide has at least 85%, at least 90%, at least 95% identity, at least 96% identity, at least 97% identity, at least 98% identity, or at least 99% identity to any one of SEQ ID NOs:21-24, or comprises the sequence of any one of SEQ ID NOs:21-24. In some embodiments, a second GAA enzyme is linked to the second Fc polypeptide by a linker, such as a flexible linker, and/or a hinge region or portion thereof (e.g., DKTHTCPPCP; SEQ ID NO:6). In some embodiments, the second GAA enzyme comprises an amino acid sequence having at least 85%, at least 90%, at least 95% identity, at least 96% identity, at least 97% identity, at least 98% identity, or at least 99% identity to any one of SEQ ID NOs:45-47 and 64-66, or comprises the sequence of any one of SEQ ID NOs:45-47 and 64-66. In some embodiments, the second GAA sequence linked to the second Fc polypeptide has at least 85%, at least 90%, at least 95% identity, at least 96% identity, at least 97% identity, at least 98% identity, or at least 99% identity to any one of SEQ ID NOs: 48-59 and 67-70, or comprises the sequence of any one of SEQ ID NOs: 48-59 and 67-70.

In some embodiments, a GAA enzyme (e.g., a wild-type GAA enzyme, a GAA enzyme variant, or a catalytically active fragment of a wild-type GAA enzyme or GAA enzyme variant), present in a fusion protein described herein is linked to a first polypeptide chain that comprises a first Fc polypeptide having at least 85%, at least 90%, at least 95% identity, at least 96% identity, at least 97% identity, at least 98% identity, or at least 99% identity to any one of SEQ ID NOs: 37-40 (e.g., as a fusion polypeptide). In some embodiments, the first Fc polypeptide has at least 85%, at least 90%, at least 95% identity, at least 96% identity, at least 97% identity, at least 98% identity, or at least 99% identity to any one of SEQ ID NOs: 37-40, and comprises Ala at position 389, according to EU numbering. In some of the foregoing embodiments, the first polypeptide further comprises at the following positions, according to EU numbering: Glu at position 380 and Asn at position 390. In some of the foregoing embodiments, the first Fc polypeptide comprises at the following positions, according to EU numbering: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421. In some of the foregoing embodiments, the first Fc polypeptide comprises the sequence of any one of SEQ ID NOs: 37-40. In some embodiments, the GAA enzyme is linked to the first Fc polypeptide by a linker, such as a flexible linker, and/or a hinge region or portion thereof (e.g., DKTHTCPPCP; SEQ ID NO:6). In some embodiments, the N-terminus of the first Fc polypeptide includes a portion of an IgG1 hinge region (e.g., DKTHTCPPCP; SEQ ID NO:6). In some embodiments, the GAA enzyme comprises an amino acid sequence having at least 85%, at least 90%, at least 95% identity, at least 96% identity, at least 97% identity, at least 98% identity, or at least 99% identity to any one of SEQ ID NOs:45-47 and 64-66 or comprises the sequence of any one of SEQ ID NOs:45-47 and 64-66. In some embodiments, the fusion protein comprises a second Fc polypeptide having at least 85%, at least 90%, at least 95% identity, at least 96% identity, at least 97% identity, at least 98% identity, or at least 99% identity to any one of SEQ ID NOs: 17-20, or comprises the sequence of any one of SEQ ID NOs: 17-20. In some embodiments, the N-terminus of the second Fc polypeptide includes a portion of an IgG1 hinge region (e.g., DKTHTCPPCP; SEQ ID NO:6). In some embodiments, the second Fc polypeptide has at least 85%, at least 90%, at least 95% identity, at least 96% identity, at least 97% identity, at least 98% identity, or at least 99% identity to any one of SEQ ID NOs:25-26, or comprises the sequence of any one of SEQ ID NOs:25-26. In some embodiments, a second GAA enzyme is linked to the second Fc polypeptide by a linker, such as a flexible linker, and/or a hinge region or portion thereof (e.g., DKTHTCPPCP; SEQ ID NO:6).

In some embodiments, a fusion protein described herein comprises 1) a first Fc polypeptide linked to a GAA enzyme; and 2) a second Fc polypeptide; wherein each polypeptide consists of an amino acid sequence as recited in a foregoing embodiment.

In some embodiments, a fusion protein described herein comprises 1) a first Fc polypeptide linked to a first GAA enzyme; and 2) a second Fc polypeptide linked to a second GAA enzyme; wherein each polypeptide consists of an amino acid sequence as recited in a foregoing embodiment.

Fusion proteins and other compositions described herein may have a range of binding affinities. For example, in some embodiments, a protein has an affinity for a transferrin receptor (TfR), ranging anywhere from about 50 mM to about 500 nM, or from about 100 nM to about 500 nM. In some embodiments, the affinity for TfR ranges from about 50 nM to about 300 nM. In some embodiments, the affinity for TfR ranges from about 100 nM to about 350 nM. In some embodiments, the affinity for TfR ranges from about 150 nM to about 400 nM. In some embodiments, the affinity for TfR ranges from about 200 nM to about 400 nM. In some embodiments, the affinity for TfR ranges from about 200 nM to about 300 nM. In some embodiments, the affinity for TfR ranges from about 250 nM to about 300 nM. In some embodiments, the affinity for TfR ranges from about 200 nM to about 450 nM. In some embodiments, the affinity for TfR is a monovalent affinity.

In some embodiments, uptake of the GAA enzyme into the brain when administered as part of a fusion protein described herein is at least five-fold greater as compared to the uptake of the GAA enzyme in the absence of the first Fc polypeptide and the second Fc polypeptide or as compared to the uptake of the GAA enzyme without the modifications to the second Fc polypeptide that result in TfR binding.

In some embodiments, a composition comprising a plurality of a fusion protein described herein comprises a M6P content of less than about 1 mol/mol (e.g., less than or equal to about 0.6 mol/mol, less than or equal to about 0.3 mol/mol, or less than or equal to about 0.2 mol/mol), wherein the given value represents mole M6P per mole of fusion protein. In some embodiments, a composition comprising a plurality of a fusion protein described herein comprises a M6P content of less than about 1 mol/mol and greater than about 0.1 mol/mol, wherein the given value represents mole M6P per mole of fusion protein. Methods for measuring M6P content are known in the art and described herein (see, e.g., Example 2).

Evaluation of Protein Activity

Activity of fusion proteins described herein that comprise GAA enzymes can be assessed using various assays, including assays that measure activity in vitro using an artificial substrate, such as those described in the Examples section. For example, assays that measure activity in vitro using a fluorogenic artificial substrate, such as, 4-Methylumbelliferyl α-D-glucopyranoside (as described in Example 2), may also be used.

In some embodiments, a tissue sample is evaluated. A tissue sample can be evaluated using an assay, wherein multiple freeze-thaw cycles, e.g., 2, 3, 4, 5, or more, are typically included before a sonication step to ensure that microvesicles are broken open.

Samples that can be evaluated by the assays described herein include brain, liver, heart, quadricep, muscle, kidney, lung, spleen, plasma, serum, cerebrospinal fluid (CSF), and urine. In some embodiments, CSF samples from a patient receiving an enzyme-Fc fusion protein (e.g., GAA-Fc fusion protein) described herein may be evaluated.

Nucleic Acids, Vectors, and Host Cells

Polypeptide chains contained in the fusion proteins as described herein are typically prepared using recombinant methods. Accordingly, in some aspects, the present disclosure provides isolated nucleic acids comprising a nucleic acid sequence encoding any of the polypeptide chains comprising Fc polypeptides as described herein, and host cells into which the nucleic acids are introduced that are used to replicate the polypeptide-encoding nucleic acids and/or to express the polypeptides. In some embodiments, the host cell is eukaryotic, e.g., a human cell.

In another aspect, polynucleotides are provided that comprise a nucleotide sequence that encodes one or more of the polypeptide chains described herein. In some embodiments, the polynucleotide encodes one of the polypeptide sequences described here. In some embodiments, the polynucleotide encodes two of the polypeptide sequences described herein. The polynucleotides may be single-stranded or double-stranded. In some embodiments, the polynucleotide is DNA. In particular embodiments, the polynucleotide is cDNA. In some embodiments, the polynucleotide is RNA.

Some embodiments also provide a pair of nucleic acid sequences, wherein each nucleic acid sequence encodes a polypeptide described herein. For example, certain embodiments provide a pair of nucleic acid sequences, wherein a first nucleic acid sequence in the pair encodes a first Fc polypeptide linked to a first GAA enzyme; and a second nucleic acid sequence in the pair encodes a second Fc polypeptide, wherein the first and/or second Fc polypeptide is a modified Fc that is capable of binding (e.g., specifically binding) to a blood-brain barrier (BBB) receptor, e.g., a transferrin receptor (TfR).

In some embodiments, the polynucleotide is included within a nucleic acid construct or the pair of polynucleotides is included within one or more nucleic acid constructs. In some embodiments, the construct is a replicable vector. In some embodiments, the vector is selected from a plasmid, a viral vector, a phagemid, a yeast chromosomal vector, and a non-episomal mammalian vector.

In some embodiments, the polynucleotide is operably linked to one or more regulatory nucleotide sequences in an expression construct. In one series of embodiments, the nucleic acid expression constructs are adapted for use as a surface expression library. In some embodiments, the library is adapted for surface expression in yeast. In some embodiments, the library is adapted for surface expression in phage. In another series of embodiments, the nucleic acid expression constructs are adapted for expression of the polypeptide in a system that permits isolation of the polypeptide in milligram or gram quantities. In some embodiments, the system is a mammalian cell expression system. In some embodiments, the system is a yeast cell expression system.

Expression vehicles for production of a recombinant polypeptide include plasmids and other vectors. For instance, suitable vectors include plasmids of the following types: pBR322-derived plasmids, pEMBL-derived plasmids, pEX-derived plasmids, pBTac-derived plasmids, and pUC-derived plasmids for expression in prokaryotic cells, such as E. coli. The pcDNAI/amp, pcDNAI/neo, pRc/CMV, pSV2gpt, pSV2neo, pSV2-dhfr, pTk2, pRSVneo, pMSG, pSVT7, pko-neo, and pHyg-derived vectors are examples of mammalian expression vectors suitable for transfection of eukaryotic cells. Alternatively, derivatives of viruses such as the bovine papilloma virus (BPV-1), or Epstein-Barr virus (pHEBo, pREP-derived, and p205) can be used for transient expression of polypeptides in eukaryotic cells. In some embodiments, it may be desirable to express the recombinant polypeptide by the use of a baculovirus expression system. Examples of such baculovirus expression systems include pVL-derived vectors (such as pVL1392, pVL1393, and pVL941), pAcUW-derived vectors (such as pAcUW1), and pBlueBac-derived vectors. Additional expression systems include adenoviral, adeno-associated virus, and other viral expression systems.

Vectors may be transformed into any suitable host cell. In some embodiments, the host cells, e.g., bacteria or yeast cells, may be adapted for use as a surface expression library. In some cells, the vectors are expressed in host cells to express relatively large quantities of the polypeptide. Such host cells include mammalian cells, yeast cells, insect cells, and prokaryotic cells. In some embodiments, the cells are mammalian cells, such as Chinese Hamster Ovary (CHO) cell, baby hamster kidney (BHK) cell, NS0 cell, Y0 cell, HEK293 cell, COS cell, Vero cell, or HeLa cell.

A host cell transfected with an expression vector(s) encoding one or more Fc polypeptide chains as described herein can be cultured under appropriate conditions to allow expression of the one or more polypeptides to occur. The polypeptides may be secreted and isolated from a mixture of cells and medium containing the polypeptides. Alternatively, the polypeptides may be retained in the cytoplasm or in a membrane fraction and the cells harvested, lysed, and the polypeptide isolated using a desired method.

Therapeutic Methods

A fusion protein or polypeptide as described herein may be used therapeutically to treat Pompe disease.

Accordingly, certain embodiments provide a method of decreasing the accumulation of a toxic metabolic product in a subject having Pompe disease, the method comprising administering a protein or polypeptide as described herein to the subject. In certain embodiments, the toxic metabolic product is glycogen.

Certain embodiments provide a protein or polypeptide as described herein for use in decreasing the accumulation of a toxic metabolic product in a subject having Pompe disease. In certain embodiments, the toxic metabolic product is glycogen.

Certain embodiments provide the use of a protein or polypeptide as described herein in the preparation of a medicament for decreasing the accumulation of a toxic metabolic product in a subject having Pompe disease. In certain embodiments, the toxic metabolic product is glycogen.

Certain embodiments also provide a method of treating Pompe disease, comprising administering a protein or polypeptide as described herein to a subject in need thereof.

Certain embodiments provide a protein or polypeptide as described herein for use in treating Pompe disease in a subject in need thereof.

Certain embodiments provide the use of a protein or polypeptide as described herein in the preparation of a medicament for treating Pompe disease in a subject in need thereof.

In some embodiments, administration of the protein (e.g., linked to a GAA enzyme) improves (e.g., increases) $C_{max}$ of GAA in the brain as compared to the uptake of GAA in the absence of being linked to a fusion protein described herein or as compared to the uptake of GAA linked to a reference protein (e.g., a fusion protein as described herein, which does not have the modifications to the second Fc polypeptide that result in TfR binding).

In some embodiments, $C_{max}$ of GAA in the brain is improved (e.g., increased) by at least about 1.1-fold, 1.2-fold, 1.3-fold, 1.4-fold, 1.5-fold, 1.6-fold, 1.7-fold, 1.8-fold, 1.9-fold, 2-fold, 2.2-fold, 2.4-fold, 2.6-fold, 2.8-fold, 3-fold, 4-fold, 5-fold, 6-fold, or more, as compared to the uptake of GAA in the absence of being linked to a fusion protein described herein or as compared to the uptake of GAA linked to a reference protein (e.g., a fusion protein as described herein, which does not have the modifications to the second Fc polypeptide that result in TfR binding).

A fusion protein or polypeptide described herein is administered to a subject at a therapeutically effective amount or dose.

In various embodiments, a fusion protein or polypeptide described herein is administered parenterally. In some embodiments, the protein or polypeptide is administered intravenously.

In some parenteral embodiments, a fusion protein or polypeptide as described herein is administered intraperitoneally, intradermally, or intramuscularly. In some embodiments, the fusion protein or polypeptide as described herein is administered intrathecally, such as by epidural administration, or intracerebroventricularly.

Pharmaceutical Compositions and Kits

In other aspects, pharmaceutical compositions and kits comprising a fusion protein or polypeptide described herein are provided.

Pharmaceutical Compositions

Guidance for preparing formulations for use in the present disclosure can be found in any number of handbooks for pharmaceutical preparation and formulation that are known to those of skill in the art.

In some embodiments, a pharmaceutical composition comprises a fusion protein or polypeptide as described herein and further comprises one or more pharmaceutically acceptable carriers and/or excipients. A pharmaceutically acceptable carrier includes any solvents, dispersion media, or coatings that are physiologically compatible and that do not interfere with or otherwise inhibit the activity of the active agent.

In certain embodiments, the pharmaceutical composition comprises a M6P content of less than about 1 mol/mol (e.g., less than or equal to about 0.6 mol/mol, less than or equal to about 0.3 mol/mol, or less than or equal to about 0.2 mol/mol), wherein the given value represents mole M6P per mole of fusion protein. In certain embodiments, the pharmaceutical composition comprises a M6P content of less than about 1 mol/mol and greater than about 0.1 mol/mol, wherein the given value represents mole M6P per mole of fusion protein.

Dosages and desired drug concentration of pharmaceutical compositions described herein may vary depending on the particular use envisioned.

Kits

In some embodiments, a kit for use in treating Pompe disease, comprising a fusion protein or polypeptide as described herein, is provided.

In some embodiments, the kit further comprises one or more additional therapeutic agents. For example, in some embodiments, the kit comprises a fusion protein or polypeptide as described herein and further comprises one or more additional therapeutic agents for use in the treatment of one or more symptoms of Pompe disease. In some embodiments, the kit further comprises instructional materials containing directions (i.e., protocols) for the practice of the methods described herein (e.g., instructions for using the kit for administering a fusion protein comprising a GAA enzyme across the blood-brain barrier). While the instructional materials typically comprise written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD-ROM), and the like. Such media may include addresses to internet sites that provide such instructional materials.

Certain Definitions

As used herein, the singular forms "a," "an," and "the" include plural referents unless the content clearly dictates otherwise. Thus, for example, reference to "a polypeptide" may include two or more such molecules, and the like.

As used herein, the terms "about" and "approximately," when used to modify an amount specified in a numeric value or range, indicate that the numeric value as well as reasonable deviations from the value known to the skilled person in the art, for example ±20%, ±10%, or ±5%, are within the intended meaning of the recited value.

The term "plurality" as used herein refers to two or more. For example, the term plurality may be used to refer to 10, 50, 100, 500, 1,000, 5,000, 10,000, 50,000, 100,000, 500,000, 1,000,000, or more.

The term "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the patient is a human. In some embodiments, the human is a patient in need of treatment for Pompe disease. In some embodiments, the patient has one or more signs or symptoms of Pompe disease.

The term "pharmaceutically acceptable excipient" refers to a non-active pharmaceutical ingredient that is biologically or pharmacologically compatible for use in humans or animals, such as but not limited to a buffer, carrier, or preservative.

The term "administer" refers to a method of delivering agents (e.g., a Pompe disease therapeutic agent, such as an ETV:GAA therapy described herein), compounds, or compositions (e.g., pharmaceutical composition) to the desired site of biological action. These methods include, but are not limited to, parenteral delivery, intravenous delivery, intradermal delivery, intramuscular delivery, intrathecal delivery, or intraperitoneal delivery. In one embodiment, the polypeptides described herein are administered intravenously.

As used herein, "treatment" (and grammatical variations thereof such as "treat" or "treating") refers to clinical intervention to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis.

The phrase "effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

A "therapeutically effective amount" of a substance/molecule disclosed herein may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

An "alpha-glucosidase, acid", "alpha-1,4-glucosidase", "Lysosomal alpha-glucosidase", "acid maltase", or "GAA" as used herein refers to acid alpha-glucosidase (EC 3.2.1.20), which is an enzyme involved in the lysosomal degradation of glycogen. Mutations in the GAA gene are associated with Pompe disease, which results from impaired degradation of glycogen. The term "GAA" or "GAA enzyme" as used herein, optionally as a component of a protein that comprises an Fc polypeptide, is catalytically active and encompasses functional variants, including allelic and splice variants, as well as catalytically active fragments of wild-type GAA and its functional variants. A full-length, wild-type sequence of human GAA is available under UniProt entry P10253 and is encoded by the human GAA gene at 17q25.3 (see, SEQ ID NO:45). Another embodiment of a full-length, human GAA enzyme sequence, which includes a combination of individual mutations that occur with >50% frequency in the human population (H199R, R223H, and V780I), is provided as SEQ ID NO:64, wherein the positions and substitutions of the mutations are relative to SEQ ID NO:45. A "mature" GAA sequence as used herein refers to a form of a polypeptide chain that lacks the signal sequence of the naturally occurring full-length polypeptide chain. Embodiments of mature human GAA polypeptides are provided as SEQ ID NOs:46 and 65, which correspond to amino acids 28-952 of the full-length human sequence. A "truncated" GAA sequence as used herein refers to a catalytically active fragment of the naturally occurring full-length polypeptide chain (e.g., SEQ ID NOs:47 or 66). The structure of human GAA has been well-characterized. Non-human primate GAA sequences have also been described, including orangutan (e.g., UniProt entry Q5R7A9 for *Pongo abelii* (*Sumatran orangutan*) (*Pongo pygmaeus abelii*)). A mouse GAA sequence is available under Uniprot entry P70699. Commercially available recombinant forms of GAA include: alglucosidase alfa (LUMIZYME®) and avalglucosidase alfa (NEXVIAZYME®).

As used herein, a "GAA enzyme variant" is functional (i.e., is catalytically active) and comprises at least one substitution, insertion or deletion relative to a wild-type GAA enzyme. In particular, a GAA enzyme variant has at least 50% (e.g., or at least 55%, at least 60%, at least 65%, at least 70%, at least 75%, at least 80%, at least 85%, at least 90%, or at least 95%) of the activity of a corresponding wild-type GAA, e.g., when assayed under identical conditions. In certain embodiments, the GAA enzyme variant comprises an amino acid sequence having about 85%-99%, 90%-99%, 95%-99%, 96%-99%, 97%-99%, 98%-99%, or 99% identity to a wild-type GAA enzyme (e.g., SEQ ID NO:45). An exemplary GAA enzyme variant is the full-length, human GAA enzyme sequence described supra and identified as SEQ ID NO:64, which includes the combination of H199R/R223H/V780I mutations.

As used herein, a "catalytically active GAA fragment" refers to a fragment of a full-length, wild-type GAA enzyme or GAA enzyme variant that has been truncated (e.g., no more than about 20%, 15%, 10%, 5% or less of the full-length, wild-type GAA enzyme or GAA enzyme variant has been truncated). For example, in certain embodiments, the catalytically active fragment is a fragment of a full-length, wild-type GAA enzyme or GAA enzyme variant that has been truncated in length by about 200, 150, 100, or 50 or fewer amino acids. A catalytically active GAA fragment has at least 50% (e.g., at least 55%, at least 60%, at least 65%, at least 70%, at least 75%, at least 80%, at least 85%, at least 90%, or at least 95%) of the activity of the corresponding full-length, wild-type GAA enzyme or variant thereof, e.g., when assayed under identical conditions. Exemplary catalytically active GAA fragments include the truncated GAA sequences described supra and identified as SEQ ID NOs.: 47 and 66.

Assays for evaluating enzymatic activity include, e.g., ELISA methods involving a fluorogenic substrate and GAA substrate correction assays (e.g., in vitro glycogen assays). For example, assays that measure activity in vitro using a fluorogenic artificial substrate, such as those described in the Examples section (e.g., 4-Methylumbelliferyl α-D-glucopyranoside as described in Example 2), may be used. In some embodiments, GAA substrate correction assays can be used, e.g., by detecting a correction in the levels of glycogen-derived glucose levels in a GAA knockout cell or cell line (e.g. GAA knock-out HEK293 cells). Mass spectrometry-based methods for measuring glycogen-derived glucose levels are described in, e.g., Fuller et al. 2012. *Analytical Biochemistry* 421:759-763. Additional methods for measuring glycogen or glycogen-derived glucose levels are known in the art.

A "transferrin receptor" or "TfR" as used herein refers to transferrin receptor protein 1. The human transferrin receptor 1 polypeptide sequence is set forth in SEQ ID NO:7. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full-length transferrin receptor protein includes a short N-terminal intracellular region, a transmembrane region, and a large extracellular domain. The extracellular domain is characterized by three domains: a protease-like domain, a helical domain, and an apical domain. The apical domain sequence of human transferrin receptor 1 is set forth in SEQ ID NO:8.

A "fusion protein" or "GAA enzyme-Fc fusion protein" or "GAA-Fc fusion protein" as used herein refers to a protein (e.g., a dimeric protein) comprising a first Fc polypeptide that is linked (e.g., fused) to a GAA enzyme (i.e., an "GAA-Fc fusion polypeptide"); and a second Fc polypeptide (e.g., that forms an Fc dimer with the first Fc polypeptide). The second Fc polypeptide may also be linked (e.g., fused) to a GAA enzyme. The first Fc polypeptide and/or the second Fc polypeptide may be linked to the GAA enzyme by a peptide bond or by a polypeptide linker. The first Fc polypeptide and/or the second Fc polypeptide may be a modified Fc polypeptide that contains one or more modifications that promote its heterodimerization to the other Fc polypeptide. The first Fc polypeptide and/or the second Fc polypeptide may be a modified Fc polypeptide that contains one or more modifications that confer binding to a transferrin receptor. The first Fc polypeptide and/or the second Fc polypeptide may be a modified Fc polypeptide that contains one or more modifications that reduce effector function. In certain embodiments, the first Fc polypeptide and the second Fc polypeptide do not have effector function. The first Fc polypeptide and/or the second Fc polypeptide may be a modified Fc polypeptide that contains one or more modifications that extend serum half-life. In certain embodiments, the first Fc polypeptide and/or the second Fc polypeptide do not include an immunoglobulin heavy and/or light chain variable region sequence or an antigen-binding portion thereof. In certain embodiments, the first Fc polypeptide and the second Fc polypeptide do not include an immunoglobulin heavy and/or light chain variable region sequence or an antigen-binding portion thereof.

A "fusion polypeptide" or "GAA enzyme-Fc fusion polypeptide" or "GAA-Fc fusion polypeptide" as used herein refers to an Fc polypeptide that is linked (e.g., fused) to a GAA enzyme. The Fc polypeptide may be linked to the GAA enzyme by a peptide bond or by a polypeptide linker. The Fc polypeptide may be a modified Fc polypeptide that contains one or more modifications that promote its heterodimerization to another Fc polypeptide. The Fc polypeptide may be a modified Fc polypeptide that contains one or more modifications that confer binding to a transferrin receptor. The Fc polypeptide may be a modified Fc polypeptide that contains one or more modifications that reduce effector function. The Fc polypeptide may be a modified Fc polypeptide that contains one or more modifications that extend serum half-life.

As used herein, the term "Fc polypeptide" refers to the C-terminal region of a naturally occurring immunoglobulin heavy chain polypeptide that is characterized by an Ig fold as a structural domain. An Fc polypeptide contains constant region sequences including at least the CH2 domain and/or the CH3 domain and may contain at least part of the hinge region. In general, an Fc polypeptide does not contain a variable region.

A "modified Fc polypeptide" refers to an Fc polypeptide that has at least one mutation, e.g., a substitution, deletion or insertion, as compared to a wild-type immunoglobulin heavy chain Fc polypeptide sequence, but retains the overall Ig fold or structure of the native Fc polypeptide.

The term "FcRn" refers to the neonatal Fc receptor. Binding of Fc polypeptides to FcRn reduces clearance and increases serum half-life of the Fc polypeptide. The human FcRn protein is a heterodimer that is composed of a protein of about 50 kDa in size that is similar to a major histocompatibility (MHC) class I protein and a β2-microglobulin of about 15 kDa in size.

As used herein, an "FcRn binding site" refers to the region of an Fc polypeptide that binds to FcRn. In human IgG, the FcRn binding site, as numbered using the EU index, includes T250, L251, M252, I253, S254, R255, T256, T307, E380, M428, H433, N434, H435, and Y436. These positions correspond to positions 20 to 26, 77, 150, 198, and 203 to 206 of SEQ ID NO:1.

As used herein, a "native FcRn binding site" refers to a region of an Fc polypeptide that binds to FcRn and that has the same amino acid sequence as the region of a naturally occurring Fc polypeptide that binds to FcRn.

The terms "CH3 domain" and "CH2 domain" as used herein refer to immunoglobulin constant region domain polypeptides. For purposes of this application, a CH3 domain polypeptide refers to the segment of amino acids from about position 341 to about position 447 as numbered according to EU, and a CH2 domain polypeptide refers to the segment of amino acids from about position 231 to about position 340 as numbered according to the EU numbering scheme and does not include hinge region sequences. CH2 and CH3 domain polypeptides may also be numbered by the IMGT (ImMunoGeneTics) numbering scheme in which the CH2 domain numbering is 1-110 and the CH3 domain numbering is 1-107, according to the IMGT Scientific chart numbering (IMGT website). CH2 and CH3 domains are part of the Fc region of an immunoglobulin. An Fc region refers to the segment of amino acids from about position 231 to about position 447 as numbered according to the EU numbering scheme, but as used herein, can include at least a part of a hinge region of an antibody. An illustrative hinge region sequence is the human IgG1 hinge sequence EPKSCDKTH-TCPPCP (SEQ ID NO:5).

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation. For example, the terms "wild-type," "native," and "naturally occurring" with respect to a CH3 or CH2 domain are used herein to refer to a domain that has a sequence that occurs in nature.

As used herein, the term "mutant" with respect to a mutant polypeptide or mutant polynucleotide is used interchangeably with "variant." A variant with respect to a given wild-type reference sequence (e.g., CH3 or CH2 domain reference sequence) can include naturally occurring allelic variants. Accordingly, a "non-naturally" occurring CH3 or CH2 domain refers to a variant or mutant domain that is not present in a cell in nature and that is produced by genetic modification, e.g., using genetic engineering technology or mutagenesis techniques, of a native CH3 domain or CH2 domain polynucleotide or polypeptide. A "variant" includes any domain comprising at least one amino acid mutation with respect to wild-type. Mutations may include substitutions, insertions, and deletions.

The term "amino acid" refers to naturally occurring and synthetic amino acids, as well as amino acid analogs and amino acid mimetics that function in a manner similar to the naturally occurring amino acids.

Naturally occurring amino acids are those encoded by the genetic code, as well as those amino acids that are later modified, e.g., hydroxyproline, γ-carboxyglutamate and O-phosphoserine. "Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid.

Naturally occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e, two) or multimer (i.e., three or more) of single chain polypeptides. The single chain polypeptides of a protein may be joined by a covalent bond, e.g., a disulfide bond, or non-covalent interactions.

The term "conservative substitution," "conservative mutation," or "conservatively modified variant" refers to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH$_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 60% identity, at least 65%, at least 70%, at least 75%, at least 80%, at least 85%, at least 90%, or at least 95% or greater, that are identical over a specified region when compared and aligned for maximum correspondence over a comparison window, or designated region, as measured using a sequence comparison algorithm or by manual alignment and visual inspection. In some embodiments, a sequence that has a specified percent identity relative to a reference sequence differs from the reference sequence by one or more conservative substitutions.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a modified Fc polypeptide "corresponds to" an amino acid in SEQ ID NO:1, when the residue aligns with the amino acid in SEQ ID NO:1 when optimally aligned to SEQ ID NO:1. The polypeptide that is aligned to the reference sequence need not be the same length as the reference sequence.

The term "polynucleotide" and "nucleic acid" interchangeably refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. Examples of polynucleotides contemplated herein include single- and double-stranded DNA, single- and double-stranded RNA, and hybrid molecules having mixtures of single- and double-stranded DNA and RNA.

A "binding affinity" as used herein refers to the strength of the non-covalent interaction between two molecules, e.g., a single binding site on a polypeptide and a target, e.g., transferrin receptor, to which it binds. Thus, for example, the term may refer to 1:1 interactions between a polypeptide and its target, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet® platform). As used herein, "binding affinity" includes not only formal binding affinities, such as those reflecting 1:1 interactions between a polypeptide and its target, but also apparent affinities for which $K_D$'s are calculated that may reflect avid binding.

As used herein, the term "specifically binds" or "selectively binds" to a target, e.g., TfR, when referring to an engineered TfR-binding polypeptide, TfR-binding peptide, or TfR-binding fusion protein as described herein, refers to a binding reaction whereby the engineered TfR-binding polypeptide, TfR-binding peptide, or TfR-binding fusion protein binds to the target with greater affinity, greater avidity, and/or greater duration than it binds to a structurally different target. In typical embodiments, the engineered TfR-binding polypeptide, TfR-binding peptide, or TfR-binding fusion protein has at least 5-fold, 10-fold, 50-fold, 100-fold, 1,000-fold, 10,000-fold, or greater affinity for a specific target, e.g., TfR, compared to an unrelated target when assayed under the same affinity assay conditions. The term "specific binding," "specifically binds to," or "is specific for" a particular target (e.g., TfR), as used herein, can be exhibited, for example, by a molecule having an equilibrium dissociation constant $K_D$ for the target to which it binds of, e.g., $10^{-4}$ M or smaller, e.g., $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In some embodiments, an engineered TfR-binding polypeptide, TfR-binding peptide, or TfR-binding fusion protein specifically binds to an epitope on TfR that is conserved among species, (e.g., structurally conserved among species), e.g., conserved between non-human primate and human species (e.g., structurally conserved between non-human primate and human species). In some embodiments, an engineered TfR-binding polypeptide, TfR-binding peptide, or TfR-binding fusion protein may bind exclusively to a human TfR.

The term "variable region" or "variable domain" refers to a domain in an antibody heavy chain or light chain that is derived from a germline Variable (V) gene, Diversity (D) gene, or Joining (J) gene (and not derived from a Constant (Cμ and Cδ) gene segment), and that gives an antibody its specificity for binding to an antigen. Typically, an antibody variable region comprises four conserved "framework" regions interspersed with three hypervariable "complementarity determining regions."

The terms "antigen-binding portion" and "antigen-binding fragment" are used interchangeably herein and refer to one or more fragments of an antibody that retains the ability to specifically bind to an antigen via its variable region. Examples of antigen-binding fragments include, but are not limited to, a Fab fragment (a monovalent fragment consisting of the VL, VH, CL, and CH1 domains), a F(ab')$_2$ fragment (a bivalent fragment comprising two Fab fragments linked by a disulfide bridge at the hinge region), a single chain Fv (scFv), a disulfide-linked Fv (dsFv), complementarity determining regions (CDRs), a VL (light chain variable region), and a VH (heavy chain variable region).

The following Examples are intended to be non-limiting.

Example 1: Construction of Fusion Proteins Comprising Acid Alpha-Glucosidase (GAA)

Design and Cloning

GAA-Fc fusion proteins were designed that contain (i) a first fusion polypeptide where a human GAA enzyme sequence is fused to a human IgG1 fragment that includes the Fc region (a "GAA-Fc fusion polypeptide"), and (ii) a modified human IgG1 fragment which contains mutations in the Fc region that confer transferrin receptor (TfR) binding (a "modified Fc polypeptide"). GAA-Fc fusion polypeptides were created in which GAA sequences were fused to the N- or C-terminus of the human IgG1 Fc region. In all constructs, the signal peptide MGWSCIILFLVATATGAYA (SEQ ID NO: 60) was inserted upstream of the fusion to facilitate secretion. The fragment of the human IgG1 Fc region used corresponds to amino acids D104-K330 of the sequence in UniProtKB ID P01857 (positions 221-447, EU numbering, which includes 10 amino acids of the hinge (positions 221-230)). Expression vectors that separately encode (i) the GAA-Fc fusion polypeptide; and (ii) the modified Fc polypeptide were generated and co-transfected into Chinese Hamster Ovary (CHO) cells to generate heterodimeric fusion proteins containing a GAA enzyme (a "monozyme"). In some constructs, the IgG1 fragments contained additional mutations to facilitate heterodimerization of the two Fc regions.

A GAA-Fc fusion polypeptide comprising a mature human GAA sequence fused to the N-terminus of an IgG1 Fc polypeptide sequence with hole and LALAPS mutations has the sequence of SEQ ID NO:52 or 53. The GAA enzyme was joined to the Fc polypeptide by a GGGGS linker (SEQ ID NO:62) and the N-terminus of the Fc polypeptide included a portion of an IgG1 hinge region (DKTHTCPPCP; SEQ ID NO:6).

A GAA-Fc fusion polypeptide comprising a truncated human GAA sequence fused to the N-terminus of an IgG1 Fc polypeptide sequence with hole and LALAPS mutations has the sequence of SEQ ID NO: 54 or 55. The GAA enzyme was joined to the Fc polypeptide by a GGGGS linker (SEQ ID NO:62) and the N-terminus of the Fc polypeptide included a portion of an IgG1 hinge region (DKTHTCPPCP; SEQ ID NO:6).

A GAA-Fc fusion polypeptide comprising a mature human GAA sequence fused to the C-terminus of an IgG1 Fc polypeptide sequence with hole and LALAPS mutations has the sequence of SEQ ID NO:58. The GAA enzyme was joined to the Fc polypeptide by a GGGGS linker (SEQ ID NO:62) and the N-terminus of the Fc polypeptide included a portion of an IgG1 hinge region (DKTHTCPPCP; SEQ ID NO:6). The foregoing embodiment may also be referred to as an "Fc-GAA fusion polypeptide."

A GAA-Fc fusion polypeptide comprising a truncated human GAA sequence fused to the C-terminus of an IgG1 Fc polypeptide sequence with hole and LALAPS mutations has the sequence of SEQ ID NO:59. The GAA enzyme was joined to the Fc polypeptide by a GGGGS linker (SEQ ID NO:62) and the N-terminus of the Fc polypeptide included a portion of an IgG1 hinge region (DKTHTCPPCP; SEQ ID NO:6). The foregoing embodiment may also be referred to as an "Fc-GAA fusion polypeptide."

A TfR-binding modified Fc polypeptide with knob and LALAPS mutations has the sequence of SEQ ID NO:43 or 44. The N-terminus of the modified Fc polypeptide included a portion of an IgG1 hinge region (DKTHTCPPCP; SEQ ID NO:6).

An "N-terminal monozyme" GAA-Fc fusion protein ("ETV:GAA Fusion 1") was generated, which comprises a TfR-binding modified Fc polypeptide having the sequence of SEQ ID NO:43 and a GAA-Fc fusion polypeptide having the sequence of SEQ ID NO:52. The GAA-Fc fusion protein may also be further processed during cell culture production, such that the TfR-binding modified Fc polypeptide has the sequence of SEQ ID NO:44 and/or the GAA-Fc fusion polypeptide has the sequence of SEQ ID NO:53. Thus, as used herein, the term ETV:GAA Fusion 1 may be used to refer to protein molecules having unprocessed sequences (i.e., SEQ ID NOs:43 and 52); protein molecules comprising one or more processed sequences (i.e., selected from SEQ ID NOs: 44 and 53); or to a mixture comprising processed and unprocessed protein molecules.

An "N-terminal monozyme" GAA-Fc fusion protein ("ETV:GAA Fusion 2") was generated, which comprises a TfR-binding modified Fc polypeptide having the sequence of SEQ ID NO:43 and a GAA-Fc fusion polypeptide having the sequence of SEQ ID NO:54. The GAA-Fc fusion protein may also be further processed during cell culture production, such that the TfR-binding modified Fc polypeptide has the sequence of SEQ ID NO:44 and/or the GAA-Fc fusion polypeptide has the sequence of SEQ ID NO:55. Thus, as used herein, the term ETV:GAA Fusion 2 may be used to refer to protein molecules having unprocessed sequences (i.e., SEQ ID NOs:43 and 54); protein molecules comprising one or more processed sequences (i.e., selected from SEQ ID NOs: 44 and 55); or to a mixture comprising processed and unprocessed protein molecules.

A "C-terminal monozyme" GAA-Fc fusion protein ("ETV:GAA Fusion 3") was generated, which comprises a TfR-binding modified Fc polypeptide having the sequence of SEQ ID NO:43 and an Fc-GAA fusion polypeptide having the sequence of SEQ ID NO:58. The GAA-Fc fusion protein may also be further processed during cell culture production, such that the TfR-binding modified Fc polypeptide has the sequence of SEQ ID NO:44. Thus, as used herein, the term ETV:GAA Fusion 3 may be used to refer to protein molecules comprising SEQ ID NOs:43 and 58; protein molecules comprising SEQ ID NOs:44 and 58; or to a mixture having protein molecules comprising SEQ ID NOs:43 and 58 and protein molecules comprising SEQ ID NOs:44 and 58.

A "C-terminal monozyme" GAA-Fc fusion protein ("ETV:GAA Fusion 4") was generated, which comprises a TfR-binding modified Fc polypeptide having the sequence of SEQ ID NO:43 and an Fc-GAA fusion polypeptide having the sequence of SEQ ID NO:59. The GAA-Fc fusion protein may also be further processed during cell culture production, such that the TfR-binding modified Fc polypeptide has the sequence of SEQ ID NO:44. Thus, as used herein, the term ETV:GAA Fusion 4 may be used to refer to protein molecules comprising SEQ ID NOs:43 and 59; protein molecules comprising SEQ ID NOs:44 and 59; or to a mixture having protein molecules comprising SEQ ID NOs:43 and 59 and protein molecules comprising SEQ ID NOs:44 and 59.

A composition comprising ETV:GAA (e.g., any of the fusion proteins described above) may be used to refer to a composition comprising protein molecules having unprocessed sequences; protein molecules comprising one or more processed sequences; or to a mixture comprising processed and unprocessed protein molecules.

Recombinant Protein Expression and Purification

To express recombinant GAA-Fc fusion proteins, CHO-K1 cells (Horizon Discovery) were transfected with relevant DNA constructs using TransIT-PRO Transfection Reagent according to manufacturer's instructions (Mirus Bio, cat #MIR5700). Cells were grown in BalanCD Transfectory CHO expression media (Irvine Scientific, cat #91147-1L) at 37° C., 5% $CO_2$ and 125 rpm in an orbital shaker (Infors HT Multitron). In brief, logarithmic growing Horizon CHO-K1 cells were transfected at $5\times10^6$ cells/ml density with 0.8 µg of total DNA plasmid per mL of culture volume. After transfection, cells were temperature shifted to 32° C. Twenty-four (24) hours post transfection cells were provided a nutrient feed, BalanCD CHO Feed 4 (Irvine Scientific, cat #94134-1L). Transfected cell culture supernatants were harvested 168 hours post transfection by centrifugation at 4000 rpm for 10 minutes.

The GAA-Fc fusion proteins were purified from cell culture supernatants using Protein A affinity chromatography. Supernatants were loaded onto a HiTrap MabSelect SuRe Protein A affinity column (GE Healthcare Life Sciences using an Akta Pure System). The column was then washed with 10 column volumes (CVs) of PBS. Bound proteins were eluted using 50 mM citrate/NaOH buffer pH 3.0 containing 100 mM NaCl. Immediately after elution, fractions were neutralized using 1 M Tris pH8 (at a 1:7 dilution). Homogeneity of GAA-Fc fusions in eluted fractions was assessed by a number of techniques including reducing and non-reducing SDS-PAGE and HPLC-SEC.

Where additional purification was carried out, the Protein A pool was diluted 10-fold into 20 mM sodium acetate at pH 5.0 and further purified by cation-exchange chromatography (CEX) over a ResourceQ column (Cytivas). Briefly, after binding, the column was washed with 10 CV of 20 mM sodium acetate and 5 mM NaCl at pH 5.0. Bound proteins were eluted using a linear gradient of 5 mM NaCl to 500 mM NaCl in 20 mM sodium acetate at pH 5.0. Homogeneity of post-CEX purified ETV:GAA was assessed by SDS-PAGE and analytical SEC-HPLC. Fractions with >98% purity were pooled and dialyzed over 20 mM sodium phosphate, 150 mM NaCl, at pH 6.5 overnight.

Example 2: Characterization and Product Quality Attributes of GAA-Fc Fusion Proteins ETV:GAA Fusions 1, 2, 3, and 4 (Example 1) were evaluated in terms of TfR-binding, enzymatic activity, and product quality relative to each other and to LUMIZYME®.

GAA-Fc Fusion Proteins with Engineered TfR Binding Site Bind to Human TfR

To determine whether GAA-Fc fusion proteins with engineered TfR binding affects the ability of the modified Fc domain to interact with human TfR, the affinity of ETV:GAA fusion proteins (Example 1) for human TfR was assessed using a Biacore™ surface plasmon resonance assay. Biacore™ Series S CM5 sensor chips were immobilized with anti-human Fab (human Fab capture kit from GE Healthcare). Five (5) μg/mL of the GAA-Fc fusion proteins were captured for 1 minute on each flow cell and serial 3-fold dilutions of human apical domain TfR were injected at a flow rate of 30 μL/min. Each sample was analyzed with a 3-minute association and a 3-minute dissociation. After each injection, the chip was regenerated using 10 mM glycine-HCl (pH 2.1). Binding response was corrected by subtracting the RU from a flow cell capturing an irrelevant IgG at similar density. Steady-state affinities were obtained by fitting the response at equilibrium against the concentration using Biacore™ T200 Evaluation Software v3.1. Biacore™ analysis established that GAA-Fc fusion proteins with a TfR-binding site engineered into the Fc region bind to human TfR. In particular, the binding affinity of ETV:GAA fusion proteins for human TfR was determined to range from about 250-300 nM (Table 1).

TABLE 1

ETV:GAA Fusion Protein Affinity for human TfR

| Fusion Protein | huTfR $K_D$ (nM) |
|---|---|
| ETV:GAA Fusion 1 | 251 |
| ETV:GAA Fusion 2 | 260 |

TABLE 1-continued ETV:GAA Fusion Protein Affinity for human TfR

| Fusion Protein | huTfR $K_D$ (nM) |
|---|---|
| ETV:GAA Fusion 3 | 282 |
| ETV:GAA Fusion 4 | 271 |

GAA-Fc Fusion Proteins with Engineered TfR Binding Site are Active In Vitro

The in vitro activity of engineered TfR-binding GAA-Fc fusion proteins were assessed to demonstrate that GAA maintains its enzymatic activity when fused to the human IgG fragment. The in vitro activity of recombinant GAA was measured using a one-step fluorometric enzymatic assay using an artificial substrate. Specifically, fresh 400 mM 4-methylumbelliferyl α-D-glucopyranoside (Sigma #M9766) was made and diluted in a 10% DMSO Assay Buffer (50 mM sodium acetate, 0.5 M NaCl, 0.025% Triton X-100, DMSO, pH 4.5) solution to a final concentration of 10 mM. GAA-Fc fusion proteins were serially diluted starting from a concentration of 50 mM. Five (5) µL substrate was then mixed with 5 µL of the serially diluted GAA-Fc fusion protein in a 384-well black, flat bottom microplate plate (NUNC #262260). The reaction was incubated for 60 minutes at 22° C. and terminated with 10 µL of Stop Buffer (0.5 M sodium carbonate buffer, pH 10.3). Fluorescence of the reaction solution was then measured (excitation at 365 nm and emission at 450 nm). A 4-Methylumbelliferone standard curve was fit by non-linear regression to calculate the amount of product and verified as less than 10% of total substrate cleavage. Specific activity (pmol product/min/pmol GAA) was calculated by dividing the amount of product by the reaction time and molar amount of GAA.

Figure 2:
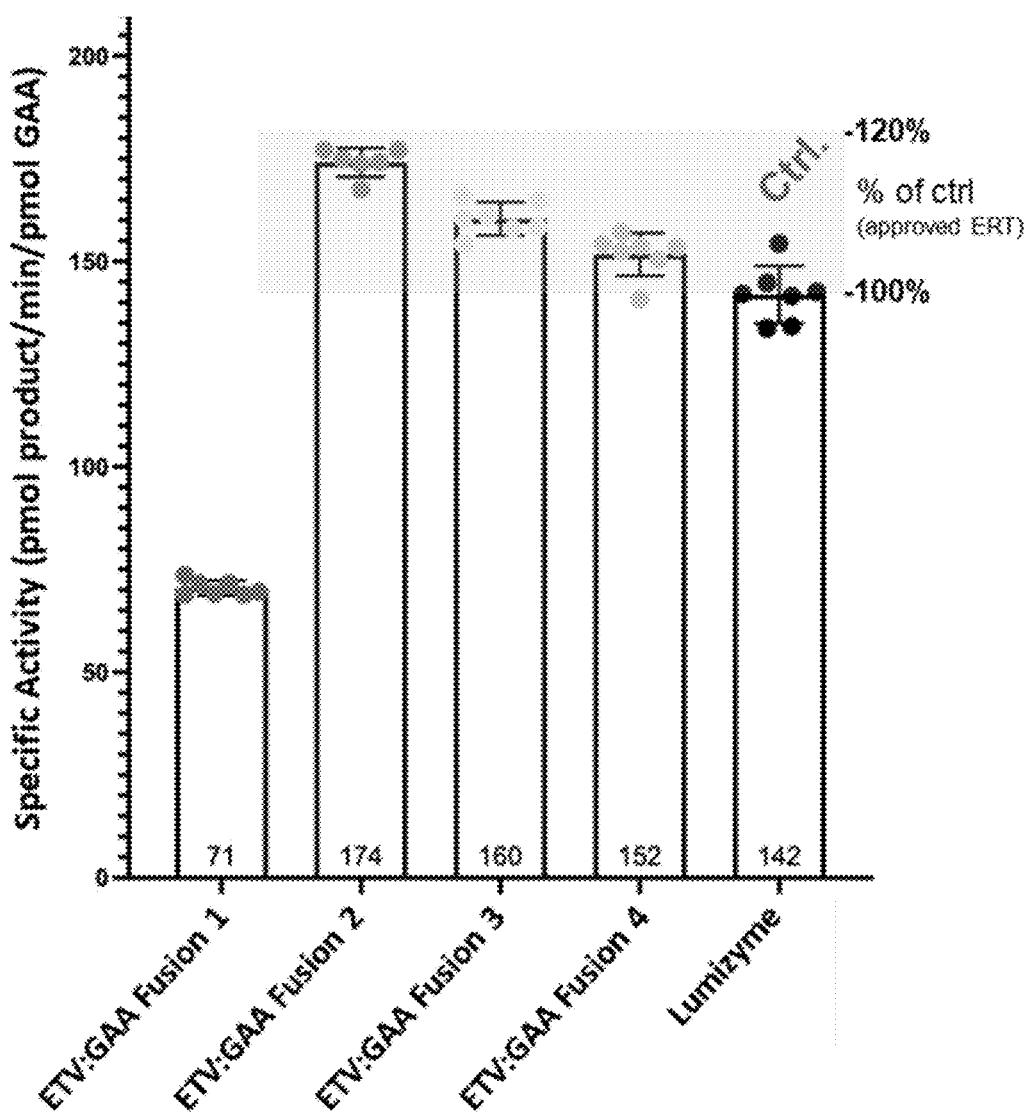
FIG. 2. In vitro evaluation of enzymatic activity of ETV:GAA fusion proteins and alglucosidase alfa (LUMI-ZYME®).

The in vitro enzymatic activity assay demonstrated that GAA-Fc fusion proteins were active and were similar between ETV:GAA Fusions 2, 3, and 4 (FIG. 2). ETV:GAA fusion proteins 2, 3, and 4 had specific activity that was comparable or exceeded the specific activity of LUMIZYME®.

The cellular activity of GAA-Fc fusion proteins was also examined in fibroblasts from Pompe disease patients and healthy controls using fluorescence quantification of hydrolyzed cellular glycogen to assess substrate correction. Briefly, Pompe disease fibroblasts and healthy fibroblasts were cultured in 96-well plates in media (MEM+15% FBS+ Non-essential amino acids (NEAA)) to a cell density of 10,000 cells/well. GAA-Fc fusion proteins were then added to each well in a 3-fold serial dilution concentration range starting from 300 nM for a total of 11 dose points. Healthy control fibroblasts were also plated to determine baseline glycogen levels. Parallel plates were used for total protein estimation. Seventy-two (72) hours after addition of protein, the media was removed and replaced with DMEM media without glucose. Twenty-four hours later, cells were collected, lysed, and prepared for glycogen estimation using a glycogen estimation kit (Sigma #MAK016) according to manufacturer's suggested procedure. Briefly, after removal of glucose (-) medium, cells were washed in ice-cold PBS and then resuspended in ddH2O. An equivalent volume of hydrolysis buffer from the kit was added, followed by incubation at 95° C. for 5 mins to denature proteins. Lysates were spun down at room temperature for 10 min to remove debris. The lysates were then hydrolyzed to free glucose with amyloglucosidase (from kit) for 30 mins. Following hydrolysis to glucose, development enzyme (glucose oxidase) along with a fluorescent peroxide substrate (from kit) were added to the lysate solution, and sample mixtures were transferred to a fresh 96-well plate. After 30 mins incubation at room temperature, fluorescence generated from glucose oxidation was measured by fluorescence plate reader (Biotek Neo2). Total protein levels were measured from parallel plates by BCA assay. Kit-provided glycogen standards were used to estimate glycogen concentration. After total protein normalization, results were reported as total glycogen levels/total protein content for each sample. Graphpad Prism software was used to estimate cellular EC50 levels from sample glycogen results.

Figure 3:
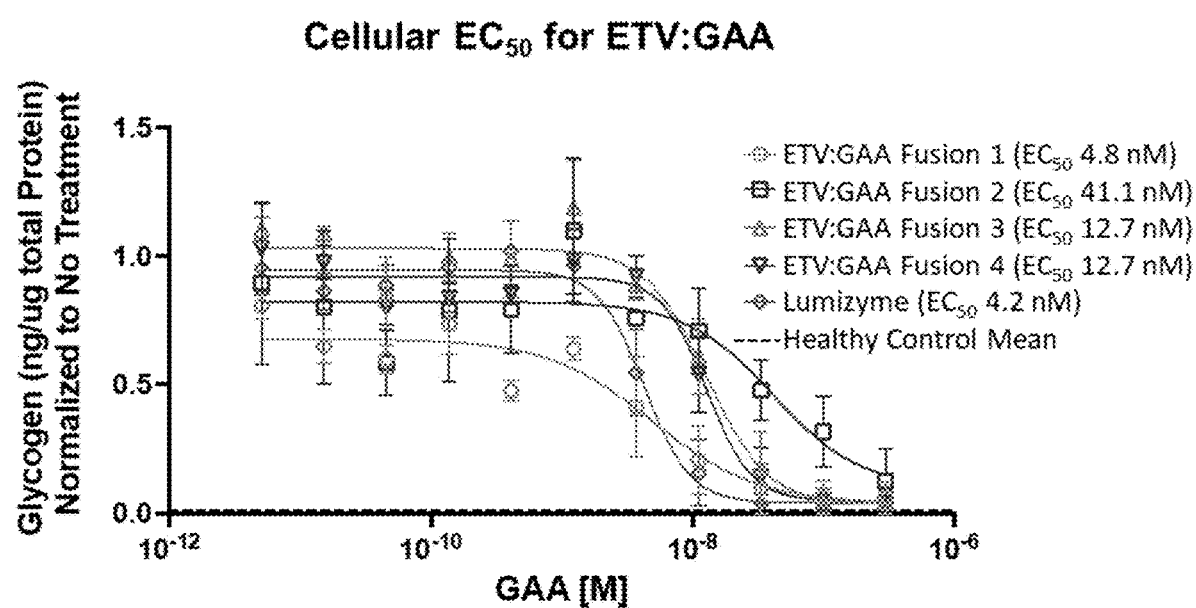
FIG. 3. Evaluation of cellular activity of ETV:GAA fusion proteins as compared to alglucosidase alfa (LUMIZYME®) in fibroblasts from Pompe disease patients using fluorescence quantification of hydrolyzed cellular glycogen.

Pompe disease patient fibroblasts lack GAA activity, leading to an accumulation of glycogen. ETV:GAA Fusion 1 showed comparable potency to LUMIZYME® in Pompe disease patient-derived cells, displaying a low nanomolar cellular $EC_{50}$ (about 4-5 nM) for reducing the accumulation of glycogen (FIG. 3). ETV:GAA Fusions 3 and 4 illustrated slightly weaker cellular potency ($EC_{50}$ of about 12-13 nM) relative to ETV:GAA Fusion 1 and LUMIZYME®, while ETV:GAA Fusion 2 illustrated the weakest cellular potency. Analysis by Western blot indicated that the GAA portion of the ETV:GAA fusion proteins showed processing similar to that of LUMIZYME® when converted to its active form in lysosomes (data not shown).

Product Quality Attributes

Table 2 provides a summary of the product quality attributes of the transiently-expressed fusion proteins.

TABLE 2

Expression and Purification Product Quality Attributes for ETV:GAA Fusion Proteins

| Attribute | ETV:GAA Fusion 1 | ETV:GAA Fusion 2 | ETV:GAA Fusion 3 | ETV:GAA Fusion 4 |
|---|---|---|---|---|
| Expression titer (g/L) | 0.21 | 0.27 | 0.28 | 0.25 |
| % yield (post-Protein A) | 82 | 87 | 80 | 83 |
| % purity (post-Protein A) | 91 | 90 | 90 | 90 |
| % purity (post-CEX) | >98 | >98 | >98 | >98 |
| TfR affinity $K_D$ | 251 nM | 260 nM | 282 nM | 271 nM |
| M6P (mol/mol) | 0.51 | 0.17 | 0.22 | 0.28 |

As described above, the measured human TfR affinities for ETV:GAA Fusions 1, 2, 3 and 4 were comparable ($K_D$ of about 250-300 nM). The expression titers for all four ETV:GAA fusion proteins were similar and greater than about 200 mg/L. Post protein A chromatography purification recovery of ETV:GAA Fusions 1, 2, 3, and 4 was evaluated. Analysis of post-protein A pools of all structures illustrated at least 70% purity (as measured by HPLC-SEC). When the post-protein A pools of all ETV:GAA structures underwent cationic exchange chromatography (CEX) for further polishing (as described in Example 1), post-CEX pools of all structures achieved purity levels of >98% (as measured by HPLC-SEC). Thus, expression of the ETV:GAA fusion proteins resulted in high titers and homogeneity. Finally, the mannose-6-phosphate (M6P) content of all the fusion proteins was low (below 1 mol/mol).

Measurement of Mannose-6-phosphate (M6P) Content

The M6P content of a given protein sample was measured by liquid chromatography-mass spectrometry analysis. Each sample was spiked with stable isotope labeled $(SIL)^{13}C_6$ mannose-6-phosphate (M6P-IS, Omicron Biochemicals Inc, Cat #, MAN-05) as an internal standard. Protein samples were added to trifluoroacetic acid solution and hydrolyzed at 95° C. The samples were subsequently dried under nitrogen and resuspended in acetonitrile:water (20:80, v:v) and analyzed by LC-MS/MS.

M6P analysis was performed by liquid chromatography on UHPLC Vanquish (Thermo Scientific, CA, USA) coupled to a Q Exactive Orbitrap electrospray ionization mass spectrometer (Thermo Scientific, CA, USA). Samples were injected on a BEH Amide column 1.7 µm, 2.1×150 mm (Waters), at 65° C. The LC gradient consisted of mobile phase of (A) water with 0.1% formic acid and (B) acetonitrile with 0.1% formic acid. Data was collected using parallel reaction monitoring (PRM) acquisition under negative mode. AUC ratios of M6P/M6P-IS precursor were used to calculate the molecular amount of M6P released from protein, and the mole of M6P per mole of protein was obtained for each sample.

Example 3: Pharmacokinetic Studies of ETV:GAA Fusion Proteins

The pharmacokinetics of ETV:GAA fusion proteins in TfR knock in (referenced herein as "TfR$^{mu/hu}$ KI" or "TfR$^{mu/hu}$") mice were evaluated. TfR$^{mu/hu}$ KI mice were generated as described in International Patent Publication No. WO 2018/152285 using CRISPR/Cas9 technology to express human Tfrc apical domain within the murine Tfrc gene; the resulting chimeric TfR was expressed in vivo under the control of the endogenous promoter. Briefly, 6-8 week old male TfR$^{mu/hu}$ KI mice (n=3 per cohort) were dosed with a single dose (40 mg/kg or 20 mg/kg) of ETV:GAA fusion protein or alglucosidase alfa, and the concentration of GAA enzyme was measured in serum, quadricep muscle, and brain tissue. A non-TfR binding Fc:GAA protein was also included for comparison in the 20 mg/kg single-dose pharmacokinetic study. Total GAA enzyme levels were measured using a sandwich ELISA-based assay at t=0.25, 1, 2, 4, 8, and 24 hours post-dose for serum PK, and at t=2, 8, 24 hours post-dose for quadricep muscle and brain PK. The GAA-Fc fusion proteins that were used in the analysis are described above and were prepared in accordance with Example 1. For measurement of total GAA enzyme levels, a polyclonal mouse anti-human GAA antibody was coated onto a MULTI-ARRAY® 96-well plate (Meso Scale Diagnostics L15XA-3) overnight. The plate was blocked with Blocker™ Casein in PBS (ThermoFisher 37528), and then incubated with diluted serum, quadricep lysate or brain lysate. Next, a Ruthenium-conjugated polyclonal mouse anti-human GAA antibody was added for detection. 2× Read buffer T with surfactant (Meso Scale Diagnostics R92TC-1) was added to each well, and plates were loaded into the MSD reader. The standard curves were based on the individual constructs and were fit using a four-parameter logistic curve. The results are illustrated in FIGS. 4A-4C (40 mg/kg single-dose PK) and 5A-5C (20 mg/kg single-dose PK).

Figure 4A:
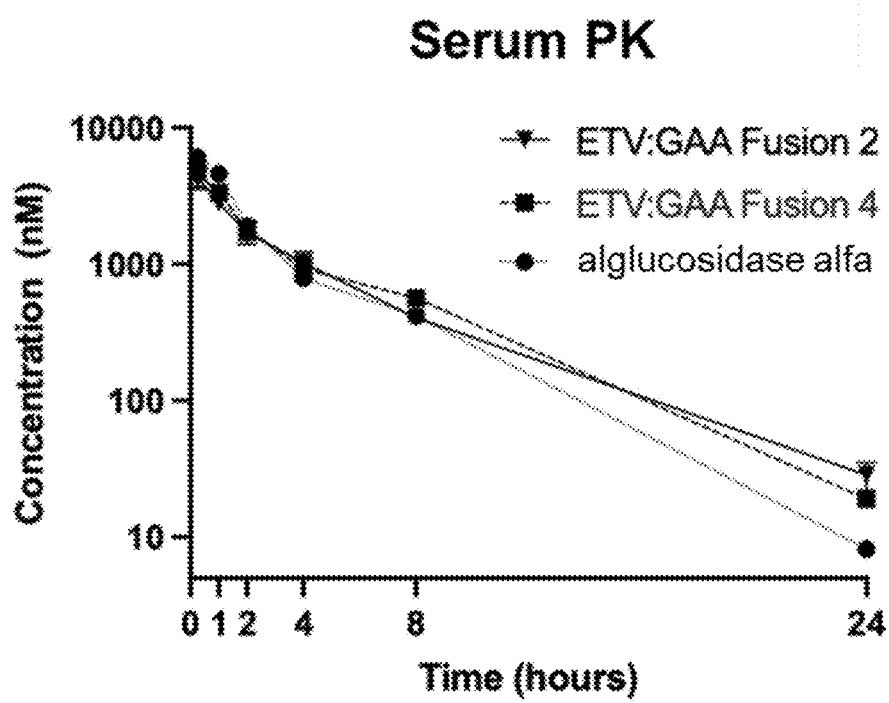
FIGS. 4A-4C. Evaluation of single-dose pharmacokinetics of ETV:GAA fusion proteins and alglucosidase alfa (LUMIZYME®) in TfR knock in mice ("TfR$^{mu/hu}$") in serum (FIG. 4A), quadricep muscle tissue (FIG. 4B), and brain tissue (FIG. 4C). All mice were dosed with 40 mg/kg of fusion protein or alglucosidase alfa. Numbers in parentheses next to symbols indicate number of mice for which GAA levels were evaluated if different from the total number in the cohort.
Figure 4B:
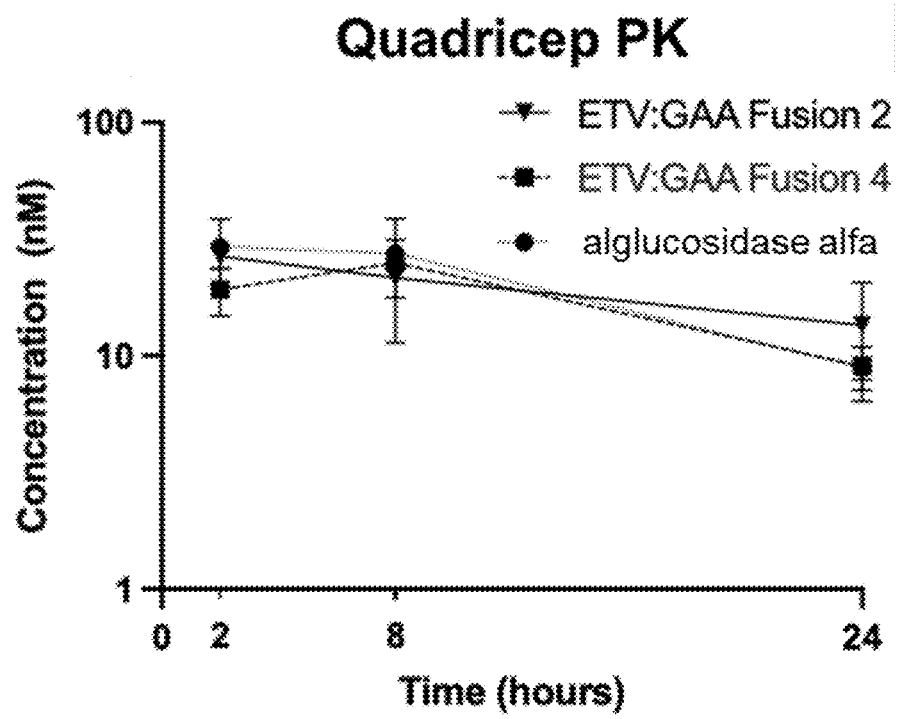
Figure 4C:
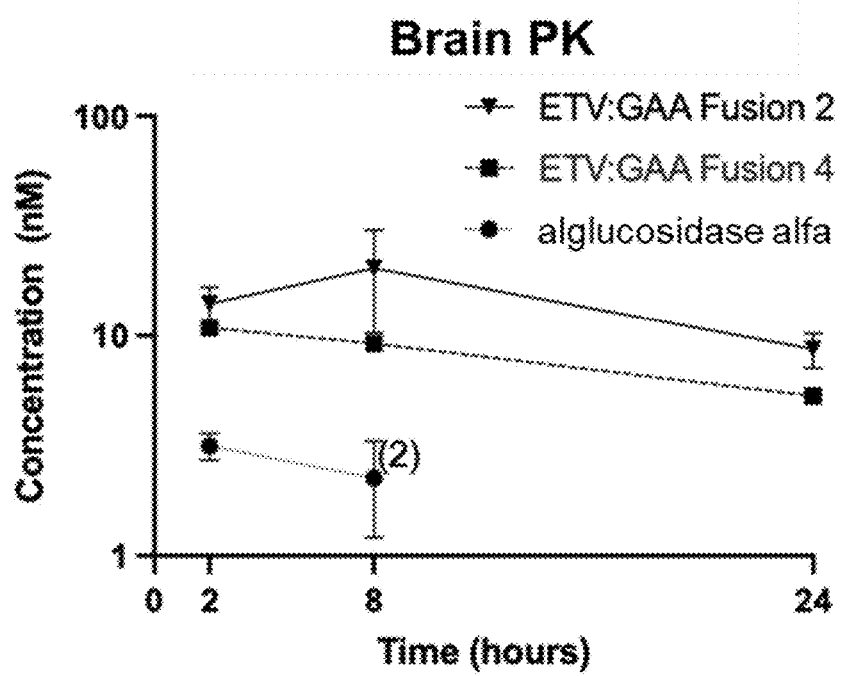

As illustrated in FIG. 4A, at a single dose of 40 mg/kg, serum exposure of ETV:GAA Fusions 2 and 4 were similar up to 24-hours post-dose, while alglucosidase alfa showed faster clearance relative to the two ETV:GAA fusion proteins. In the quadricep tissue (FIG. 4B), similar kinetics of exposure were observed between the ETV:GAA fusion proteins and alglucosidase alfa. In contrast, in the brain, the ETV:GAA fusion proteins illustrated about 6- to 10-fold improved brain exposure (about 10-20 nM absolute concentration) relative to that of alglucosidase alfa.

Figure 5A:
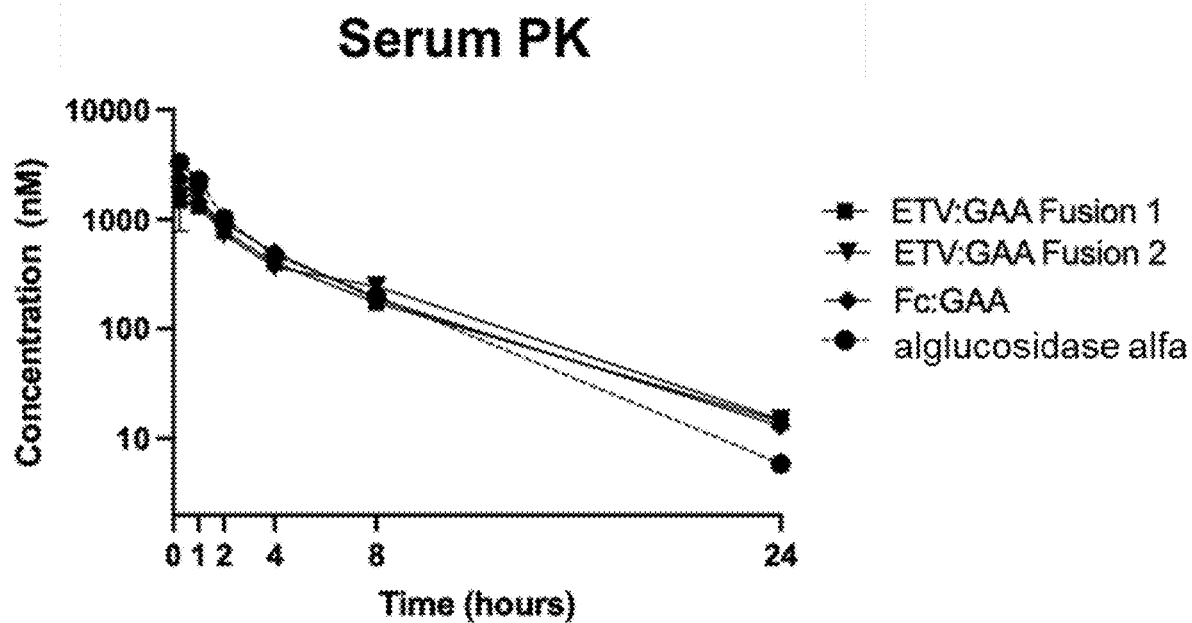
FIGS. 5A-5C. Evaluation of single-dose pharmacokinetics of ETV:GAA fusion proteins and alglucosidase alfa (LUMIZYME®) in TfR knock in mice ("TfR$^{mu/hu}$") in serum (FIG. 5A), quadricep muscle tissue (FIG. 5B), and brain tissue (FIG. 5C). All mice were dosed with 20 mg/kg of fusion protein or alglucosidase alfa. Numbers in parentheses next to symbols indicate number of mice for which GAA levels were evaluated if different from the total number in the cohort.
Figure 5B:
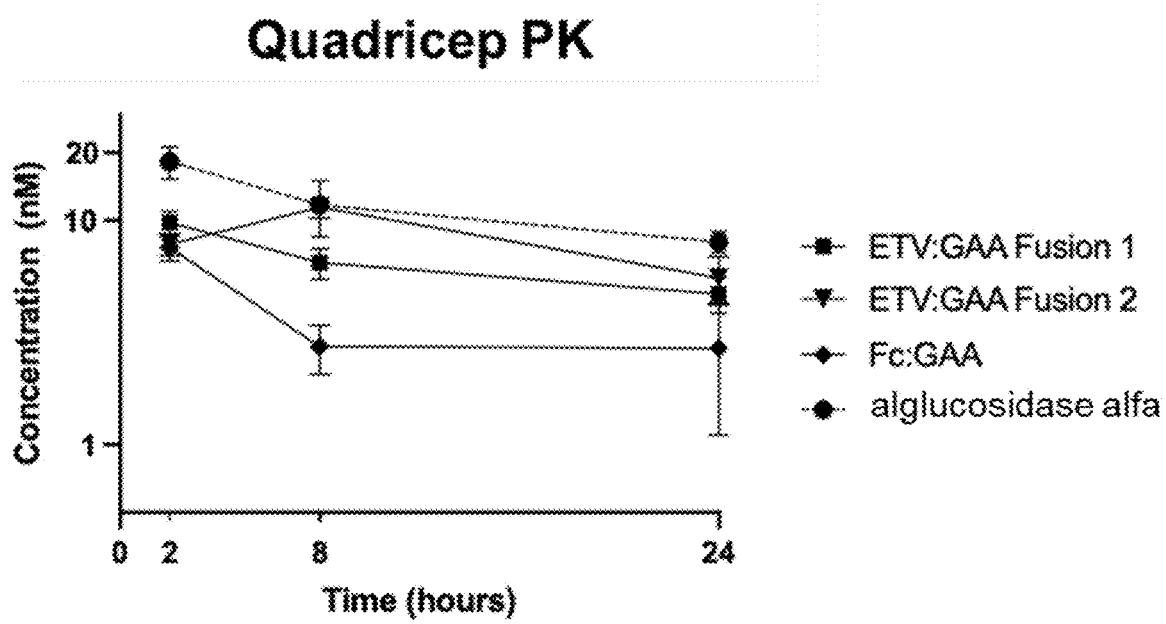
Figure 5C:
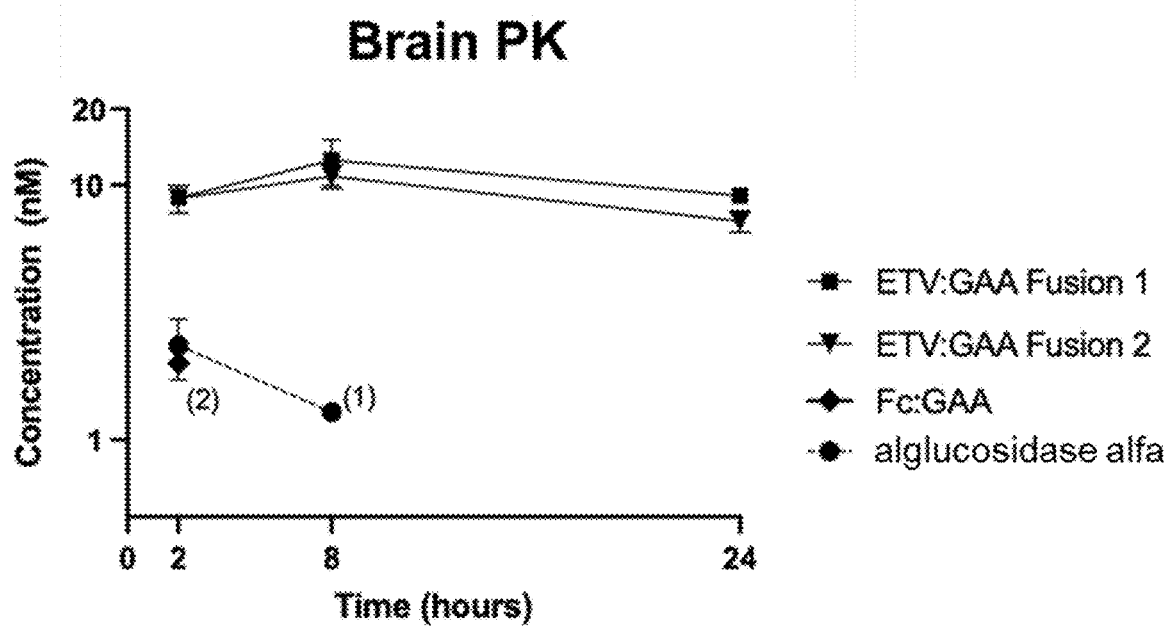

Similar trends were observed in single dose pharmacokinetic studies at a dose 20 mg/kg (FIGS. 5A-5C), which included dosing with a non-TfR binding Fc:GAA fusion structure ("Fc:GAA"). Serum exposure of ETV:GAA Fusion 1, ETV:GAA Fusion 2, and Fc:GAA were similar up to 24-hours post-dose, while that of alglucosidase alfa illustrated faster clearance relative to the ETV:GAA and Fc:GAA structures (FIG. 5A). In the quadricep tissue (FIG. 5B), similar kinetics of exposure were observed between the ETV:GAA fusion proteins and alglucosidase alfa, while quadricep exposure of Fc:GAA protein was lower. In the brain (FIG. 5C), ETV:GAA fusion proteins illustrated better brain uptake relative to alglucosidase alfa and the non-TfR binding Fc:GAA protein.

Collectively, the results illustrate that the ETV:GAA fusion protein structures achieve improved brain exposure relative to a non-TfR binding Fc:GAA structure and a standard-of-care ERT enzyme (alglucosidase alfa).

Additional Experimental Methods

ETV:GAA Fusions 1, 2, and 4 were expressed and purified as described in Example 1. Alglucosidase alfa was obtained from a commercial source (Sanofi Genzyme).

A non-TfR-binding GAA-Fc fusion protein ("Fc:GAA") was generated, which comprises an Fc polypeptide having the sequence of SEQ ID NO:25 and an GAA-Fc fusion polypeptide having the sequence of SEQ ID NO:52. The GAA-Fc fusion protein may also be further processed during cell culture production, such that the Fc polypeptide has the sequence of SEQ ID NO:26 and/or the GAA-Fc fusion polypeptide has the sequence of SEQ ID NO:53. Thus, as used herein, the term "Fc:GAA" may be used to refer to protein molecules having unprocessed sequences (i.e., SEQ ID NOs:25 and 52); protein molecules comprising one or more processed sequences (i.e., selected from SEQ ID NOs: 26 and 53); or to a mixture comprising processed and unprocessed protein molecules.

Example 4: A Comparative Study of ETV:GAA Fusion 1 with Alglucosidase Alfa in a Disease Model of Pompe Disease The pharmacodynamic response of ETV:GAA Fusion 1 was compared to a standard-of-care enzyme replacement therapy, alglucosidase alfa (LUMIZYME®), in a mouse model of Pompe disease.

Results

Figure 6A:
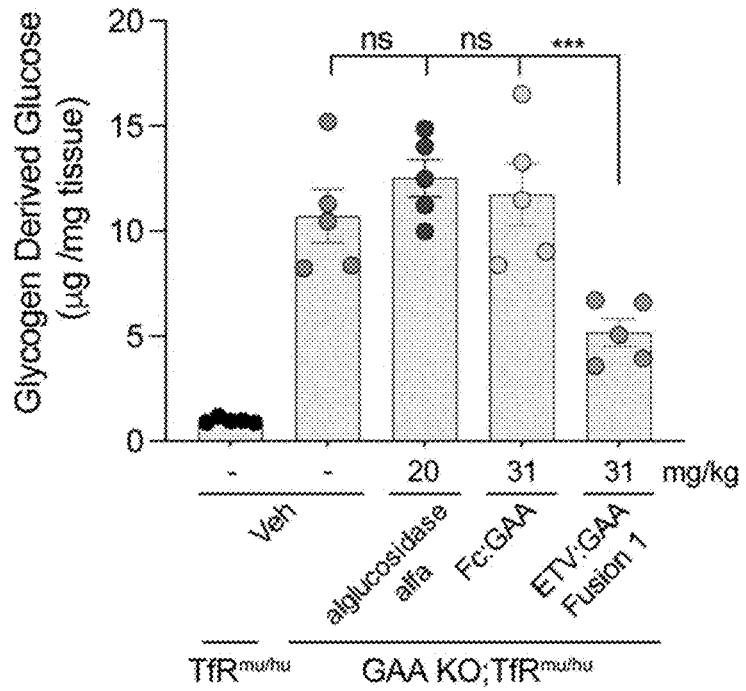
FIGS. 6A-6B. Evaluation of pharmacodynamic response at seven (7) days post-single dose in quadricep muscle tissue (FIG. 6A) and brain tissue (FIG. 6B) in a comparative study carried out in healthy and disease mouse models of Pompe disease. Mice were dosed with 31 mg/kg of fusion protein or 20 mg/kg alglucosidase alfa. The healthy mouse model is represented by TfR knock in mice ("TfR$^{mu/hu}$") and the disease mouse model is represented by TfR knock in mice in which the gene for GAA has been knocked out ("GAA KO; TfR$^{mu/hu}$") Graphs display mean±SEM and p values: one-way ANOVA Dunnett's multiple comparison test; p≤0.01, *p≤0.001.
Figure 6B:
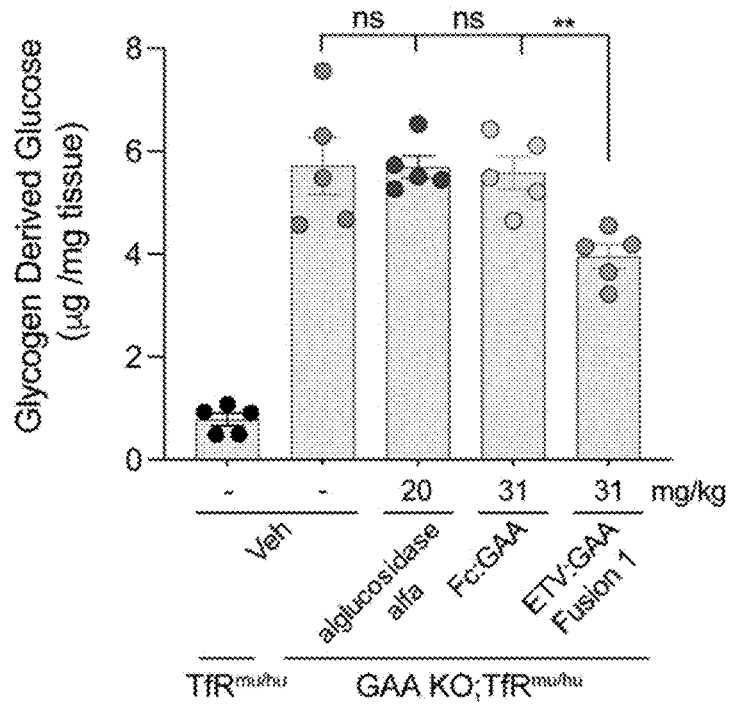
Figure 7A:
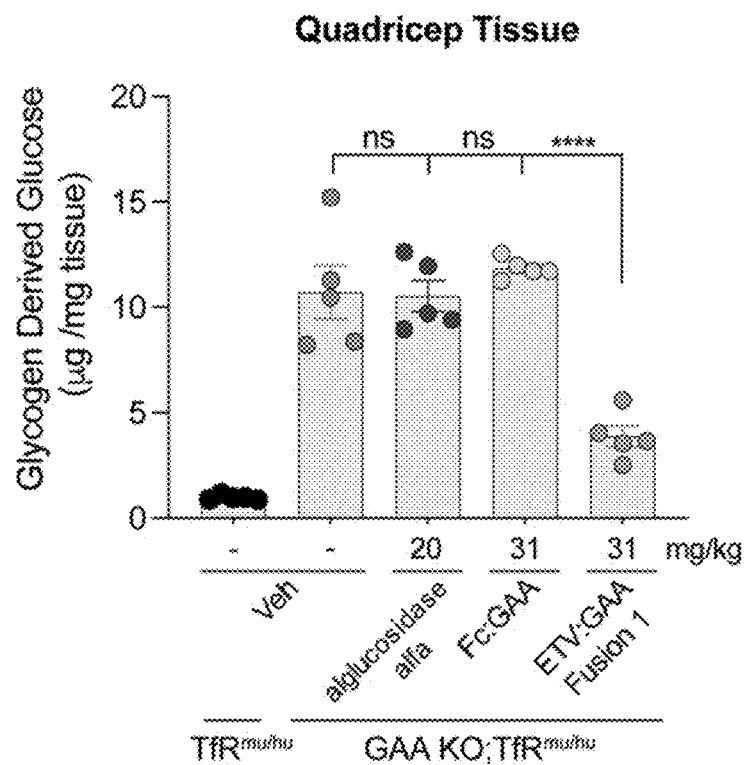
FIGS. 7A-7B. Evaluation of pharmacodynamic response at 14 days post-single dose in quadricep muscle tissue (FIG. 7A) and brain tissue (FIG. 7B) in a comparative study carried out in healthy and disease mouse models of Pompe disease. Mice were dosed with 31 mg/kg of fusion protein or 20 mg/kg alglucosidase alfa. The healthy mouse model is represented by TfR knock in mice ("TfR$^{mu/hu}$") and the disease mouse model is represented by TfR knock in mice in which the gene for GAA has been knocked out ("GAA KO; TfR$^{mu/hu}$") Graphs display mean±SEM and p values: one-way ANOVA Dunnett's multiple comparison test; ****p≤0.0001.
Figure 7B:
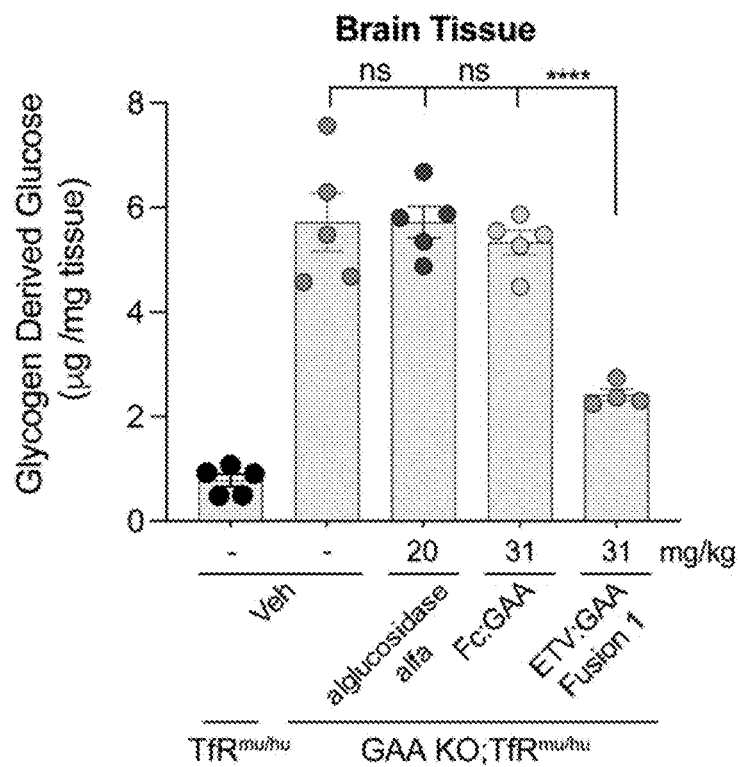

In this study, ETV:GAA Fusion 1 and alglucosidase alfa were compared in how well the proteins reduced glycogen accumulation in the muscle (quadricep) and brain tissue from GAA KO; TfR$^{mu/hu}$ KI mice after a single intravenous (IV) dose. ETV:GAA Fusion 1 was administered to the mice as an equimolar dose to that of alglucosidase alfa (31 mg/kg), while alglucosidase alfa was administered at a dose consistent with a clinically relevant dose for treatment (20 mg/kg). A separate non-TfR binding Fc:GAA construct was also administered as a control (31 mg/kg). As illustrated in FIGS. 6A and 6B and Table 3, at 7 days following a single dose, ETV:GAA protein was able to reduce glycogen-derived glucose levels in the quadricep and brain tissue by about 52% and 31%, respectively, relative to vehicle-treated GAA KO; TfR$^{mu/hu}$ KI mice. At 14 days following a single dose, ETV:GAA protein was able to reduce glycogen-derived glucose levels in the quadricep and brain tissue by about 64% and 58%, respectively, relative to vehicle-treated GAA KO; TfR$^{mu/hu}$ KI mice (FIGS. 7A and 7B; Table 3). In comparison, non-TfR binding Fc:GAA and alglucosidase alfa did not significantly reduce glycogen-derived glucose levels in these tissues at either 7- or 14-days post single dose. The M6P content of the administered proteins (ETV:GAA Fusion 1, Fc:GAA, and alglucosidase alfa) was comparable (0.6 mol/mol).

TABLE 3

Percent reduction in glycogen levels after single IV dose administration compared to vehicle-treated GAA KO; TfR$^{mu/hu}$ KI mice.

| Treatment | Dose [mg/kg] | 7 days post-dose | | 14-days post-dose | |
|---|---|---|---|---|---|
| | | Quadricep Tissue Glycogen reduction | Brain Tissue Glycogen reduction | Quadricep Tissue Glycogen reduction | Brain Tissue Glycogen reduction |
| Alglucosidase alfa | 20 | N/S | N/S | N/S | N/S |
| Fc:GAA | 31 | N/S | N/S | N/S | N/S |
| ETV:GAA Fusion 1 | 31 | 52% | 31% | 64% | 58% |

The data in FIGS. 6(A, B) and 7(A, B) represents approximate mean amounts+/−standard error of the mean. The results demonstrate that ETV:GAA robustly reduced glycogen accumulation in muscle and brain tissue, and this reduction represented an improvement relative to a standard-of-care ERT treatment and non-TfR binding Fc:GAA treatment. In addition, the pharmacodynamic response to ETV:GAA treatment was better at 14-days post dose relative to that at 7-days post dose. The superior improvement in glycogen reduction in muscle was observed despite comparable M6P content across all proteins, indicating that the linking of GAA enzyme to a TfR binding component could potentially overcome trafficking limitations imposed by low M6P content.

Experimental Methods

ETV:GAA Fusion 1 was expressed and purified as described in Example 1. Alglucosidase alfa was obtained from a commercial source (Sanofi Genzyme).

A non-TfR-binding GAA-Fc fusion protein, termed "Fc:GAA", was generated as described in Example 3.

The mannose-6-phosphate (M6P) content of all proteins was measured as described in Example 2.

The Pompe disease mouse model used in this study is a mouse model in which the gene encoding GAA is knocked-out while also harboring the human TfR apical domain knocked into the murine TfR (referred to herein as "GAA KO; TfR$^{mu/hu}$ KI" or "GAA KO; TfR$^{mu/hu}$" mice). TfR$^{mu/hu}$KI mice, also referred herein as TfR$^{mu/hu}$ mice, were generated as described in Example 3. GAA KO mice, also known as 6$^{neo}$ or PD mice, were obtained from The Jackson Laboratories (JAX stock #004154). Briefly, TfR$^{mu/hu}$ KI mice were bred to homozygous GAA KO mice to generate homozygous GAA KO mice in a TfR$^{mu/hu}$ KI homozygous background. Mice used in this study were mixed sex and housed under a 12 hour light-dark cycle with ad libitum access to food (#25502, irradiated; LabDiet) and water.

GAA KO; TfR$^{mu/hu}$ KI mice were administered a single dose of ETV:GAA Fusion 1, Fc:GAA, or alglucosidase alfa via intravenous injection, and pharmacodynamic responses were assessed. In particular, the effect of peripheral administration of the proteins on glycogen levels in muscle and brain tissues of GAA KO; TfR$^{mu/hu}$ KI mice was determined using approximately 7-8 month-old GAA KO; TfR$^{mu/hu}$ KI mice injected intravenously (i.v.) with vehicle, ETV:GAA fusion protein (31 mg/kg body weight), Fc:GAA fusion protein (31 mg/kg body weight), or alglucosidase alfa (20 mg/kg body weight) (n=4-5/group). Approximately 6-month-old littermate TfR$^{mu/hu}$ KI mice (non-disease mice) injected i.v. with vehicle were used as controls. All animals were sacrificed 7 days or 14 days post single dose. Muscle and brain tissue were collected and flash-frozen on dry ice.

Muscle and brain tissue were analyzed for glycogen levels as follows. Briefly, 20 µg portions of tissue were cut and homogenized in deionized water using TissueLyser for 2×3 min sequences at 30 Hz. The tissue lysate was then sonicated with 20 cycles of one-second on and one-second off pulses with a sonicator. Lysates were transferred to individual 1.5-mL protein low-bind tubes and centrifuged at 4° C. The supernatant was transferred to fresh tubes and digested with amyloglucosidase as follows. In a 96-well plate, 50 uL of sample was combined with 10 µL of internal standard (1 mg/mL of U-13C6 D-glucose) and 10 µL of 0.5 mg/mL amyloglucosidase (500 U) in 10 mM potassium phosphate (pH 4.2). Fifty (50) µL of standard (bovine liver glycogen ranging from 25-750 µg/mL), QC standards (400, 175 and 40 µg/mL of glycogen bovine liver glycogen), and blanks were pipetted into the 96-well plate and digested in the same manner. The plate was centrifuged at 1000 rpm for 1 min and incubated at 60° C. for 1 hour with shaking (300 rpm). Amyloglucosidase (enzyme) was deactivated by heating the plate to 100° C. for 5 min with shaking (450 rpm).

The digestion and inactivation step was followed by derivatization, where 100 µL of 0.1M PMP (3-Methyl-1-phenyl-2-pyrazoline-5-one (PMP), (Catalog #M70800-500G, Sigma Aldrich, St Louis, MO, USA) was added to the samples and placed at 70° C. for 2.5 hours followed by 5 min of cooling at 4° C. Four hundred (400) µL of 200 mM formic acid was added to each sample followed by three extraction washes (addition and removal) with 300 µL chloroform. After the last wash with chloroform, 100 µL of aqueous (top) solution was transferred to a new plate and dried. The samples were reconstituted in 9:1 water:acetonitrile with 0.1% formic acid and mixed at 1500 rpm for 2 mins before proceeding to LC/MS analysis. Quantification was carried out by an LC/MS method adapted from Fuller et al. (2012. *Analytical Biochemistry* 421:759-763).

Example 5: Generation of Stable Cell Pools for Expression of GAA-Fc Fusion Proteins Stable Chinese Hamster Ovary (CHO) cell pools of ETV:GAA Fusions 1, 2, 3, and 4 (Example 1) were generated as described below using different ratios of the following during transfection: (a) the DNA plasmid encoding the TfR-binding modified Fc polypeptide, and (b) the DNA plasmid encoding the GAA-Fc (or Fc-GAA) fusion polypeptides. Chain ratios in the tables below are provided as a mass ratio of (a):(b). Table 4 illustrates the titers resulting from the different chain ratio conditions for exemplary pools for ETV:GAA Fusions 1, 2, 3, and 4 during stable pool generation.

TABLE 4

Stable pool titers of ETV:GAA fusion proteins

| Fusion Protein | Chain Ratio | Titer (mg/L) |
|---|---|---|
| ETV:GAA Fusion 1 | 1:1 | 11.6 |
| | 1:2 | 31.2 |
| | 1:3 | 9.71 |

TABLE 4-continued

Stable pool titers of ETV:GAA fusion proteins

| Fusion Protein | Chain Ratio | Titer (mg/L) |
|---|---|---|
| ETV:GAA Fusion 2 | 1:1 | 83.9 |
|  | 1:2 | 8.67 |
|  | 1:3 | 54.8 |
| ETV:GAA Fusion 3 | 1:1 | 488 |
|  | 1:2 | 335 |
|  | 1:3 | 385 |
| ETV:GAA Fusion 4 | 1:1 | 356 |
|  | 1:2 | 346 |
|  | 1:3 | 244 |

The results show that low titers were produced from the stable pools for N-terminal GAA-Fc fusion proteins (ETV:GAA Fusions 1, 2). In contrast, high titers were achieved from the stable pools for C-terminal GAA-Fc fusion proteins (ETV:GAA Fusions 3, 4).

In addition to poor titer, material produced from the stable pools for N-terminal GAA-Fc fusion proteins suffered from low purity and aggregation of protein (high molecular weight species, HMWS) as measured by analytical size exclusion chromatography (a-SEC). Table 5 shows a representative set of data for ETV:GAA Fusion 1.

TABLE 5

Stable pool titers and purity of ETV:GAA Fusion 1

| Selection Stringency | Chain Ratio | Titer (mg/L) | a-SEC (post-ProA) | | |
|---|---|---|---|---|---|
| | | | HMWS (%) | Main Peak/Fusion Protein (%) | LMWS (%) |
| High | 1:1 | 58 | 54.2 | 38.2 | 7.6 |
|  | 1:2 | 71 | 60.1 | 37.1 | 2.8 |
|  | 1:3 | 32 | 40.0 | 45.8 | 14.1 |
| Medium | 1:1 | 158 | 60.1 | 38.5 | 1.4 |
|  | 1:2 | 24 | 43.2 | 50.0 | 6.8 |
|  | 1:3 | 17 | 40.3 | 50.7 | 9.1 |

HMWS: High molecular weight species (e.g., aggregated protein)
LMWS: Low molecular weight species (e.g., protein fragments)

Figure 8:
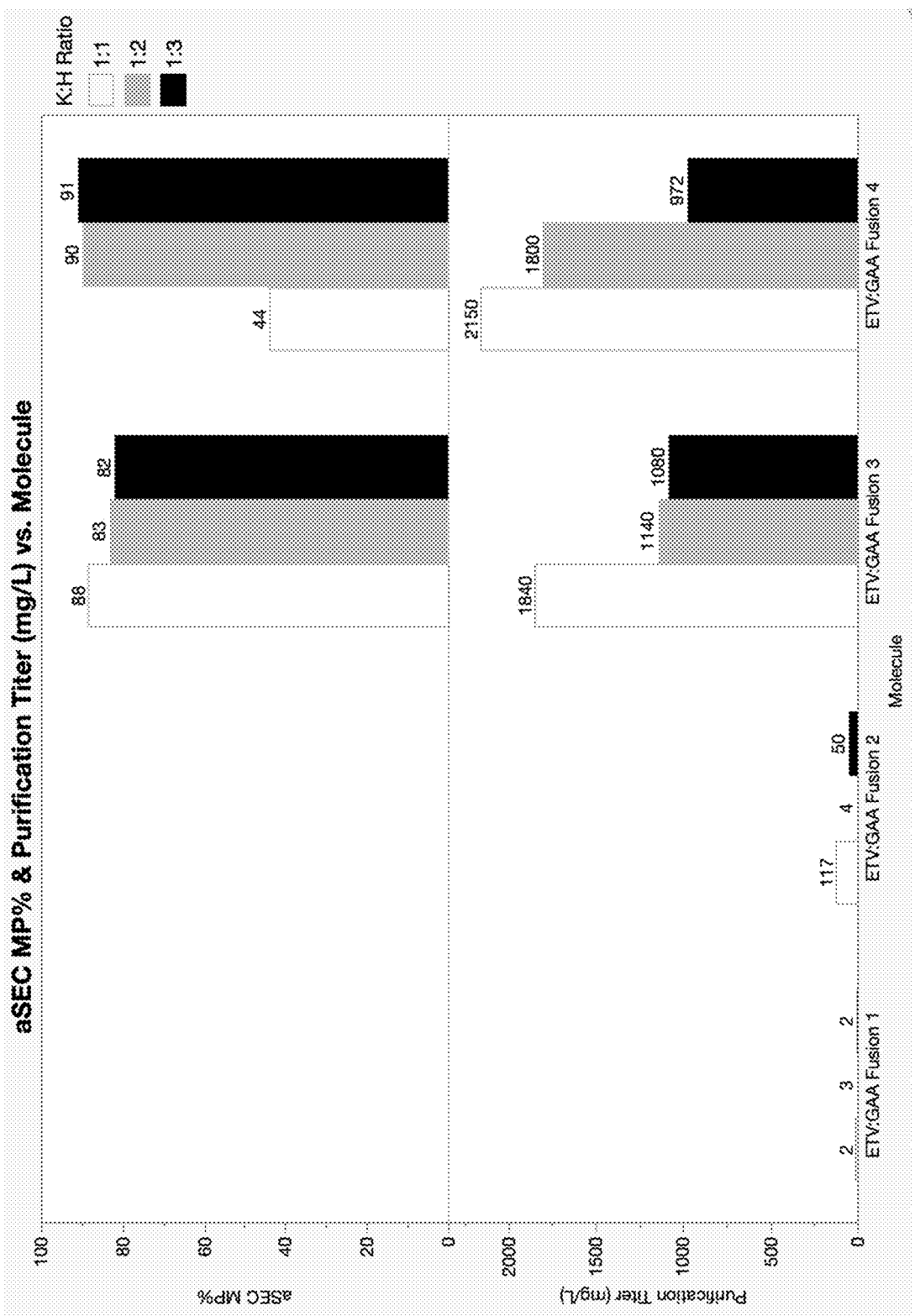
FIG. 8. Product quality attributes of stable pools for ETV:GAA fusion proteins. Top: Bar graph illustrating percent main peak (MP %) as analyzed by analytical size-exclusion chromatography (aSEC), which represents percent intact fusion protein in the total protein collected from the stable pools. Bottom: Bar graph illustrating purification titer (mg/L) for intact fusion protein.

Product quality attributes for ETV:GAA Fusions 1, 2, 3, and 4 are illustrated in FIG. 8. No meaningful fusion protein yields were obtained from stable pools generated for ETV:GAA Fusions 1 and 2, as indicated by low or non-detectable percentages of main peak/fusion protein percentages in the a-SEC results (FIG. 8, top). In contrast, stable pools generated for ETV:GAA Fusions 3 and 4 produced protein titers of about 1000 mg/L or more (FIG. 8, bottom), and most of the recombinant protein produced from these stable pools had good purity of fusion protein (>80% main peak, FIG. 8, top).

The results collectively illustrate that the N-terminal GAA-Fc fusion proteins produced from stable pool cell lines exhibited poor material quality in terms of low titer and purity, which indicates a difficult path forward for large-scale manufacturing of these particular structures. Due to the difficulty in generating high quality material for the N-terminal FAA-Fc fusion proteins from stable pool cell lines, further studies with C-terminal GAA-Fc fusion proteins were carried out.

Experimental Methods

For stable pool generation, glutamine synthetase-null CHO cells (CHOK1 GS null, Horizon), cells were passaged in chemically defined cell culture medium supplemented with 4 mM L-glutamine every 3-4 days. The cells were maintained in 5% $CO_2$ at 37° C. in a humidified shaking incubator at 135 rpm. The cells were transfected by electroporation with plasmid DNA encoding glutamine synthetase and plasmids encoding the following in various mass ratios of [(a):(b)]: (a) the TfR-binding modified Fc polypeptide, and (b) the GAA-Fc (or Fc-GAA) fusion polypeptides. Selection of cells incorporating the transfected DNA was carried out by culturing the cells in medium lacking L-glutamine. The culture was passaged every 3-4 days in fresh media lacking L-glutamine until recovery (>95% viability) to generate the pool. The pool was subsequently cryopreserved in 92.5% fresh medium and 7.5% dimethyl sulfoxide (DMSO).

For recombinant protein expression, the generated stable pools were inoculated at approximately $0.5 \times 10^6$ cells/mL using chemically defined media in Erlenmeyer flasks. The shake flasks were maintained in 5% $CO_2$ at 37° C. in a humidified shaking incubator at 135 rpm. The cells were supplemented with commercially available feeds and glucose throughout the process. The cultures were routinely sampled for cell viability, cell density, and metabolites. On day 14, the cells were harvested by centrifugation, and titer was measured using Protein A biosensors on the Octet® BLI system (Sartorius). The supernatant was collected and purified by Protein A affinity chromatography as described in Example 1. The purified protein was analyzed by various assays, including size exclusion chromatography (SEC) to investigate product quality.

Where additional purification was carried out, the Protein A pool was diluted 10-fold into 20 mM sodium acetate at pH 5.0 and further purified by cation-exchange chromatography (CEX) over a ResourceQ column (Cytivas). Briefly, after binding, the column was washed with 10 CV of 20 mM sodium acetate and 5 mM NaCl at pH 5.0. Bound proteins were eluted using a linear gradient of 5 mM NaCl to 500 mM NaCl in 20 mM sodium acetate at pH 5.0. Homogeneity of post-CEX purified ETV:GAA was assessed by SDS-PAGE and analytical SEC-HPLC. Fractions with >98% purity were pooled and dialyzed over 20 mM sodium phosphate, 150 mM NaCl, at pH 6.5 overnight.

Example 6: A Comparative Study of ETV:GAA Fusion 5 with Alglucosidase Alfa in a Disease Model of Pompe Disease A C-terminal GAA-Fc fusion protein ("ETV:GAA Fusion 5") was generated and compared to a standard-of-care enzyme replacement therapy, alglucosidase alfa (LUMIZYME®), in a mouse model of Pompe disease.

A GAA-Fc fusion polypeptide was constructed having the sequence of SEQ ID NO:70. The fusion polypeptide comprises (1) a truncated human GAA sequence having the polymorphisms that represent the most common allelic variants in sequenced human populations, fused to (2) the C-terminus of an IgG1 Fc polypeptide sequence with hole and LALAPS mutations. The GAA enzyme is joined to the Fc polypeptide by a GGGGS linker (SEQ ID NO:62), and the N-terminus of the Fc polypeptide includes a portion of an IgG1 hinge region (DKTHTCPPCP; SEQ ID NO:6). The foregoing embodiment may also be referred to as an "Fc-GAA fusion polypeptide."

A "C-terminal monozyme" GAA-Fc fusion protein ("ETV:GAA Fusion 5") was generated, which comprises a TfR-binding modified Fc polypeptide having the sequence of SEQ ID NO:43 and an Fc-GAA fusion polypeptide having the sequence of SEQ ID NO:70. The GAA-Fc fusion protein may also be further processed during cell culture production, such that the TfR-binding modified Fc polypeptide has the sequence of SEQ ID NO:44. Thus, as used herein, the term ETV:GAA Fusion 5 may be used to refer to protein molecules comprising SEQ ID NOs:43 and 70; protein molecules comprising SEQ ID NOs:44 and 70; or to a mixture having protein molecules comprising SEQ ID NOs:43 and 70 and protein molecules comprising SEQ ID NOs:44 and 70.

Results

In this study, the pharmacokinetic profile and pharmacodynamic response of ETV:GAA Fusion 5 and alglucosidase alfa in GAA KO; TfR$^{mu/hu}$ KI mice were compared after a single intravenous (IV) dose. ETV:GAA Fusion 5 was administered to the mice as an equimolar dose to that of alglucosidase alfa (30 mg/kg), while alglucosidase alfa was administered at a dose consistent with a clinically relevant dose for treatment (20 mg/kg). The M6P content of ETV: Fusion 5 was 0.16 mol/mol, while that of alglucosidase alfa was 0.6 mol/mol.

Pharmacokinetic Results.

Figure 9A:
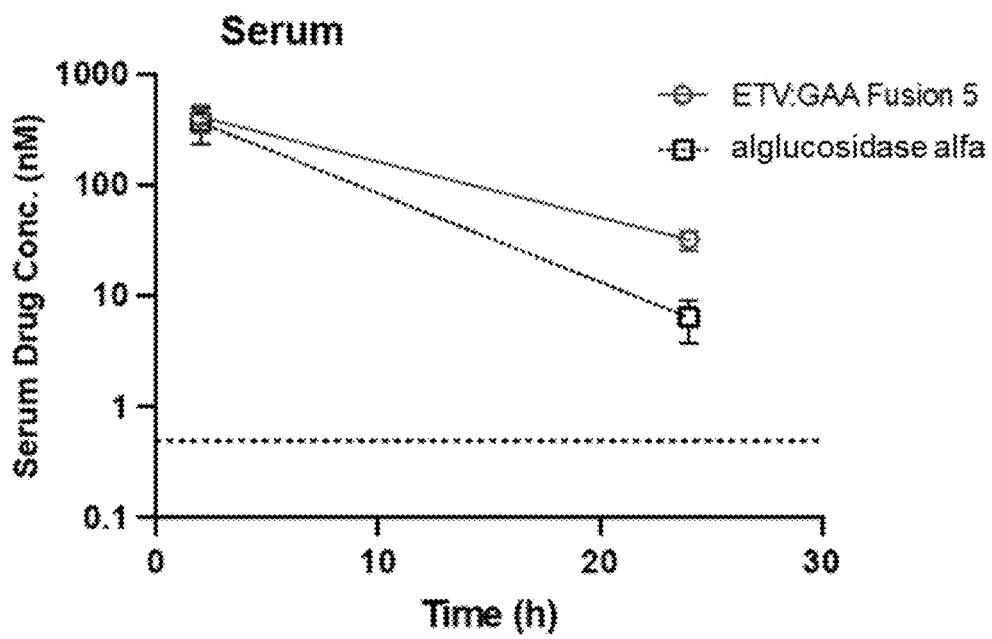
FIGS. 9A-9E. Evaluation of single-dose pharmacokinetics of ETV:GAA Fusion 5 and alglucosidase alfa (LUMIZYME®) in a disease mouse model of Pompe disease (GAA KO; TfR$^{mu/hu}$ KI mice) in serum (FIG. 9A), quadricep muscle tissue (FIG. 9B), brain tissue (FIG. 9C), heart tissue (FIG. 9D), and liver tissue (FIG. 9E). Mice were dosed with 30 mg/kg of fusion protein or 20 mg/kg alglucosidase alfa. N=5 per group. The lower limit of quantitation (LLOQ) for serum is included in FIG. 9A as a horizontal dotted line.
Figure 9B:
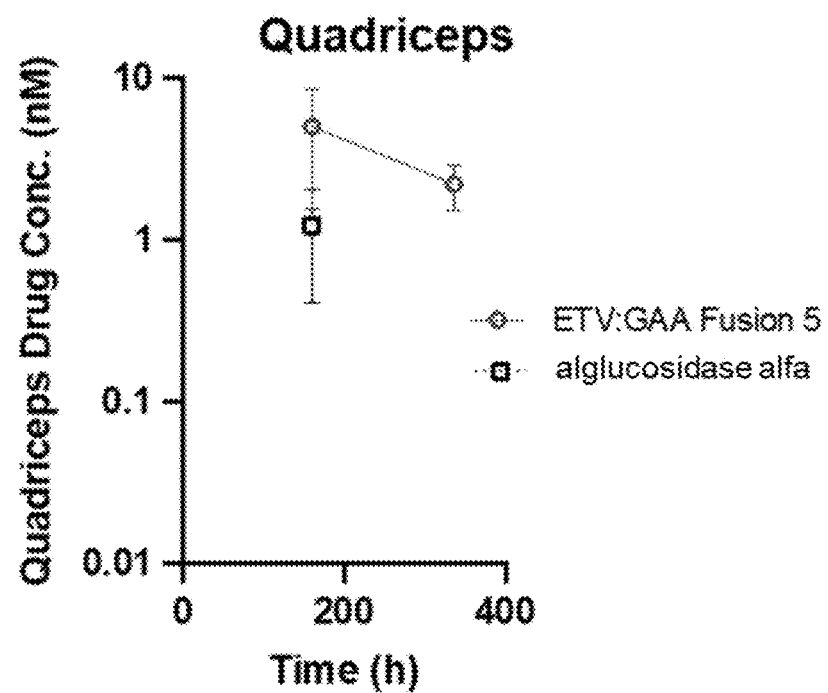
Figure 9C:
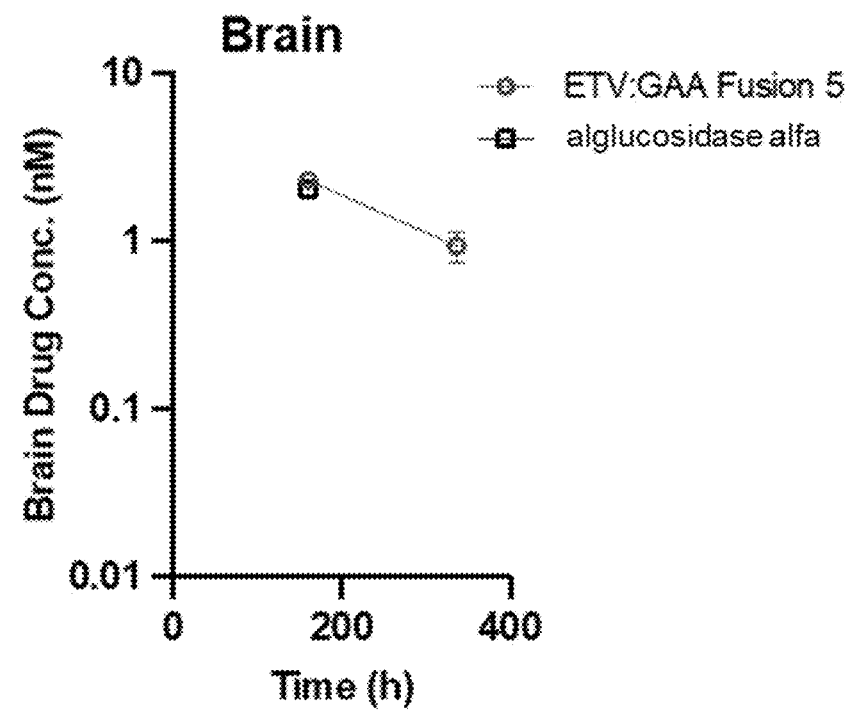
Figure 9D:
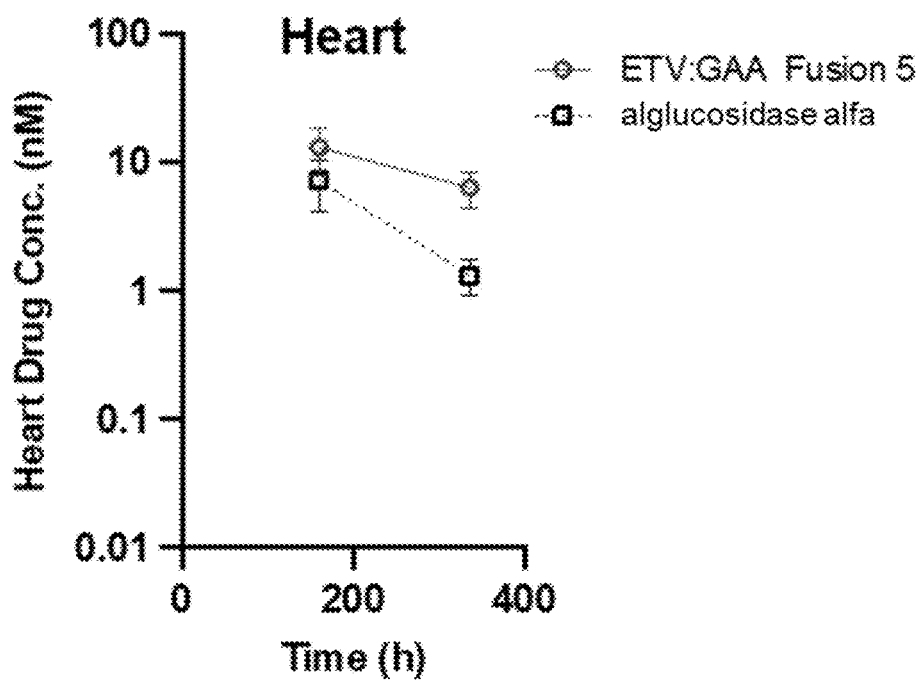
Figure 9E:
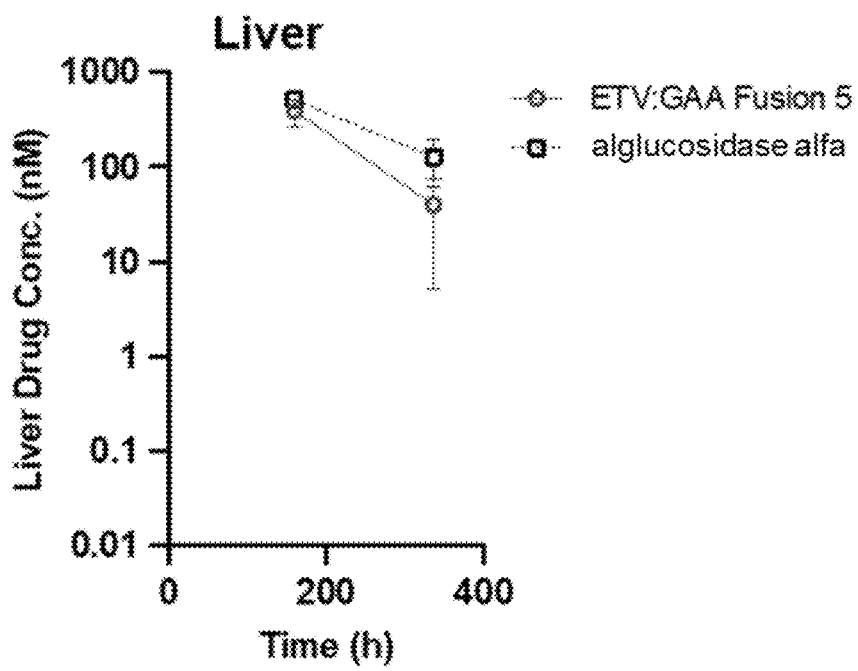

Pharmacokinetic profiles for the tested tissues are provided in FIGS. 9A-9E. As illustrated in FIG. 9A, ETV:GAA Fusion 5 remained stable in serum for up to 24 hours post-dose, while alglucosidase alfa showed faster clearance relative to ETV:GAA Fusion 5. At 24 hours post-dose, the serum concentration of ETV:GAA Fusion 5 was about six-fold greater than that of alglucosidase alfa. In quadricep muscle, brain, and heart tissue (FIGS. 9B-9D), ETV:GAA Fusion 5 concentration was greater than that of alglucosidase alfa at both 7- and 14-days post single dose. In the brain, alglucosidase alfa measurements were only detectable in one of the mice at 7 days post-dose, while no alglucosidase alfa levels were detectable at 14 days post-dose (FIG. 9C). Similarly, in quadricep muscle tissue, no alglucosidase alfa levels were detectable at 14 days post-dose (FIG. 9B). In contrast, concentrations of ETV:GAA Fusion 5 remained detectable out to 14 days post-dose in both brain and quadricep muscle tissues. In liver tissue, alglucosidase alfa showed a trend for higher exposure compared to ETV:GAA Fusion 5 (FIG. 9E). Collectively, the results illustrate that the ETV:GAA Fusion 5 achieved improved tissue exposure relative a standard-of-care ERT enzyme (alglucosidase alfa) in serum, quadricep muscle, brain, and heart tissues.

Pharmacodynamic Results

Figure 10A:
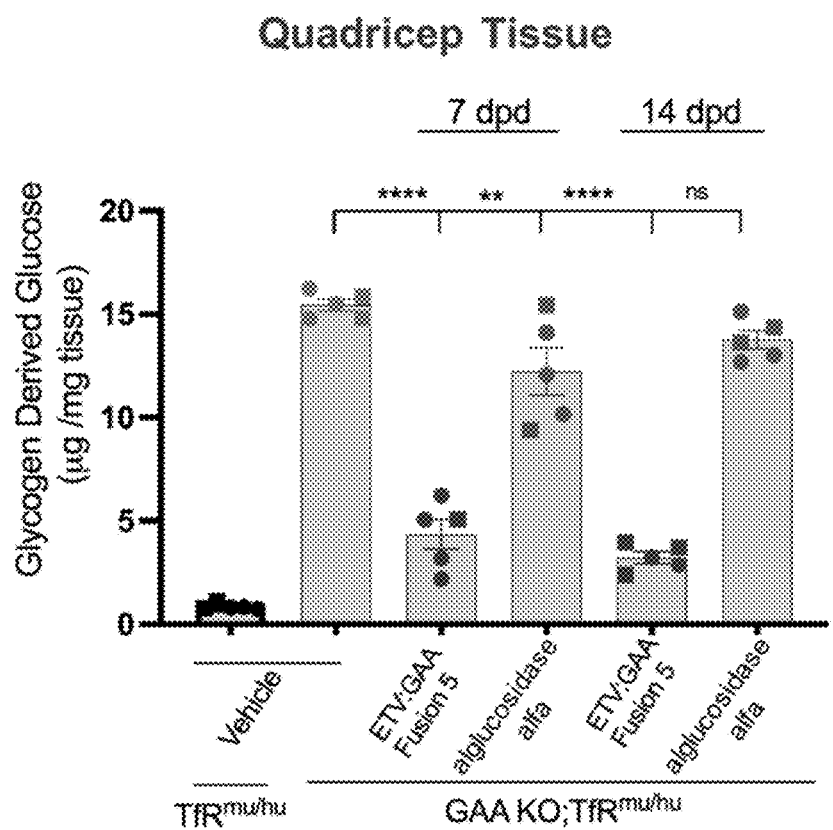
FIGS. 10A-10C. Evaluation of pharmacodynamic response at seven (7) and fourteen (14) days post-single dose in quadricep muscle tissue (FIG. 10A), heart tissue (FIG. 10B), and brain tissue (FIG. 10C) in healthy and disease mouse models of Pompe disease. Mice were dosed with 30 mg/kg of fusion protein or 20 mg/kg alglucosidase alfa. The healthy mouse model is represented by TfR knock in mice ("TfR$^{mu/hu}$") and the disease mouse model is represented by TfR knock in mice in which the gene for GAA has been knocked out ("GAA KO; TfR$^{mu/hu}$") Graphs display mean±SEM and p values: one-way ANOVA Dunnett's multiple comparison test; p≤0.01, *p≤0.001, ****p≤0.0001. Circle symbols=males; square symbols=females; dpd=days post-dose.
Figure 10B:
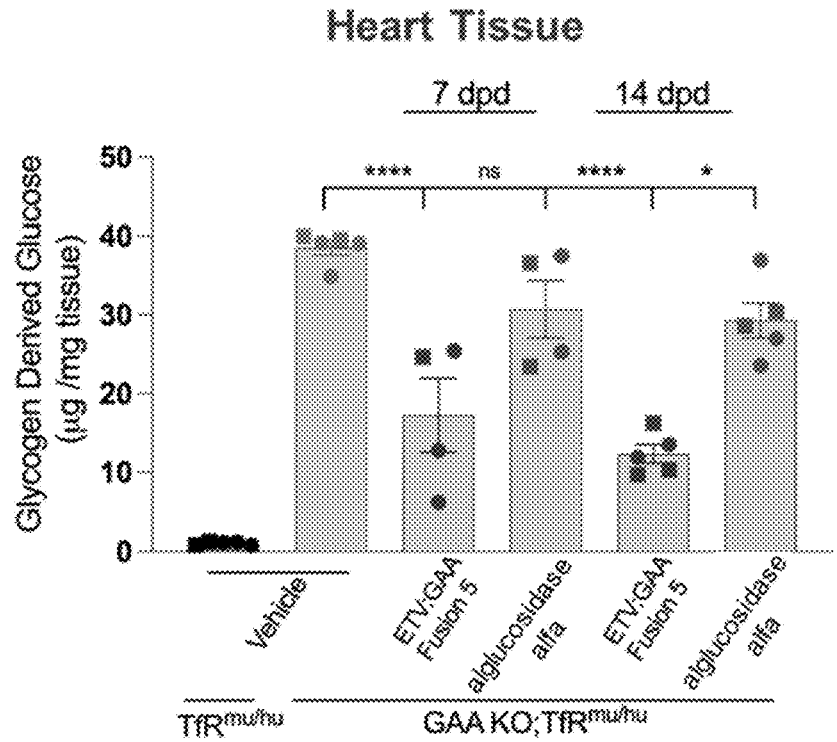
Figure 10C:
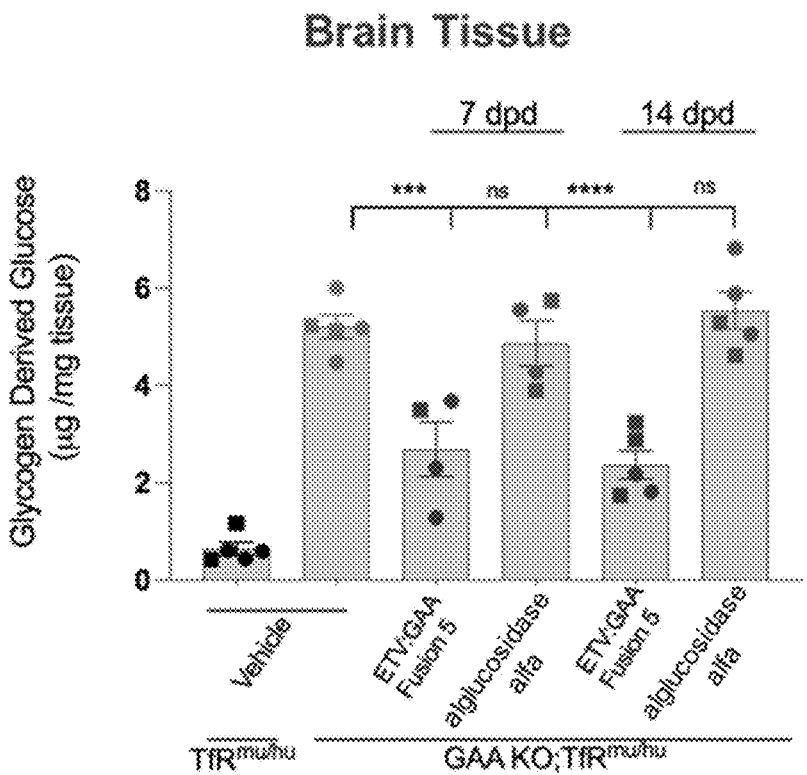

As illustrated in FIGS. 10A-10C and Table 6, at 7 days following a single dose, ETV:GAA Fusion 5 was able to reduce glycogen-derived glucose levels in the quadricep muscle, heart, and brain tissue by about 70%, 55%, and 48%, respectively, relative to vehicle-treated GAA KO; TfR$^{mu/hu}$ KI mice. In comparison, alglucosidase alfa only reduced glycogen-derived glucose levels in quadricep muscle by about 17% at 7 days post-single dose. Furthermore, no significant reduction in glycogen-derived glucose levels in heart or brain tissue was observed for alglucosidase alfa at 7 days post-dose.

As illustrated in FIGS. 10A-10C and Table 7, at 14 days following a single dose, ETV:GAA Fusion 5 was able to reduce glycogen-derived glucose levels in the quadricep muscle, heart, and brain tissue by about 79%, 68%, and 54%, respectively, relative to vehicle-treated GAA KO; TfR$^{mu/hu}$ KI mice. In comparison, alglucosidase alfa only reduced glycogen-derived glucose levels in heart tissue by about 24% at 14 days post-single dose. No significant reduction in glycogen-derived glucose levels in quadricep muscle or brain tissue was observed for alglucosidase alfa at 14 days post-dose.

TABLE 6

Percent reduction in glycogen levels 7 days after single IV dose administration compared to vehicle-treated GAA KO; TfR$^{mu/hu}$ KI mice.

| Treatment | Dose [mg/kg] | Quadricep Tissue Glycogen reduction | Heart Tissue Glycogen reduction | Brain Tissue Glycogen reduction |
|---|---|---|---|---|
| Alglucosidase alfa | 20 | 17% | NS | NS |
| ETV:GAA Fusion 5 | 30 | 70% | 55% | 48% |

NS: Not significant

TABLE 7

Percent reduction in glycogen levels 14 days after single IV dose administration compared to vehicle-treated GAA KO; TfR$^{mu/hu}$ KI mice.

| Treatment | Dose [mg/kg] | Quadricep Tissue Glycogen reduction | Heart Tissue Glycogen reduction | Brain Tissue Glycogen reduction |
|---|---|---|---|---|
| Alglucosidase alfa | 20 | NS | 24% | NS |
| ETV:GAA Fusion 5 | 30 | 79% | 68% | 54% |

NS: Not significant

The data in FIGS. 10A-10C represents approximate mean amounts+/−standard error of the mean. The results demonstrate that ETV:GAA Fusion 5 robustly reduced glycogen accumulation in quadricep muscle, heart, and brain tissue, and this reduction represented an improvement relative to a standard-of-care ERT treatment. In addition, the pharmacodynamic response to treatment with ETV:GAA Fusion 5 was better in all examined tissues at 14-days post dose relative to that at 7-days post dose. The superior improvement in glycogen reduction in quadricep muscle was observed despite very low levels of M6P in ETV:GAA Fusion 5, indicating that the linking of GAA enzyme to a TfR binding component could potentially overcome trafficking limitations imposed by low M6P content.

Experimental Methods

ETV:GAA Fusion 5 was expressed and purified as described in Example 1. Alglucosidase alfa was obtained from a commercial source (Sanofi Genzyme). The mannose-6-phosphate (M6P) content of the proteins was measured as described in Example 2.

Three- to four-month old GAA KO; TfR$^{mu/hu}$ KI mice (Example 4) were administered a single dose of ETV:GAA Fusion 5 (30 mg/kg body weight), alglucosidase alfa (20 mg/kg body weight), or vehicle via intravenous injection (n=5/group). Pharmacokinetic and pharmacodynamic responses were assessed in quadricep muscle, brain, heart, and liver tissues. Approximately same age littermate TfR$^{mu/hu}$ KI mice (non-disease mice) injected i.v. with vehicle were used as controls. All animals were sacrificed 7 days or 14 days post single dose. Muscle, brain, heart, and liver tissue were collected and flash-frozen on dry ice at each termination time point. Serum was also collected in-life at 2 hours and 24 hours post single dose as well as at each termination time point.

For pharmacokinetic analysis, the concentration of GAA enzyme was measured in serum, quadricep muscle, brain, heart, and liver tissue. Total GAA enzyme levels were measured using a sandwich ELISA-based assay at t=2 and 24 hours post-dose for serum PK, and at t=7 and 14 days post-dose for quadricep muscle, brain, heart, and liver PK. Measurement of total GAA enzyme levels were carried out as described in Example 3.

For pharmacodynamic response, muscle, brain, heart, and liver tissue were analyzed for glycogen levels as described in Example 4.

Example 7: A Comparative Study of ETV:GAA Fusion 5 with Avalglucosidase Alfa in a Disease Model of Pompe Disease A C-terminal GAA-Fc fusion protein ("ETV:GAA Fusion 5," Example 6) was generated and compared to a standard-of-care enzyme replacement therapy, avalglucosidase alfa (NEXVIAZYME®), in a mouse model of Pompe disease.

Results

In this study, the pharmacokinetic profile and pharmacodynamic response of ETV:GAA Fusion 5 and avalglucosidase alfa in GAA KO; TfR$^{mu/hu}$ KI mice were compared after a single intravenous (IV) dose. Avalglucosidase alfa was administered to the mice at a dose consistent with a clinically relevant dose for treatment (20 mg/kg), and ETV:GAA Fusion 5 was administered to the mice at an equimolar dose to that of avalglucosidase alfa (30 mg/kg). The M6P content of ETV:Fusion 5 was 0.27 mol/mol, while that of avalglucosidase alfa was 15 mol/mol.

Pharmacokinetic Results.

Figure 11A:
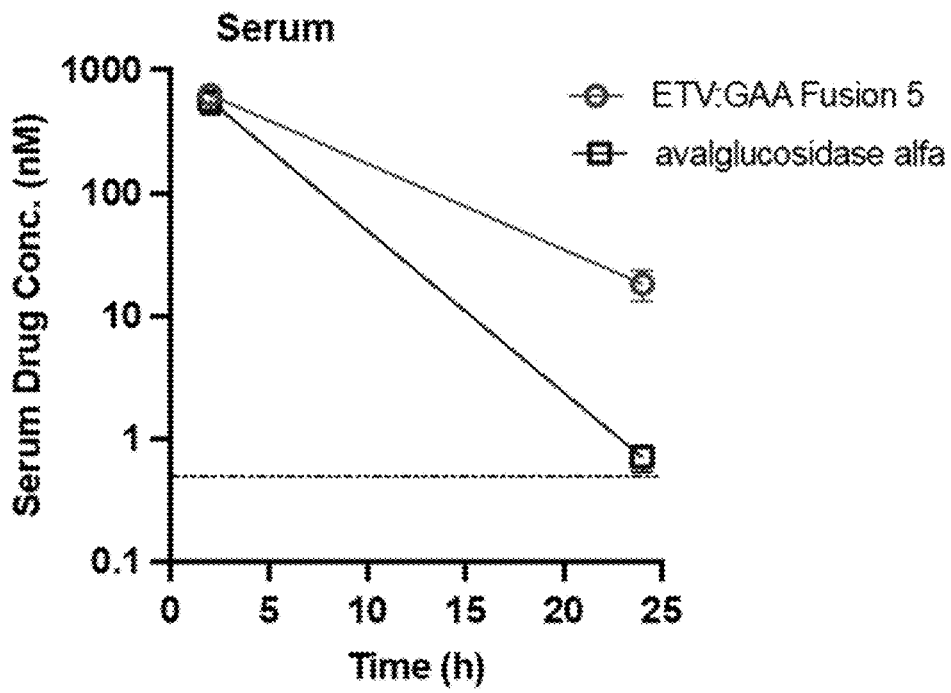
FIGS. 11A-11E. Evaluation of single-dose pharmacokinetics of ETV:GAA Fusion 5 and avalglucosidase alfa (NEXVIAZYME®) in a disease mouse model of Pompe disease (GAA KO; TfR$^{mu/hu}$ KI mice) in serum (FIG. 11A), quadricep muscle tissue (FIG. 11B), heart tissue (FIG. 11C), brain tissue (FIG. 11D), and liver tissue (FIG. 11E). Mice were dosed with 30 mg/kg of fusion protein or 20 mg/kg avalglucosidase alfa. N=5 per group. The lower limit of quantitation (LLOQ) for serum is included in FIG. 11A as a horizontal dotted line.
Figure 11B:
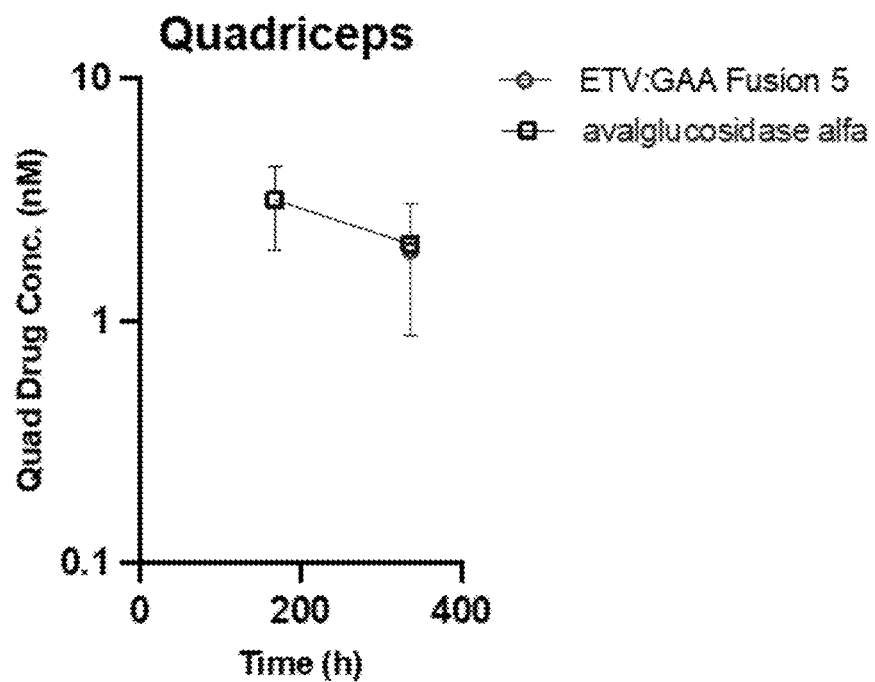
Figure 11C:
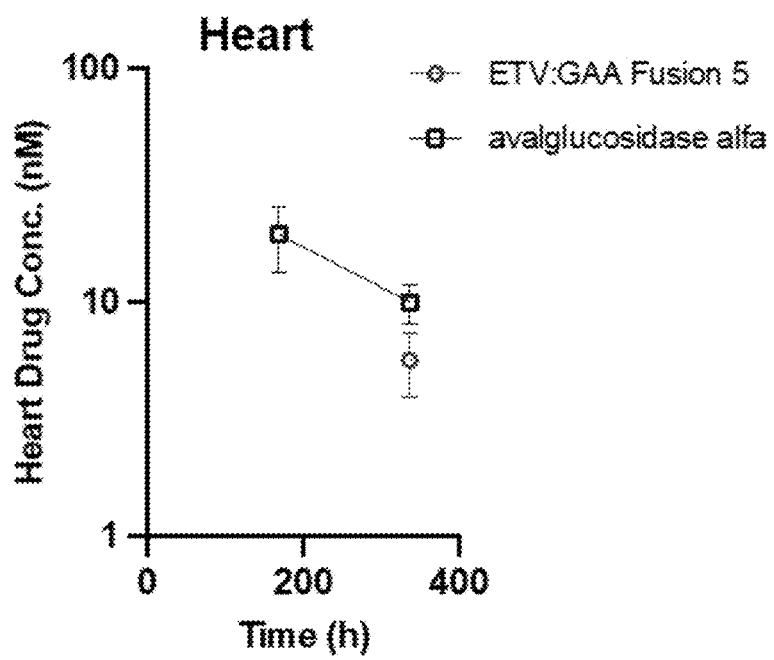
Figure 11D:
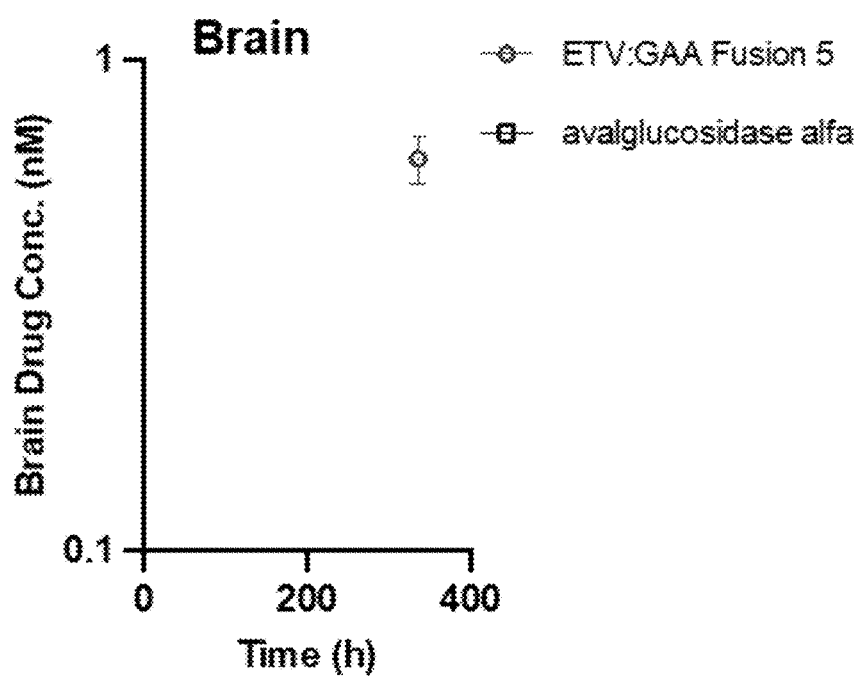
Figure 11E:
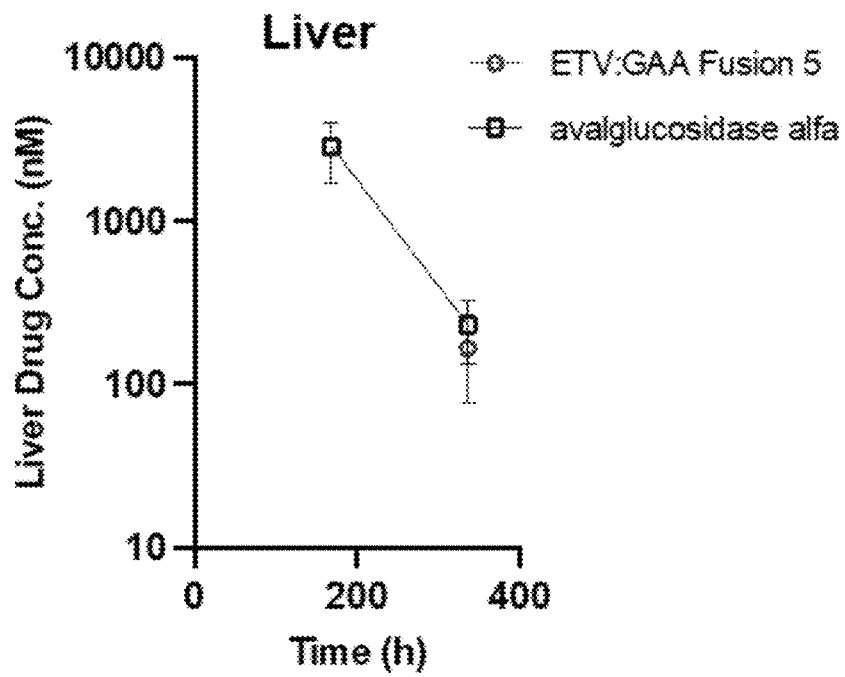

Pharmacokinetic profiles for the tested tissues are provided in FIGS. 11A-11E. As illustrated in FIG. 11A, ETV:GAA Fusion 5 remained stable in serum for up to 24 hours post-dose, while avalglucosidase alfa showed faster clearance relative to ETV:GAA Fusion 5. At 24 hours post-dose, the serum concentration of ETV:GAA Fusion 5 was about 100-fold greater than that of avalglucosidase alfa. In quadricep muscle and heart tissue (FIGS. 11B, 11C), concentrations of ETV:GAA Fusion 5 and avalglucosidase alfa were comparable at 14-days post single dose. In the brain, ETV:GAA Fusion 5 concentrations remained detectable at 14-days post single dose, while avalglucosidase alfa measurements were below the limits of detection at both 7- and 14-days post-dose (FIG. 11D). In liver tissue, concentrations of avalglucosidase alfa were slightly greater than that of ETV:GAA Fusion 5 at 14-days post dose (FIG. 11E). Collectively, the results illustrate that the ETV:GAA Fusion 5 achieved improved tissue exposure relative a standard-of-care ERT enzyme (avalglucosidase alfa) in serum and brain tissue and comparable tissue exposure relative to the standard-of-care ERT enzyme in quadricep muscle and heart tissues.

Pharmacodynamic Results

Figure 12A:
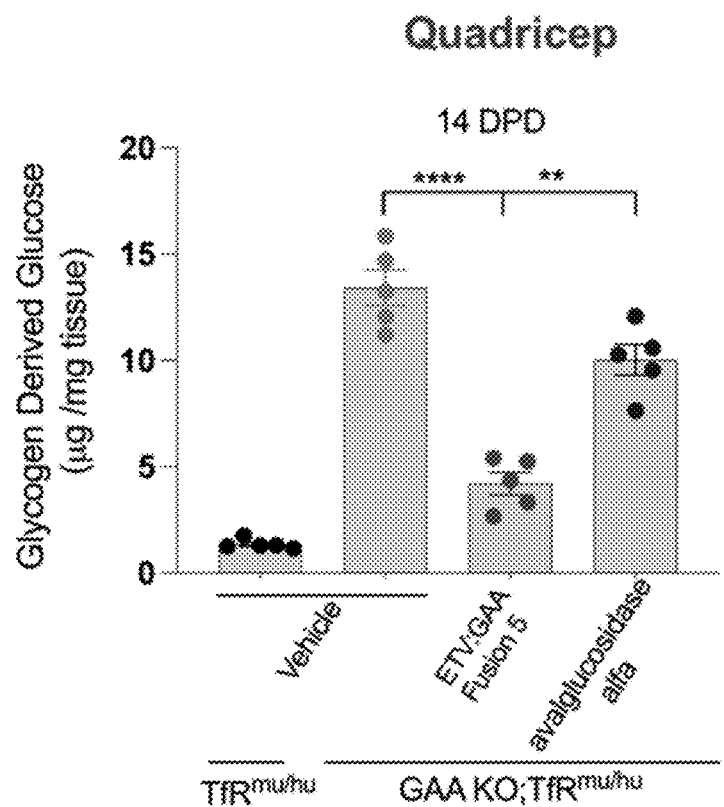
FIGS. 12A-12D. Evaluation of pharmacodynamic response at 14 days post-single dose in quadricep muscle tissue (FIG. 12A), brain tissue (FIG. 12B), heart tissue (FIG. 12C), and liver tissue (FIG. 12D) in healthy and disease mouse models of Pompe disease. Mice were dosed with 30 mg/kg of fusion protein or 20 mg/kg avalglucosidase alfa (NEXVIAZYME®). The healthy mouse model is represented by TfR knock in mice ("TfR$^{mu/hu}$") and the disease mouse model is represented by TfR knock in mice in which the gene for GAA has been knocked out ("GAA KO; TfR$^{mu/hu}$"). Graphs display mean±SEM and p values: one-way ANOVA Dunnett's multiple comparison test; p≤0.01, **p≤0.0001; DPD=days post-dose.
Figure 12B:
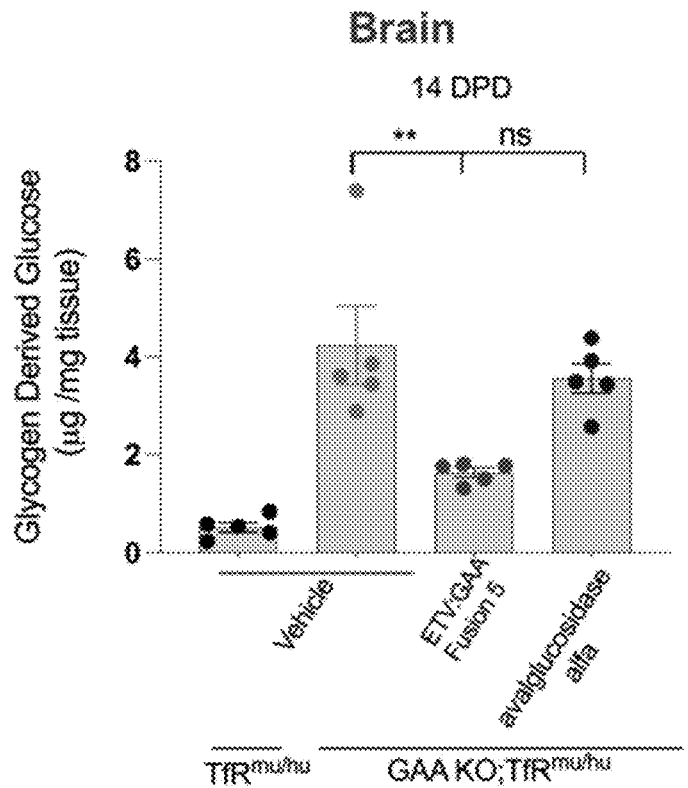
Figure 12C:
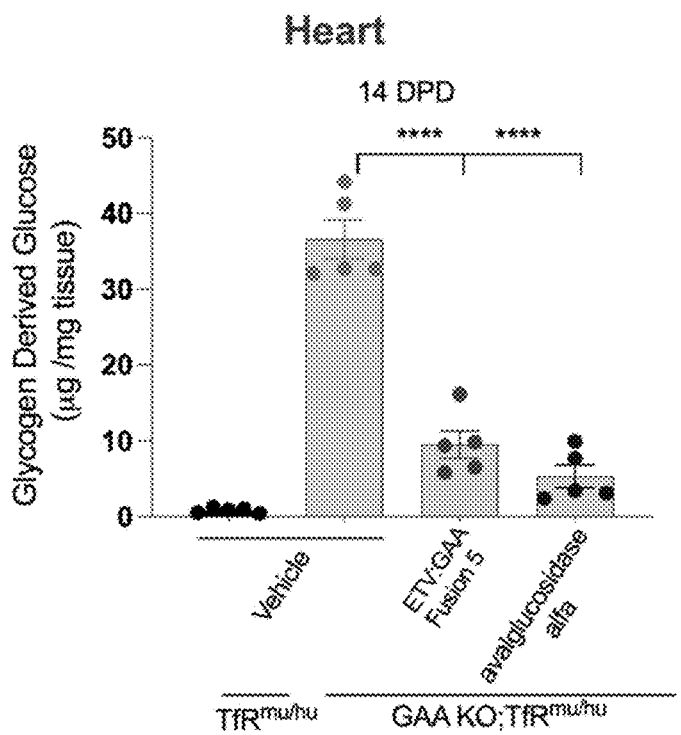
Figure 12D:
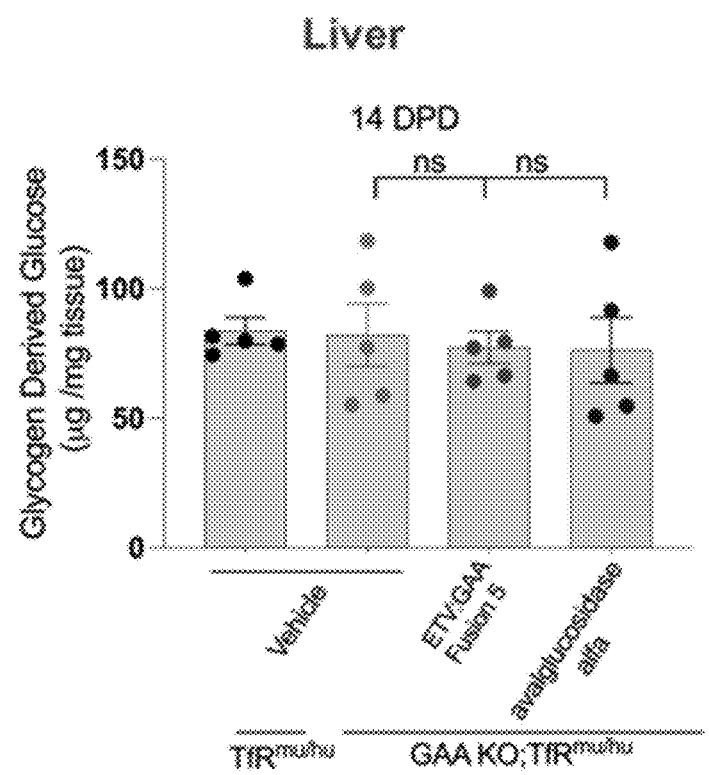

As illustrated in FIGS. 12A-12C and Table 8, at 14 days following a single dose, ETV:GAA Fusion 5 was able to reduce glycogen-derived glucose levels in the quadricep muscle and brain tissue by about 69% and 62%, respectively, relative to vehicle-treated GAA KO; TfR$^{mu/hu}$ KI mice. In comparison, avalglucosidase alfa only reduced glycogen-derived glucose levels in quadricep muscle tissue by about 25% at 14 days post-single dose, and no significant reduction in glycogen-derived glucose levels in brain tissue was observed. In heart tissue, ETV:GAA Fusion 5 and avalglucosidase alfa were both able to reduce glycogen-derived glucose levels at 14 days post-single dose (74% and 85% reduction, respectively).

TABLE 8

Percent reduction in glycogen levels 14 days after single IV dose administration compared to vehicle-treated GAA KO; TfR$^{mu/hu}$ KI mice.

| Treatment | Dose [mg/kg] | Quadricep Tissue Glycogen reduction | Heart Tissue Glycogen reduction | Brain Tissue Glycogen reduction |
|---|---|---|---|---|
| Avalglucosidase alfa | 20 | 25% | 85% | NS |
| ETV:GAA Fusion 5 | 30 | 69% | 74% | 62% |

NS: Not significant

The data in FIGS. 12A-12C represents approximate mean amounts+/−standard error of the mean. The results demonstrate that at 14 days post-dose, ETV:GAA Fusion 5 robustly reduced glycogen accumulation in quadricep muscle and brain tissue, and this reduction represented an improvement relative to a standard-of-care ERT treatment. In addition, the pharmacodynamic response to treatment with ETV:GAA Fusion 5 and avalglucosidase alfa was comparable in heart tissue. The superior improvement in glycogen reduction in quadricep muscle was observed despite very low levels of M6P in ETV:GAA Fusion 5 relative to avalglucosidase alfa, indicating that the linking of GAA enzyme to a TfR binding component could potentially overcome trafficking limitations imposed by low M6P content.

Experimental Methods

ETV:GAA Fusion 5 was expressed from a stable pool cell line by fed-batch production. Generation of the stable pool cell line and recombinant protein expression was carried out as described in Example 5. Avalglucosidase alfa was obtained from a commercial source (Sanofi Genzyme).

Two- to three-month old GAA KO; TfR$^{mu/hu}$ KI mice (Example 4) were administered a single dose of ETV:GAA Fusion 5 (30 mg/kg body weight), avalglucosidase alfa (20 mg/kg body weight), or vehicle via intravenous injection (n=5/group). Pharmacokinetic and pharmacodynamic responses were assessed in quadricep muscle, brain, heart, and liver tissues. Approximately same age littermate TfR$^{mu/hu}$ KI mice (non-disease mice) injected i.v. with vehicle were used as controls. All animals were sacrificed 14 days post single dose. Muscle, brain, heart, and liver tissue were collected and flash-frozen on dry ice at each termination time point. Serum was collected in-life at 2 hours and 24 hours post single dose as well as at the termination time point for mice treated with ETV:GAA Fusion 5 or vehicle. Serum was collected in-life at 2 hours, 24 hours, and 7 days post single dose as well as at the termination time point for mice treated with avalglucosidase alfa.

For pharmacokinetic analysis, the concentration of GAA enzyme was measured in serum, quadricep muscle, brain, heart, and liver tissue. Total GAA enzyme levels were measured using a sandwich ELISA-based assay at t=2 and 24 hours post-dose for serum PK, and at t=7 and/or 14 days post-dose for quadricep muscle, brain, heart, and liver PK. Measurement of total GAA enzyme levels were carried out as described in Example 3.

For pharmacodynamic response, muscle, brain, heart, and liver tissue were analyzed for glycogen levels as described in Example 4.

| | Informal Sequence Listing | |
|---|---|---|
| SEQ ID NO: | Sequence | Description |
| 1 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQ KSLSLSPGK | Wild-type human Fc sequence positions 231-447 EU index numbering |
| 2 | APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQ KSLSLSPG | Wild-type human Fc sequence positions 231-446 EU index numbering |
| 3 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAK | CH2 domain sequence positions 231-340 EU index numbering |
| 4 | GQPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLSLS PGK | CH3 domain sequence Positions 341-447 EU index numbering |
| 5 | EPKSCDKTHTCPPCP | Human IgG1 hinge amino acid sequence |
| 6 | DKTHTCPPCP | Portion of human IgG1 hinge sequence |
| 7 | MMDQARSAFSNLFGGEPLSYTRFSLARQVDGDNSHVEMKLAVDEEENADNNT KANVTKPKRCSGSICYGTIAVIVFFLIGFMIGYLGYCKGVEPKTECERLAGT ESPVREEPGEDFPAARRLYWDDLKRKLSEKLDSTDFTGTIKLLNENSYVPRE AGSQKDENLALYVENQFREFKLSKVWRDQHFVKIQVKDSAQNSVIIVDKNGR LVYLVENPGGYVAYSKAATVTGKLVHANFGTKKDFEDLYTPVNGSIVIVRAG KITFAEKVANAESLNAIGVLIYMDQTKFPIVNAELSFFGHAHLGTGDPYTPG FPSFNHTQFPPSRSSGLPNIPVQTISRAAAEKLFGNMEGDCPSDWKTDSTCR MVTSESKNVKLTVSNVLKEIKILNIFGVIKGFVEPDHYVVVGAQRDAWGPGA AKSGVGTALLLKLAQMFSDMVLKDGFQPSRSIIFASWSAGDFGSVGATEWLE GYLSSLHLKAFTYINLDKAVLGTSNFKVSASPLLYTLIEKTMQNVKHPVTGQ FLYQDSNWASKVEKLTLDNAAFPFLAYSGIPAVSFCFCEDTDYPYLGTTMDT YKELIERIPELNKVARAAAEVAGQFVIKLTHDVELNLDYERYNSQLLSFVRD LNQYRADIKEMGLSLQWLYSARGDFFRATSRLTTDFGNAEKTDRFVMKKLND RVMRVEYHFLSPYVSPKESPFRHVFWGSGSHTLPALLENLKLRKQNNGAFNE TLFRNQLALATWTIQGAANALSGDVWDIDNEF | Human transferrin receptor protein 1 (TFR1) |
| 8 | NSVIIVDKNGRLVYLVENPGGYVAYSKAATVTGKLVHANFGTKKDFEDLYTP VNGSIVIVRAGKITFAEKVANAESLNAIGVLIYMDQTKFPIVNAELSFFGHA HLGTGDPYTPGFPSFNHTQFPPSRSSGLPNIPVQTISRAAAEKLEGNMEGDC PSDWKTDSTCRMVTSESKNVKLTVS | Human TfR apical domain |
| 9 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLSCAVKGFYPSDIAVEWESNGQ PENNYKTTPPVLDSDGSFFLVSKLTVDKSRWQQGNVFSCSVMHEALHNHYTQ KSLSLSPGK | Fc sequence with hole mutations |
| 10 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLSCAVKGFYPSDIAVEWESNGQ PENNYKTTPPVLDSDGSFFLVSKLTVDKSRWQQGNVFSCSVMHEALHNHYTQ KSLSLSPG | Fc sequence with hole mutations |
| 11 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLSCAVKGFYPSDIAVEWESNGQ PENNYKTTPPVLDSDGSFFLVSKLTVDKSRWQQGNVFSCSVMHEALHNHYTQ KSLSLSPGK | Fc sequence with hole and LALA mutations |

| SEQ ID NO: | Sequence | Description |
|---|---|---|
| 12 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLSCAVKGFYPSDIAVEWESNGQ PENNYKTTPPVLDSDGSFFLVSKLTVDKSRWQQGNVFSCSVMHEALHNHYTQ KSLSLSPG | Fc sequence with hole and LALA mutations |
| 13 | APEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALGAPIEK TISKAKGQPREPQVYTLPPSRDELTKNQVSLSCAVKGFYPSDIAVEWESNGQ PENNYKTTPPVLDSDGSFFLVSKLTVDKSRWQQGNVFSCSVMHEALHNHYTQ KSLSLSPGK | Fc sequence with hole and LALAPG mutations |
| 14 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALGAPIEK TISKAKGQPREPQVYTLPPSRDELTKNQVSLSCAVKGFYPSDIAVEWESNGQ PENNYKTTPPVLDSDGSFFLVSKLTVDKSRWQQGNVFSCSVMHEALHNHYTQ KSLSLSPG | Fc sequence with hole and LALAPG mutations |
| 15 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALSAPIEK TISKAKGQPREPQVYTLPPSRDELTKNQVSLSCAVKGFYPSDIAVEWESNGQ PENNYKTTPPVLDSDGSFFLVSKLTVDKSRWQQGNVFSCSVMHEALHNHYTQ KSLSLSPGK | Fc sequence with hole and LALAPS mutations |
| 16 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALSAPIEK TISKAKGQPREPQVYTLPPSRDELTKNQVSLSCAVKGFYPSDIAVEWESNGQ PENNYKTTPPVLDSDGSFFLVSKLTVDKSRWQQGNVFSCSVMHEALHNHYTQ KSLSLSPG | Fc sequence with hole and LALAPS mutations |
| 17 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLWCLVKGFYPSDIAVEWESNGQ PENNYKTTPPVLDSDGSFFLYSKLTVDKSRWQQGNVFSCSVMHEALHNHYTQ KSLSLSPGK | Fc sequence with knob mutation |
| 18 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLWCLVKGFYPSDIAVEWESNGQ PENNYKTTPPVLDSDGSFFLYSKLTVDKSRWQQGNVFSCSVMHEALHNHYTQ KSLSLSPG | Fc sequence with knob mutation |
| 19 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLWCLVKGFYPSDIAVEWESNGQ PENNYKTTPPVLDSDGSFFLYSKLTVDKSRWQQGNVFSCSVMHEALHNHYTQ KSLSLSPGK | Fc sequence with knob and LALA mutations |
| 20 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLWCLVKGFYPSDIAVEWESNGQ PENNYKTTPPVLDSDGSFFLYSKLTVDKSRWQQGNVFSCSVMHEALHNHYTQ KSLSLSPG | Fc sequence with knob and LALA mutations |
| 21 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPAPIEKTISKAKGQPREPQVYTLPPSRDELTKNQVSLSCAVKGFYPSD IAVEWESNGQPENNYKTTPPVLDSDGSFFLVSKLTVDKSRWQQGNVFSCSVM HEALHNHYTQKSLSLSPGK | Fc sequence with hole and LALA mutations and portion of human IgG1 hinge sequence |
| 22 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPAPIEKTISKAKGQPREPQVYTLPPSRDELTKNQVSLSCAVKGFYPSD IAVEWESNGQPENNYKTTPPVLDSDGSFFLVSKLTVDKSRWQQGNVFSCSVM HEALHNHYTQKSLSLSPG | Fc sequence with hole and LALA mutations and portion of human IgG1 hinge sequence |

-continued

| | Informal Sequence Listing | |
|---|---|---|
| SEQ ID NO: | Sequence | Description |
| 23 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALSAPIEKTISKAKGQPREPQVYTLPPSRDELTKNQVSLSCAVKGFYPSD IAVEWESNGQPENNYKTTPPVLDSDGSFFLVSKLTVDKSRWQQGNVFSCSVM HEALHNHYTQKSLSLSPGK | Fc sequence with hole and LALAPS mutations and portion of human IgG1 hinge sequence |
| 24 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALSAPIEKTISKAKGQPREPQVYTLPPSRDELTKNQVSLSCAVKGFYPSD IAVEWESNGQPENNYKTTPPVLDSDGSFFLVSKLTVDKSRWQQGNVFSCSVM HEALHNHYTQKSLSLSPG | Fc sequence with hole and LALAPS mutations and portion of human IgG1 hinge sequence |
| 25 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPAPIEKTISKAKGQPREPQVYTLPPSRDELTKNQVSLWCLVKGFYPSD IAVEWESNGQPENNYKTTPPVLDSDGSFFLYSKLTVDKSRWQQGNVFSCSVM HEALHNHYTQKSLSLSPGK | Fc sequence with knob and LALA mutations and portion of human IgG1 hinge sequence |
| 26 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPAPIEKTISKAKGQPREPQVYTLPPSRDELTKNQVSLWCLVKGFYPSD IAVEWESNGQPENNYKTTPPVLDSDGSFFLYSKLTVDKSRWQQGNVFSCSVM HEALHNHYTQKSLSLSPG | Fc sequence with knob and LALA mutations and portion of human IgG1 hinge sequence |
| 27 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESYGT EWANYKTTPPVLDSDGSFFLYSKLTVTKEEWQQGFVFSCSVMHEALHNHYTQ KSLSLSPGK | Clone CH3C.35.23.2 |
| 28 | APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESYGT EWANYKTTPPVLDSDGSFFLYSKLTVTKEEWQQGFVFSCSVMHEALHNHYTQ KSLSLSPG | Clone CH3C.35.23.2 |
| 29 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLWCLVKGFYPSDIAVEWESYGT EWANYKTTPPVLDSDGSFFLYSKLTVTKEEWQQGFVFSCSVMHEALHNHYTQ KSLSLSPGK | Clone CH3C.35.23.2 with knob mutation |
| 30 | APELLGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLWCLVKGFYPSDIAVEWESYGT EWANYKTTPPVLDSDGSFFLYSKLTVTKEEWQQGFVFSCSVMHEALHNHYTQ KSLSLSPG | Clone CH3C.35.23.2 with knob mutation |
| 31 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLWCLVKGFYPSDIAVEWESYGT EWANYKTTPPVLDSDGSFFLYSKLTVTKEEWQQGFVFSCSVMHEALHNHYTQ KSLSLSPGK | Clone CH3C.35.23.2 with knob and LALA mutations |
| 32 | APEAAGGPSVFLFPPKPKDTLMISRTPEVTCVVVDVSHEDPEVKENWYVDGV EVHNAKTKPREEQYNSTYRVVSVLTVLHQDWLNGKEYKCKVSNKALPAPIEK TISKAKGQPREPQVYTLPPSRDELTKNQVSLWCLVKGFYPSDIAVEWESYGT EWANYKTTPPVLDSDGSFFLYSKLTVTKEEWQQGFVFSCSVMHEALHNHYTQ KSLSLSPG | Clone CH3C.35.23.2 with knob and LALA mutations |
| 33 | APEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALGAPIEK TISKAKGQPREPQVYTLPPSRDELTKNQVSLWCLVKGFYPSDIAVEWESYGT EWANYKTTPPVLDSDGSFFLYSKLTVTKEEWQQGFVFSCSVMHEALHNHYTQ KSLSLSPGK | Clone CH3C.35.23.2 with knob and LALAPG mutations |

| SEQ ID NO: | Sequence | Description |
|---|---|---|
| 34 | APEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALGAPIEK TISKAKGQPREPQVYTLPPSRDELTKNQVSLWCLVKGFYPSDIAVEWESYGT EWANYKTTPPVLDSDGSFFLYSKLTVTKEEWQQGFVFSCSVMHEALHNHYTQ KSLSLSPG | Clone CH3C.35.23.2 with knob and LALAPG mutations |
| 35 | APEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALSAPIEK TISKAKGQPREPQVYTLPPSRDELTKNQVSLWCLVKGFYPSDIAVEWESYGT EWANYKTTPPVLDSDGSFFLYSKLTVTKEEWQQGFVFSCSVMHEALHNHYTQ KSLSLSPGK | Clone CH3C.35.23.2 with knob and LALAPS mutations |
| 36 | APEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALSAPIEK TISKAKGQPREPQVYTLPPSRDELTKNQVSLWCLVKGFYPSDIAVEWESYGT EWANYKTTPPVLDSDGSFFLYSKLTVTKEEWQQGFVFSCSVMHEALHNHYTQ KSLSLSPG | Clone CH3C.35.23.2 with knob and LALAPS mutations |
| 37 | APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEK TISKAKGQPREPQVYTLPPSRDELTKNQVSLSCAVKGFYPSDIAVEWESYGT EWANYKTTPPVLDSDGSFFLYSKLTVTKEEWQQGFVFSCSVMHEALHNHYTQ KSLSLSPGK | Clone CH3C.35.23.2 with hole mutations |
| 38 | APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEK TISKAKGQPREPQVYTLPPSRDELTKNQVSLSCAVKGFYPSDIAVEWESYGT EWANYKTTPPVLDSDGSFFLYSKLTVTKEEWQQGFVFSCSVMHEALHNHYTQ KSLSLSPG | Clone CH3C.35.23.2 with hole mutations |
| 39 | APEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEK TISKAKGQPREPQVYTLPPSRDELTKNQVSLSCAVKGFYPSDIAVEWESYGT EWANYKTTPPVLDSDGSFFLYSKLTVTKEEWQQGFVFSCSVMHEALHNHYTQ KSLSLSPGK | Clone CH3C.35.23.2 with hole and LALA mutations |
| 40 | APEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEK TISKAKGQPREPQVYTLPPSRDELTKNQVSLSCAVKGFYPSDIAVEWESYGT EWANYKTTPPVLDSDGSFFLYSKLTVTKEEWQQGFVFSCSVMHEALHNHYTQ KSLSLSPG | Clone CH3C.35.23.2 with hole and LALA mutations |
| 41 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPAPIEKTISKAKGQPREPQVYTLPPSRDELTKNQVSLWCLVKGFYPSD IAVEWESYGTEWANYKTTPPVLDSDGSFFLYSKLTVTKEEWQQGFVFSCSVM HEALHNHYTQKSLSLSPGK | Clone CH3C.35.23.2 with knob and LALA mutations and portion of human IgG1 hinge sequence |
| 42 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALPAPIEKTISKAKGQPREPQVYTLPPSRDELTKNQVSLWCLVKGFYPSD IAVEWESYGTEWANYKTTPPVLDSDGSFFLYSKLTVTKEEWQQGFVFSCSVM HEALHNHYTQKSLSLSPG | Clone CH3C.35.23.2 with knob and LALA mutations and portion of human IgG1 hinge sequence |
| 43 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALSAPIEKTISKAKGQPREPQVYTLPPSRDELTKNQVSLWCLVKGFYPSD IAVEWESYGTEWANYKTTPPVLDSDGSFFLYSKLTVTKEEWQQGFVFSCSVM HEALHNHYTQKSLSLSPGK | Clone CH3C.35.23.2 with knob and LALAPS mutations and portion of human IgG1 hinge sequence |

| SEQ ID NO: | Sequence | Description |
|---|---|---|
| 44 | DKTHTCPPCPAPEAAGGPSVFLFPPKPKDTLMISRTPEVTCVVVDVSHEDPE VKFNWYVDGVEVHNAKTKPREEQYNSTYRVVSVLTVLHQDWLNGKEYKCKVS NKALSAPIEKTISKAKGQPREPQVYTLPPSRDELTKNQVSLWCLVKGFYPSD IAVEWESYGTEWANYKTTPPVLDSDGSFFLYSKLTVTKEEWQQGFVFSCSVM HEALHNHYTQKSLSLSPG | Clone CH3C.35.23.2 with knob and LALAPS mutations and portion of human IgG1 hinge sequence |
| 45 | MGVRHPPCSHRLLAVCALVSLATAALLGHILLHDFLLVPRELSGSSPVL EETHPAHQQGASRPGPRDAQAHPGRPRAVPTQCDVPPNSREDCAPDKAI TQEQCEARGCCYIPAKQGLQGAQMGQPWCFFPPSYPSYKLENLSSSEMG YTATLTRTTPTFFPKDILTLRLDVMMETENRLHFTIKDPANRRYEVPLE TPHVHSRAPSPLYSVEFSEEPFGVIVRRQLDGRVLLNTTVAPLFFADQF LQLSTSLPSQYITGLAEHLSPLMLSTSWTRITLWNRDLAPTPGANLYGS HPFYLALEDGGSAHGVFLLNSNAMDVVLQPSPALSWRSTGGILDVYIFL GPEPKSVVQQYLDVVGYPFMPPYWGLGFHLCRWGYSSTAITRQVVENMT RAHFPLDVQWNDLDYMDSRRDFTENKDGFRDFPAMVQELHQGGRRYMMI VDPAISSSGPAGSYRPYDEGLRRGVFITNETGQPLIGKVWPGSTAFPDF TNPTALAWWEDMVAEFHDQVPFDGMWIDMNEPSNFIRGSEDGCPNNELE NPPYVPGVVGGTLQAATICASSHQFLSTHYNLHNLYGLTEAIASHRALV KARGTRPFVISRSTFAGHGRYAGHWTGDVWSSWEQLASSVPEILQFNLL GVPLVGADVCGFLGNTSEELCVRWTQLGAFYPFMRNHNSLLSLPQEPYS FSEPAQQAMRKALTLRYALLPHLYTLFHQAHVAGETVARPLFLEFPKDS STWTVDHQLLWGEALLITPVLQAGKAEVTGYFPLGTWYDLQTVPVEALG SLPPPPAAPREPAIHSEGQWVTLPAPLDTINVHLRAGYIIPLQGPGLTT TESRQQPMALAVALTKGGEARGELFWDDGESLEVLERGAYTQVIFLARN NTIVNELVRVTSEGAGLQLQKVTVLGVATAPQQVLSNGVPVSNFTYSPD TKVLDICVSLLMGEQFLVSWC | Full-length human acid alpha-glucosidase (GAA) polypeptide sequence |
| 46 | GHILLHDFLLVPRELSGSSPVLEETHPAHQQGASRPGPRDAQAHPGRPRAVP TQCDVPPNSREDCAPDKAITQEQCEARGCCYIPAKQGLQGAQMGQPWCFFPP SYPSYKLENLSSSEMGYTATLTRTTPTFFPKDILTLRLDVMMETENRLHFTI KDPANRRYEVPLETPHVHSRAPSPLYSVEFSEEPFGVIVRRQLDGRVLLNTT VAPLFFADQFLQLSTSLPSQYITGLAEHLSPLMLSTSWTRITLWNRDLAPTP GANLYGSHPFYLALEDGGSAHGVFLLNSNAMDVVLQPSPALSWRSTGGILDV YIFLGPEPKSVVQQYLDVVGYPFMPPYWGLGFHLCRWGYSSTAITRQVVENM TRAHFPLDVQWNDLDYMDSRRDFTENKDGERDFPAMVQELHQGGRRYMMIVD PAISSSGPAGSYRPYDEGLRRGVFITNETGQPLIGKVWPGSTAFPDFTNPTA LAWWEDMVAEFHDQVPFDGMWIDMNEPSNFIRGSEDGCPNNELENPPYVPGV VGGTLQAATICASSHQFLSTHYNLHNLYGLTEAIASHRALVKARGTRPFVIS RSTFAGHGRYAGHWTGDVWSSWEQLASSVPEILQFNLLGVPLVGADVCGFLG NTSEELCVRWTQLGAFYPFMRNHNSLLSLPQEPYSFSEPAQQAMRKALTLRY ALLPHLYTLFHQAHVAGETVARPLFLEFPKDSSTWTVDHQLLWGEALLITPV LQAGKAEVTGYFPLGTWYDLQTVPVEALGSLPPPPAAPREPAIHSEGQWVTL PAPLDTINVHLRAGYIIPLQGPGLTTTESRQQPMALAVALTKGGEARGELFW DDGESLEVLERGAYTQVIFLARNNTIVNELVRVTSEGAGLQLQKVTVLGVAT APQQVLSNGVPVSNFTYSPDTKVLDICVSLLMGEQFLVSWC | Mature human acid alpha-glucosidase (GAA) polypeptide |
| 47 | AHPGRPRAVPTQCDVPPNSREDCAPDKAITQEQCEARGCCYIPAKQGLQGAQ MGQPWCFFPPSYPSYKLENLSSSEMGYTATLTRTTPTFFPKDILTLRLDVMM ETENRLHFTIKDPANRRYEVPLETPHVHSRAPSPLYSVEFSEEPFGVIVRRQ LDGRVLLNTTVAPLFFADQFLQLSTSLPSQYITGLAEHLSPLMLSTSWTRIT LWNRDLAPTPGANLYGSHPFYLALEDGGSAHGVFLLNSNAMDVVLQPSPALS WRSTGGILDVYIFLGPEPKSVVQQYLDVVGYPFMPPYWGLGFHLCRWGYSST AITRQVVENMTRAHFPLDVQWNDLDYMDSRRDFTENKDGFRDFPAMVQELHQ GGRRYMMIVDPAISSSGPAGSYRPYDEGLRRGVFITNETGQPLIGKVWPGST AFPDFTNPTALAWWEDMVAEFHDQVPFDGMWIDMNEPSNFIRGSEDGCPNNE LENPPYVPGVVGGTLQAATICASSHQFLSTHYNLHNLYGLTEAIASHRALVK ARGTRPFVISRSTFAGHGRYAGHWTGDVWSSWEQLASSVPEILQFNLLGVPL VGADVCGFLGNTSEELCVRWTQLGAFYPFMRNHNSLLSLPQEPYSFSEPAQQ AMRKALTLRYALLPHLYTLFHQAHVAGETVARPLFLEFPKDSSTWTVDHQLL WGEALLITPVLQAGKAEVTGYFPLGTWYDLQTVPVEALGSLPPPPAAPREPA IHSEGQWVTLPAPLDTINVHLRAGYIIPLQGPGLTTTESRQQPMALAVALTK GGEARGELFWDDGESLEVLERGAYTQVIFLARNNTIVNELVRVTSEGAGLQL QKVTVLGVATAPQQVLSNGVPVSNFTYSPDTKVLDICVSLLMGEQFLVSWC | Embodiment of a truncated human acid alpha-glucosidase (GAA) polypeptide sequence |

-continued

Informal Sequence Listing

| SEQ ID NO: | Sequence | Description |
|---|---|---|
| 48 | GHILLHDFLLVPRELSGSSPVLEETHPAHQQGASRPGPRDAQAHPGRPRAVP TQCDVPPNSREDCAPDKAITQEQCEARGCCYIPAKQGLQGAQMGQPWCFFPP SYPSYKLENLSSSEMGYTATLTRTTPTFFPKDILTLRLDVMMETENRLHFTI KDPANRRYEVPLETPHVHSRAPSPLYSVEFSEEPFGVIVRRQLDGRVLLNTT VAPLFFADQFLQLSTSLPSQYITGLAEHLSPLMLSTSWTRITLWNRDLAPTP GANLYGSHPFYLALEDGGSAHGVFLLNSNAMDVVLQPSPALSWRSTGGILDV YIFLGPEPKSVVQQYLDVVGYPFMPPYWGLGFHLCRWGYSSTAITRQVVENM TRAHFPLDVQWNDLDYMDSRRDFTENKDGFRDFPAMVQELHQGGRRYMMIVD PAISSSGPAGSYRPYDEGLRRGVFITNETGQPLIGKVWPGSTAFPDFTNPTA LAWWEDMVAEFHDQVPFDGMWIDMNEPSNFIRGSEDGCPNNELENPPYVPGV VGGTLQAATICASSHQFLSTHYNLHNLYGLTEAIASHRALVKARGTRPFVIS RSTFAGHGRYAGHWTGDVWSSWEQLASSVPEILQFNLLGVPLVGADVCGFLG NTSEELCVRWTQLGAFYPFMRNHNSLLSLPQEPYSFSEPAQQAMRKALTLRY ALLPHLYTLFHQAHVAGETVARPLFLEFPKDSSTWTVDHQLLWGEALLITPV LQAGKAEVTGYFPLGTWYDLQTVPVEALGSLPPPPAAPREPAIHSEGQWVTL PAPLDTINVHLRAGYIIPLQGPGLTTTESRQQPMALAVALTKGGEARGELFW DDGESLEVLERGAYTQVIFLARNNTIVNELVRVTSEGAGLQLQKVTVLGVAT APQQVLSNGVPVSNFTYSPDTKVLDICVSLLMGEQFLVSWCGGGGSDKTHTC PPCPAPEAAGGPSVFLFPPKPKDTLMISRTPEVTCVVVDVSHEDPEVKENWY VDGVEVHNAKTKPREEQYNSTYRVVSVLTVLHQDWLNGKEYKCKVSNKALPA PIEKTISKAKGQPREPQVYTLPPSRDELTKNQVSLSCAVKGFYPSDIAVEWE SNGQPENNYKTTPPVLDSDGSFFLVSKLTVDKSRWQQGNVFSCSVMHEALHN HYTQKSLSLSPGK | GAA-Fc fusion polypeptide with mature human GAA sequence (underlined) with G$_4$S linker (SEQ ID NO: 62) fused to the N-terminus of an Fc sequence with hole and LALA mutations |
| 49 | GHILLHDFLLVPRELSGSSPVLEETHPAHQQGASRPGPRDAQAHPGRPRAVP TQCDVPPNSREDCAPDKAITQEQCEARGCCYIPAKQGLQGAQMGQPWCFFPP SYPSYKLENLSSSEMGYTATLTRTTPTFFPKDILTLRLDVMMETENRLHFTI KDPANRRYEVPLETPHVHSRAPSPLYSVEFSEEPFGVIVRRQLDGRVLLNTT VAPLFFADQFLQLSTSLPSQYITGLAEHLSPLMLSTSWTRITLWNRDLAPTP GANLYGSHPFYLALEDGGSAHGVFLLNSNAMDVVLQPSPALSWRSTGGILDV YIFLGPEPKSVVQQYLDVVGYPFMPPYWGLGFHLCRWGYSSTAITRQVVENM TRAHFPLDVQWNDLDYMDSRRDFTFNKDGFRDFPAMVQELHQGGRRYMMIVD PAISSSGPAGSYRPYDEGLRRGVFITNETGQPLIGKVWPGSTAFPDFTNPTA LAWWEDMVAEFHDQVPFDGMWIDMNEPSNFIRGSEDGCPNNELENPPYVPGV VGGTLQAATICASSHQFLSTHYNLHNLYGLTEAIASHRALVKARGTRPFVIS RSTFAGHGRYAGHWTGDVWSSWEQLASSVPEILQFNLLGVPLVGADVCGFLG NTSEELCVRWTQLGAFYPFMRNHNSLLSLPQEPYSFSEPAQQAMRKALTLRY ALLPHLYTLFHQAHVAGETVARPLFLEFPKDSSTWTVDHQLLWGEALLITPV LQAGKAEVTGYFPLGTWYDLQTVPVEALGSLPPPPAAPREPAIHSEGQWVTL PAPLDTINVHLRAGYIIPLQGPGLTTTESRQQPMALAVALTKGGEARGELFW DDGESLEVLERGAYTQVIFLARNNTIVNELVRVTSEGAGLQLQKVTVLGVAT APQQVLSNGVPVSNFTYSPDTKVLDICVSLLMGEQFLVSWCGGGGSDKTHTC PPCPAPEAAGGPSVFLFPPKPKDTLMISRTPEVTCVVVDVSHEDPEVKENWY VDGVEVHNAKTKPREEQYNSTYRVVSVLTVLHQDWLNGKEYKCKVSNKALPA PIEKTISKAKGQPREPQVYTLPPSRDELTKNQVSLSCAVKGFYPSDIAVEWE SNGQPENNYKTTPPVLDSDGSFFLVSKLTVDKSRWQQGNVFSCSVMHEALHN HYTQKSLSLSPG | GAA-Fc fusion polypeptide with mature human GAA sequence (underlined) with G$_4$S linker (SEQ ID NO: 62) fused to the N-terminus of an Fc sequence with hole and LALA mutations |
| 50 | AHPGRPRAVPTQCDVPPNSREDCAPDKAITQEQCEARGCCYIPAKQGLQGAQ MGQPWCFFPPSYPSYKLENLSSSEMGYTATLTRTTPTFFPKDILTLRLDVMM ETENRLHFTIKDPANRRYEVPLETPHVHSRAPSPLYSVEFSEEPFGVIVRRQ LDGRVLLNTTVAPLFFADQFLQLSTSLPSQYITGLAEHLSPLMLSTSWTRIT LWNRDLAPTPGANLYGSHPFYLALEDGGSAHGVFLLNSNAMDVVLQPSPALS WRSTGGILDVYIFLGPEPKSVVQQYLDVVGYPFMPPYWGLGFHLCRWGYSST AITRQVVENMTRAHFPLDVQWNDLDYMDSRRDFTFNKDGFRDFPAMVQELHQ GGRRYMMIVDPAISSSGPAGSYRPYDEGLRRGVFITNETGQPLIGKVWPGST AFPDFTNPTALAWWEDMVAEFHDQVPFDGMWIDMNEPSNFIRGSEDGCPNNE LENPPYVPGVVGGTLQAATICASSHQFLSTHYNLHNLYGLTEAIASHRALVK ARGTRPFVISRSTFAGHGRYAGHWTGDVWSSWEQLASSVPEILQFNLLGVPL VGADVCGFLGNTSEELCVRWTQLGAFYPFMRNHNSLLSLPQEPYSFSEPAQQ AMRKALTLRYALLPHLYTLFHQAHVAGETVARPLFLEFPKDSSTWTVDHQLL WGEALLITPVLQAGKAEVTGYFPLGTWYDLQTVPVEALGSLPPPPAAPREPA IHSEGQWVTLPAPLDTINVHLRAGYIIPLQGPGLTTTESRQQPMALAVALTK GGEARGELFWDDGESLEVLERGAYTQVIFLARNNTIVNELVRVTSEGAGLQL QKVTVLGVATAPQQVLSNGVPVSNFTYSPDTKVLDICVSLLMGEQFLVSWCG GGGSDKTHTCPPCPAPEAAGGPSVFLFPPKPKDTLMISRTPEVTCVVVDVSH EDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLSCAVKGF YPSDIAVEWESNGQPENNYKTTPPVLDSDGSFFLVSKLTVDKSRWQQGNVFS CSVMHEALHNHYTQKSLSLSPGK | GAA-Fc fusion polypeptide with a truncated human GAA sequence (underlined), with G$_4$S linker (SEQ ID NO: 62) fused to the N-terminus of an Fc sequence with hole and LALA mutations |

-continued

Informal Sequence Listing

| SEQ ID NO: | Sequence | Description |
|---|---|---|
| 51 | AHPGRPRAVPTQCDVPPNSREDCAPDKAITQEQCEARGCCYIPAKQGLQGAQ<br>MGQPWCFFPPSYPSYKLENLSSSEMGYTATLTRTTPTFFPKDILTLRLDVMM<br>ETENRLHFTIKDPANRRYEVPLETPHVHSRAPSPLYSVEFSEEPFGVIVRRQ<br>LDGRVLLNTTVAPLFFADQFLQLSTSLPSQYITGLAEHLSPLMLSTSWTRIT<br>LWNRDLAPTPGANLYGSHPFYLALEDGGSAHGVFLLNSNAMDVVLQPSPALS<br>WRSTGGILDVYIFLGPEPKSVVQQYLDVVGYPFMPPYWGLGFHLCRWGYSST<br>AITRQVVENMTRAHFPLDVQWNDLDYMDSRRDFTENKDGFRDFPAMVQELHQ<br>GGRRYMMIVDPAISSSGPAGSYRPYDEGLRRGVFITNETGQPLIGKVWPGST<br>AFPDFTNPTALAWWEDMVAEFHDQVPFDGMWIDMNEPSNFIRGSEDGCPNNE<br>LENPPYVPGVVGGTLQAATICASSHQFLSTHYNLHNLYGLTEAIASHRALVK<br>ARGTRPFVISRSTFAGHGRYAGHWTGDVWSSWEQLASSVPEILQFNLLGVPL<br>VGADVCGFLGNTSEELCVRWTQLGAFYPFMRNHNSLLSLPQEPYSFSEPAQQ<br>AMRKALTLRYALLPHLYTLFHQAHVAGETVARPLFLEFPKDSSTWTVDHQLL<br>WGEALLITPVLQAGKAEVTGYFPLGTWYDLQTVPVEALGSLPPPPAAPREPA<br>IHSEGQWVTLPAPLDTINVHLRAGYIIPLQGPGLTTTESRQQPMALAVALTK<br>GGEARGELFWDDGESLEVLERGAYTQVIFLARNNTIVNELVRVTSEGAGLQL<br>QKVTVLGVATAPQQVLSNGVPVSNFTYSPDTKVLDICVSLLMGEQFLVSWCG<br>GGGSDKTHTCPPCPAPEAAGGPSVFLFPPKPKDTLMISRTPEVTCVVVDVSH<br>EDPEVKFNWYVDGVEVHNAKTKPREEQYNSTYRVVSVLTVLHQDWLNGKEYK<br>CKVSNKALPAPIEKTISKAKGQPREPQVYTLPPSRDELTKNQVSLSCAVKGF<br>YPSDIAVEWESNGQPENNYKTTPPVLDSDGSFFLVSKLTVDKSRWQQGNVES<br>CSVMHEALHNHYTQKSLSLSPG | GAA-Fc fusion polypeptide with a truncated human GAA sequence (underlined), with G4S linker (SEQ ID NO: 62) fused to the N-terminus of an Fc sequence with hole and LALA mutations |
| 52 | GHILLHDFLLVPRELSGSSPVLEETHPAHQQGASRPGPRDAQAHPGRPRAVP<br>TQCDVPPNSRFDCAPDKAITQEQCEARGCCYIPAKQGLQGAQMGQPWCFFPP<br>SYPSYKLENLSSSEMGYTATLTRTTPTFFPKDILTLRLDVMMETENRLHFTI<br>KDPANRRYEVPLETPHVHSRAPSPLYSVEFSEEPFGVIVRRQLDGRVLLNTT<br>VAPLFFADQFLQLSTSLPSQYITGLAEHLSPLMLSTSWTRITLWNRDLAPTP<br>GANLYGSHPFYLALEDGGSAHGVFLLNSNAMDVVLQPSPALSWRSTGGILDV<br>YIFLGPEPKSVVQQYLDVVGYPFMPPYWGLGFHLCRWGYSSTAITRQVVENM<br>TRAHFPLDVQWNDLDYMDSRRDFTFNKDGFRDFPAMVQELHQGGRRYMMIVD<br>PAISSSGPAGSYRPYDEGLRRGVFITNETGQPLIGKVWPGSTAFPDFTNPTA<br>LAWWEDMVAEFHDQVPFDGMWIDMNEPSNFIRGSEDGCPNNELENPPYVPGV<br>VGGTLQAATICASSHQFLSTHYNLHNLYGLTEAIASHRALVKARGTRPFVIS<br>RSTFAGHGRYAGHWTGDVWSSWEQLASSVPEILQFNLLGVPLVGADVCGELG<br>NTSEELCVRWTQLGAFYPFMRNHNSLLSLPQEPYSFSEPAQQAMRKALTLRY<br>ALLPHLYTLFHQAHVAGETVARPLFLEFPKDSSTWTVDHQLLWGEALLITPV<br>LQAGKAEVTGYFPLGTWYDLQTVPVEALGSLPPPPAAPREPAIHSEGQWVTL<br>PAPLDTINVHLRAGYIIPLQGPGLTTTESRQQPMALAVALTKGGEARGELFW<br>DDGESLEVLERGAYTQVIFLARNNTIVNELVRVTSEGAGLQLQKVTVLGVAT<br>APQQVLSNGVPVSNFTYSPDTKVLDICVSLLMGEQFLVSWCGGGGSDKTHTC<br>PPCPAPEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALSA<br>PIEKTISKAKGQPREPQVYTLPPSRDELTKNQVSLSCAVKGFYPSDIAVEWE<br>SNGQPENNYKTTPPVLDSDGSFFLVSKLTVDKSRWQQGNVFSCSVMHEALHN<br>HYTQKSLSLSPGK | GAA-Fc fusion polypeptide with mature human GAA sequence (underlined) with G4S linker (SEQ ID NO: 62) fused to the N-terminus of an Fc sequence with hole and LALAPS mutations |
| 53 | GHILLHDFLLVPRELSGSSPVLEETHPAHQQGASRPGPRDAQAHPGRPRAVP<br>TQCDVPPNSRFDCAPDKAITQEQCEARGCCYIPAKQGLQGAQMGQPWCFFPP<br>SYPSYKLENLSSSEMGYTATLTRTTPTFFPKDILTLRLDVMMETENRLHFTI<br>KDPANRRYEVPLETPHVHSRAPSPLYSVEFSEEPFGVIVRRQLDGRVLLNTT<br>VAPLFFADQFLQLSTSLPSQYITGLAEHLSPLMLSTSWTRITLWNRDLAPTP<br>GANLYGSHPFYLALEDGGSAHGVFLLNSNAMDVVLQPSPALSWRSTGGILDV<br>YIFLGPEPKSVVQQYLDVVGYPFMPPYWGLGFHLCRWGYSSTAITRQVVENM<br>TRAHFPLDVQWNDLDYMDSRRDFTENKDGFRDFPAMVQELHQGGRRYMMIVD<br>PAISSSGPAGSYRPYDEGLRRGVFITNETGQPLIGKVWPGSTAFPDFTNPTA<br>LAWWEDMVAEFHDQVPFDGMWIDMNEPSNFIRGSEDGCPNNELENPPYVPGV<br>VGGTLQAATICASSHQFLSTHYNLHNLYGLTEAIASHRALVKARGTRPFVIS<br>RSTFAGHGRYAGHWTGDVWSSWEQLASSVPEILQFNLLGVPLVGADVCGFLG<br>NTSEELCVRWTQLGAFYPFMRNHNSLLSLPQEPYSFSEPAQQAMRKALTLRY<br>ALLPHLYTLFHQAHVAGETVARPLFLEFPKDSSTWTVDHQLLWGEALLITPV<br>LQAGKAEVTGYFPLGTWYDLQTVPVEALGSLPPPPAAPREPAIHSEGQWVTL<br>PAPLDTINVHLRAGYIIPLQGPGLTTTESRQQPMALAVALTKGGEARGELFW<br>DDGESLEVLERGAYTQVIFLARNNTIVNELVRVTSEGAGLQLQKVTVLGVAT<br>APQQVLSNGVPVSNFTYSPDTKVLDICVSLLMGEQFLVSWCGGGGSDKTHTC<br>PPCPAPEAAGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALSA<br>PIEKTISKAKGQPREPQVYTLPPSRDELTKNQVSLSCAVKGFYPSDIAVEWE<br>SNGQPENNYKTTPPVLDSDGSFFLVSKLTVDKSRWQQGNVFSCSVMHEALHN<br>HYTQKSLSLSPG | GAA-Fc fusion polypeptide with mature human GAA sequence (underlined) with G4S linker (SEQ ID NO: 62) fused to the N-terminus of an Fc sequence with hole and LALAPS mutations |

-continued

Informal Sequence Listing

| SEQ ID NO: | Sequence | Description |
|---|---|---|
| 54 | AHPGRPRAVPTQCDVPPNSREDCAPDKAITQEQCEARGCCYIPAKQGLQGAQ<br>MGQPWCFFPPSYPSYKLENLSSSEMGYTATLTRTTPTFFPKDILTLRLDVMM<br>ETENRLHFTIKDPANRRYEVPLETPHVHSRAPSPLYSVEFSEEPFGVIVRRQ<br>LDGRVLLNTTVAPLFFADQFLQLSTSLPSQYITGLAEHLSPLMLSTSWTRIT<br>LWNRDLAPTPGANLYGSHPFYLALEDGGSAHGVFLLNSNAMDVVLQPSPALS<br>WRSTGGILDVYIFLGPEPKSVVQQYLDVVGYPFMPPYWGLGFHLCRWGYSST<br>AITRQVVENMTRAHFPLDVQWNDLDYMDSRRDFTENKDGFRDFPAMVQELHQ<br>GGRRYMMIVDPAISSSGPAGSYRPYDEGLRRGVFITNETGQPLIGKVWPGST<br>AFPDFTNPTALAWWEDMVAEFHDQVPFDGMWIDMNEPSNFIRGSEDGCPNNE<br>LENPPYVPGVVGGTLQAATICASSHQFLSTHYNLHNLYGLTEAIASHRALVK<br>ARGTRPFVISRSTFAGHGRYAGHWTGDVWSSWEQLASSVPEILQFNLLGVPL<br>VGADVCGFLGNTSEELCVRWTQLGAFYPFMRNHNSLLSLPQEPYSFSEPAQQ<br>AMRKALTLRYALLPHLYTLFHQAHVAGETVARPLFLEFPKDSSTWTVDHQLL<br>WGEALLITPVLQAGKAEVTGYFPLGTWYDLQTVPVEALGSLPPPPAAPREPA<br>IHSEGQWVTLPAPLDTINVHLRAGYIIPLQGPGLTTTESRQQPMALAVALTK<br>GGEARGELFWDDGESLEVLERGAYTQVIFLARNNTIVNELVRVTSEGAGLQL<br>QKVTVLGVATAPQQVLSNGVPVSNFTYSPDTKVLDICVSLLMGEQFLVSWCG<br>GGGSDKTHTCPPCPAPEAAGGPSVFLFPPKPKDTLMISRTPEVTCVVVDVSH<br>EDPEVKFNWYVDGVEVHNAKTKPREEQYNSTYRVVSVLTVLHQDWLNGKEYK<br>CKVSNKALSAPIEKTISKAKGQPREPQVYTLPPSRDELTKNQVSLSCAVKGF<br>YPSDIAVEWESNGQPENNYKTTPPVLDSDGSFFLVSKLTVDKSRWQQGNVES<br>CSVMHEALHNHYTQKSLSLSPGK | GAA-Fc fusion polypeptide with a truncated human GAA sequence (underlined), with G$_4$S linker (SEQ ID NO: 62) fused to the N-terminus of an Fc sequence with hole and LALAPS mutations |
| 55 | AHPGRPRAVPTQCDVPPNSREDCAPDKAITQEQCEARGCCYIPAKQGLQGAQ<br>MGQPWCFFPPSYPSYKLENLSSSEMGYTATLTRTTPTFFPKDILTLRLDVMM<br>ETENRLHFTIKDPANRRYEVPLETPHVHSRAPSPLYSVEFSEEPFGVIVRRQ<br>LDGRVLLNTTVAPLFFADQFLQLSTSLPSQYITGLAEHLSPLMLSTSWTRIT<br>LWNRDLAPTPGANLYGSHPFYLALEDGGSAHGVFLLNSNAMDVVLQPSPALS<br>WRSTGGILDVYIFLGPEPKSVVQQYLDVVGYPFMPPYWGLGFHLCRWGYSST<br>AITRQVVENMTRAHFPLDVQWNDLDYMDSRRDFTENKDGFRDFPAMVQELHQ<br>GGRRYMMIVDPAISSSGPAGSYRPYDEGLRRGVFITNETGQPLIGKVWPGST<br>AFPDFTNPTALAWWEDMVAEFHDQVPFDGMWIDMNEPSNFIRGSEDGCPNNE<br>LENPPYVPGVVGGTLQAATICASSHQFLSTHYNLHNLYGLTEAIASHRALVK<br>ARGTRPFVISRSTFAGHGRYAGHWTGDVWSSWEQLASSVPEILQFNLLGVPL<br>VGADVCGFLGNTSEELCVRWTQLGAFYPFMRNHNSLLSLPQEPYSFSEPAQQ<br>AMRKALTLRYALLPHLYTLFHQAHVAGETVARPLFLEFPKDSSTWTVDHQLL<br>WGEALLITPVLQAGKAEVTGYFPLGTWYDLQTVPVEALGSLPPPPAAPREPA<br>IHSEGQWVTLPAPLDTINVHLRAGYIIPLQGPGLTTTESRQQPMALAVALTK<br>GGEARGELFWDDGESLEVLERGAYTQVIFLARNNTIVNELVRVTSEGAGLQL<br>QKVTVLGVATAPQQVLSNGVPVSNFTYSPDTKVLDICVSLLMGEQFLVSWCG<br>GGGSDKTHTCPPCPAPEAAGGPSVFLFPPKPKDTLMISRTPEVTCVVVDVSH<br>EDPEVKFNWYVDGVEVHNAKTKPREEQYNSTYRVVSVLTVLHQDWLNGKEYK<br>CKVSNKALSAPIEKTISKAKGQPREPQVYTLPPSRDELTKNQVSLSCAVKGF<br>YPSDIAVEWESNGQPENNYKTTPPVLDSDGSFFLVSKLTVDKSRWQQGNVFS<br>CSVMHEALHNHYTQKSLSLSPG | GAA-Fc fusion polypeptide with a truncated human GAA sequence (underlined), with G$_4$S linker (SEQ ID NO: 62) fused to the N-terminus of an Fc sequence with hole and LALAPS mutations |
| 56 | DKTHTCPPCPAPEAAGGPSVFLFPPKPKDTLMISRTPEVTCVVVDVSHEDPE<br>VKFNWYVDGVEVHNAKTKPREEQYNSTYRVVSVLTVLHQDWLNGKEYKCKVS<br>NKALPAPIEKTISKAKGQPREPQVYTLPPSRDELTKNQVSLSCAVKGFYPSD<br>IAVEWESNGQPENNYKTTPPVLDSDGSFFLVSKLTVDKSRWQQGNVFSCSVM<br>HEALHNHYTQKSLSLSPGKGGGGSGHILLHDFLLVPRELSGSSPVLEETHPA<br>HQQGASRPGPRDAQAHPGRPRAVPTQCDVPPNSREDCAPDKAITQEQCEARG<br>CCYIPAKQGLQGAQMGQPWCFFPPSYPSYKLENLSSSEMGYTATLTRTTPTF<br>FPKDILTLRLDVMMETENRLHFTIKDPANRRYEVPLETPHVHSRAPSPLYSV<br>EFSEEPFGVIVRRQLDGRVLLNTTVAPLFFADQFLQLSTSLPSQYITGLAEH<br>LSPLMLSTSWTRITLWNRDLAPTPGANLYGSHPFYLALEDGGSAHGVFLLNS<br>NAMDVVLQPSPALSWRSTGGILDVYIFLGPEPKSVVQQYLDVVGYPFMPPYW<br>GLGFHLCRWGYSSTAITRQVVENMTRAHFPLDVQWNDLDYMDSRRDFTENKD<br>GFRDFPAMVQELHQGGRRYMMIVDPAISSSGPAGSYRPYDEGLRRGVFITNE<br>TGQPLIGKVWPGSTAFPDFTNPTALAWWEDMVAEFHDQVPFDGMWIDMNEPS<br>NFIRGSEDGCPNNELENPPYVPGVVGGTLQAATICASSHQFLSTHYNLHNLY<br>GLTEAIASHRALVKARGTRPFVISRSTFAGHGRYAGHWTGDVWSSWEQLASS<br>VPEILQFNLLGVPLVGADVCGFLGNTSEELCVRWTQLGAFYPFMRNHNSLLS<br>LPQEPYSFSEPAQQAMRKALTLRYALLPHLYTLFHQAHVAGETVARPLFLEF<br>PKDSSTWTVDHQLLWGEALLITPVLQAGKAEVTGYFPLGTWYDLQTVPVEAL<br>GSLPPPPAAPREPAIHSEGQWVTLPAPLDTINVHLRAGYIIPLQGPGLTTTE<br>SRQQPMALAVALTKGGEARGELFWDDGESLEVLERGAYTQVIFLARNNTIVN<br>ELVRVTSEGAGLQLQKVTVLGVATAPQQVLSNGVPVSNFTYSPDTKVLDICV<br>SLLMGEQFLVSWC | Fc-GAA fusion polypeptide with mature human GAA sequence (underlined) with G$_4$S linker (SEQ ID NO: 62) fused to the C-terminus of an Fc sequence with hole and LALA mutations |

| SEQ ID NO: Sequence | Description |
|---|---|
| 57 DKTHTCPPCPAPEAAGGPSVFLFPPKPKDTLMISRTPEVTCVVVDVSHEDPE<br>VKFNWYVDGVEVHNAKTKPREEQYNSTYRVVSVLTVLHQDWLNGKEYKCKVS<br>NKALPAPIEKTISKAKGQPREPQVYTLPPSRDELTKNQVSLSCAVKGFYPSD<br>IAVEWESNGQPENNYKTTPPVLDSDGSFFLVSKLTVDKSRWQQGNVFSCSVM<br>HEALHNHYTQKSLSLSPGKGGGGS<u>AHPGRPRAVPTQCDVPPNSREDCAPDKA<br>ITQEQCEARGCCYIPAKQGLQGAQMGQPWCFFPPSYPSYKLENLSSSEMGYT<br>ATLTRTTPTFFPKDILTLRLDVMMETENRLHFTIKDPANRRYEVPLETPHVH<br>SRAPSPLYSVEFSEEPFGVIVRRQLDGRVLLNTTVAPLFFADQFLQLSTSLP<br>SQYITGLAEHLSPLMLSTSWTRITLWNRDLAPTPGANLYGSHPFYLALEDGG<br>SAHGVFLLNSNAMDVVLQPSPALSWRSTGGILDVYIFLGPEPKSVVQQYLDV<br>VGYPFMPPYWGLGFHLCRWGYSSTAITRQVVENMTRAHFPLDVQWNDLDYMD<br>SRRDFTENKDGFRDFPAMVQELHQGGRRYMMIVDPAISSSGPAGSYRPYDEG<br>LRRGVFITNETGQPLIGKVWPGSTAFPDFTNPTALAWWEDMVAEFHDQVPED<br>GMWIDMNEPSNFIRGSEDGCPNNELENPPYVPGVVGGTLQAATICASSHQFL<br>STHYNLHNLYGLTEAIASHRALVKARGTRPFVISRSTFAGHGRYAGHWTGDV<br>WSSWEQLASSVPEILQFNLLGVPLVGADVCGFLGNTSEELCVRWTQLGAFYP<br>FMRNHNSLLSLPQEPYSFSEPAQQAMRKALTLRYALLPHLYTLFHQAHVAGE<br>TVARPLFLEFPKDSSTWTVDHQLLWGEALLITPVLQAGKAEVTGYFPLGTWY<br>DLQTVPVEALGSLPPPPAAPREPAIHSEGQWVTLPAPLDTINVHLRAGYIIP<br>LQGPGLTTTESRQQPMALAVALTKGGEARGELFWDDGESLEVLERGAYTQVI<br>FLARNNTIVNELVRVTSEGAGLQLQKVTVLGVATAPQQVLSNGVPVSNFTYS<br>PDTKVLDICVSLLMGEQFLVSWC</u> | Fc-GAA fusion polypeptide with a truncated human GAA sequence (underlined) with G<sub>4</sub>S linker (SEQ ID NO: 62) fused to the C-terminus of an Fc sequence with hole and LALA mutations |
| 58 DKTHTCPPCPAPEAAGGPSVFLFPPKPKDTLMISRTPEVTCVVVDVSHEDPE<br>VKFNWYVDGVEVHNAKTKPREEQYNSTYRVVSVLTVLHQDWLNGKEYKCKVS<br>NKALSAPIEKTISKAKGQPREPQVYTLPPSRDELTKNQVSLSCAVKGFYPSD<br>IAVEWESNGQPENNYKTTPPVLDSDGSFFLVSKLTVDKSRWQQGNVFSCSVM<br>HEALHNHYTQKSLSLSPGKGGGGS<u>GHILLHDFLLVPRELSGSSPVLEETHPA<br>HQQGASRPGPRDAQAHPGRPRAVPTQCDVPPNSRFDCAPDKAITQEQCEARG<br>CCYIPAKQGLQGAQMGQPWCFFPPSYPSYKLENLSSSEMGYTATLTRTTPTF<br>FPKDILTLRLDVMMETENRLHFTIKDPANRRYEVPLETPHVHSRAPSPLYSV<br>EFSEEPFGVIVRRQLDGRVLLNTTVAPLFFADQFLQLSTSLPSQYITGLAEH<br>LSPLMLSTSWTRITLWNRDLAPTPGANLYGSHPFYLALEDGGSAHGVELLNS<br>NAMDVVLQPSPALSWRSTGGILDVYIFLGPEPKSVVQQYLDVVGYPFMPPYW<br>GLGFHLCRWGYSSTAITRQVVENMTRAHFPLDVQWNDLDYMDSRRDFTENKD<br>GFRDFPAMVQELHQGGRRYMMIVDPAISSSGPAGSYRPYDEGLRRGVFITNE<br>TGQPLIGKVWPGSTAFPDFTNPTALAWWEDMVAEFHDQVPFDGMWIDMNEPS<br>NFIRGSEDGCPNNELENPPYVPGVVGGTLQAATICASSHQFLSTHYNLHNLY<br>GLTEAIASHRALVKARGTRPFVISRSTFAGHGRYAGHWTGDVWSSWEQLASS<br>VPEILQFNLLGVPLVGADVCGFLGNTSEELCVRWTQLGAFYPFMRNHNSLLS<br>LPQEPYSFSEPAQQAMRKALTLRYALLPHLYTLFHQAHVAGETVARPLFLEF<br>PKDSSTWTVDHQLLWGEALLITPVLQAGKAEVTGYFPLGTWYDLQTVPVEAL<br>GSLPPPPAAPREPAIHSEGQWVTLPAPLDTINVHLRAGYIIPLQGPGLTTTE<br>SRQQPMALAVALTKGGEARGELFWDDGESLEVLERGAYTQVIFLARNNTIVN<br>ELVRVTSEGAGLQLQKVTVLGVATAPQQVLSNGVPVSNFTYSPDTKVLDICV<br>SLLMGEQFLVSWC</u> | Fc-GAA fusion polypeptide with mature human GAA sequence (underlined) with G<sub>4</sub>S linker (SEQ ID NO: 62) fused to the C-terminus of an Fc sequence with hole and LALAPS mutations |
| 59 DKTHTCPPCPAPEAAGGPSVFLFPPKPKDTLMISRTPEVTCVVVDVSHEDPE<br>VKFNWYVDGVEVHNAKTKPREEQYNSTYRVVSVLTVLHQDWLNGKEYKCKVS<br>NKALSAPIEKTISKAKGQPREPQVYTLPPSRDELTKNQVSLSCAVKGFYPSD<br>IAVEWESNGQPENNYKTTPPVLDSDGSFFLVSKLTVDKSRWQQGNVFSCSVM<br>HEALHNHYTQKSLSLSPGKGGGGS<u>AHPGRPRAVPTQCDVPPNSREDCAPDKA<br>ITQEQCEARGCCYIPAKQGLQGAQMGQPWCFFPPSYPSYKLENLSSSEMGYT<br>ATLTRTTPTFFPKDILTLRLDVMMETENRLHFTIKDPANRRYEVPLETPHVH<br>SRAPSPLYSVEFSEEPFGVIVRRQLDGRVLLNTTVAPLFFADQFLQLSTSLP<br>SQYITGLAEHLSPLMLSTSWTRITLWNRDLAPTPGANLYGSHPFYLALEDGG<br>SAHGVFLLNSNAMDVVLQPSPALSWRSTGGILDVYIFLGPEPKSVVQQYLDV<br>VGYPFMPPYWGLGFHLCRWGYSSTAITRQVVENMTRAHFPLDVQWNDLDYMD<br>SRRDFTENKDGFRDFPAMVQELHQGGRRYMMIVDPAISSSGPAGSYRPYDEG<br>LRRGVFITNETGQPLIGKVWPGSTAFPDFTNPTALAWWEDMVAEFHDQVPFD<br>GMWIDMNEPSNFIRGSEDGCPNNELENPPYVPGVVGGTLQAATICASSHQFL<br>STHYNLHNLYGLTEAIASHRALVKARGTRPFVISRSTFAGHGRYAGHWTGDV<br>WSSWEQLASSVPEILQFNLLGVPLVGADVCGFLGNTSEELCVRWTQLGAFYP<br>FMRNHNSLLSLPQEPYSFSEPAQQAMRKALTLRYALLPHLYTLFHQAHVAGE<br>TVARPLFLEFPKDSSTWTVDHQLLWGEALLITPVLQAGKAEVTGYFPLGTWY<br>DLQTVPVEALGSLPPPPAAPREPAIHSEGQWVTLPAPLDTINVHLRAGYIIP<br>LQGPGLTTTESRQQPMALAVALTKGGEARGELFWDDGESLEVLERGAYTQVI<br>FLARNNTIVNELVRVTSEGAGLQLQKVTVLGVATAPQQVLSNGVPVSNFTYS<br>PDTKVLDICVSLLMGEQFLVSWC</u> | Fc-GAA fusion polypeptide with a truncated human GAA sequence (underlined) with G<sub>4</sub>S linker (SEQ ID NO: 62) fused to the C-terminus of an Fc sequence with hole and LALAPS mutations |

| SEQ ID NO: | Sequence | Description |
|---|---|---|
| 60 | MGWSCIILFLVATATGAYA | Secretion signal peptide |
| | GS | GS linker |
| 62 | GGGGS | Glycine-rich linker |
| 63 | GGGGSGGGGS | Glycine-rich linker |
| 64 | MGVRHPPCSHRLLAVCALVSLATAALLGHILLHDFLLVPRELSGSSPVLEET HPAHQQGASRPGPRDAQAHPGRPRAVPTQCDVPPNSREDCAPDKAITQEQCE ARGCCYIPAKQGLQGAQMGQPWCFFPPSYPSYKLENLSSSEMGYTATLTRTT PTFFPKDILTLRLDVMMETENRLHFTIKDPANRRYEVPLETPRVHSRAPSPL YSVEFSEEPFGVIVHRQLDGRVLLNTTVAPLFFADQFLQLSTSLPSQYITGL AEHLSPLMLSTSWTRITLWNRDLAPTPGANLYGSHPFYLALEDGGSAHGVFL LNSNAMDVVLQPSPALSWRSTGGILDVYIFLGPEPKSVVQQYLDVVGYPFMP PYWGLGFHLCRWGYSSTAITRQVVENMTRAHFPLDVQWNDLDYMDSRRDFTF NKDGFRDFPAMVQELHQGGRRYMMIVDPAISSSGPAGSYRPYDEGLRRGVFI TNETGQPLIGKVWPGSTAFPDFTNPTALAWWEDMVAEFHDQVPFDGMWIDMN EPSNFIRGSEDGCPNNELENPPYVPGVVGGTLQAATICASSHQFLSTHYNLH NLYGLTEAIASHRALVKARGTRPFVISRSTFAGHGRYAGHWTGDVWSSWEQL ASSVPEILQFNLLGVPLVGADVCGFLGNTSEELCVRWTQLGAFYPPMRNHNS LLSLPQEPYSFSEPAQQAMRKALTLRYALLPHLYTLFHQAHVAGETVARPLF LEFPKDSSTWTVDHQLLWGEALLITPVLQAGKAEVTGYFPLGTWYDLQTVPI EALGSLPPPPAAPREPAIHSEGQWVTLPAPLDTINVHLRAGYIIPLQGPGLT TTESRQQPMALAVALTKGGEARGELFWDDGESLEVLERGAYTQVIFLARNNT IVNELVRVTSEGAGLQLQKVTVLGVATAPQQVLSNGVPVSNFTYSPDTKVLD ICVSLLMGEQFLVSWC | Embodiment of a full-length human acid alpha-glucosidase (GAA) polypeptide sequence comprising H199R, R223H, V780I, wherein positions and substitutions are relative to SEQ ID NO: 45 |
| 65 | GHILLHDFLLVPRELSGSSPVLEETHPAHQQGASRPGPRDAQAHPGRPRAVP TQCDVPPNSREDCAPDKAITQEQCEARGCCYIPAKQGLQGAQMGQPWCFFPP SYPSYKLENLSSSEMGYTATLTRTTPTFFPKDILTLRLDVMMETENRLHFTI KDPANRRYEVPLETPRVHSRAPSPLYSVEFSEEPFGVIVHRQLDGRVLLNTT VAPLFFADQFLQLSTSLPSQYITGLAEHLSPLMLSTSWTRITLWNRDLAPTP GANLYGSHPFYLALEDGGSAHGVFLLNSNAMDVVLQPSPALSWRSTGGILDV YIFLGPEPKSVVQQYLDVVGYPFMPPYWGLGFHLCRWGYSSTAITRQVVENM TRAHFPLDVQWNDLDYMDSRRDFTENKDGFRDFPAMVQELHQGGRRYMMIVD PAISSSGPAGSYRPYDEGLRRGVFITNETGQPLIGKVWPGSTAFPDFTNPTA LAWWEDMVAEFHDQVPFDGMWIDMNEPSNFIRGSEDGCPNNELENPPYVPGV VGGTLQAATICASSHQFLSTHYNLHNLYGLTEAIASHRALVKARGTRPFVIS RSTFAGHGRYAGHWTGDVWSSWEQLASSVPEILQFNLLGVPLVGADVCGFLG NTSEELCVRWTQLGAFYPPMRNHNSLLSLPQEPYSFSEPAQQAMRKALTLRY ALLPHLYTLFHQAHVAGETVARPLFLEFPKDSSTWTVDHQLLWGEALLITPV LQAGKAEVTGYFPLGTWYDLQTVPIEALGSLPPPPAAPREPAIHSEGQWVTL PAPLDTINVHLRAGYIIPLQGPGLTTTESRQQPMALAVALTKGGEARGELFW DDGESLEVLERGAYTQVIFLARNNTIVNELVRVTSEGAGLQLQKVTVLGVAT APQQVLSNGVPVSNFTYSPDTKVLDICVSLLMGEQFLVSWC | Embodiment of a mature human acid alpha-glucosidase (GAA) polypeptide sequence comprising H199R, R223H, V780I, wherein positions and substitutions are relative to SEQ ID NO: 45 |
| 66 | AHPGRPRAVPTQCDVPPNSREDCAPDKAITQEQCEARGCCYIPAKQGLQGAQ MGQPWCFFPPSYPSYKLENLSSSEMGYTATLTRTTPTFFPKDILTLRLDVMM ETENRLHFTIKDPANRRYEVPLETPRVHSRAPSPLYSVEFSEEPFGVIVHRQ LDGRVLLNTTVAPLFFADQFLQLSTSLPSQYITGLAEHLSPLMLSTSWTRIT LWNRDLAPTPGANLYGSHPFYLALEDGGSAHGVFLLNSNAMDVVLQPSPALS WRSTGGILDVYIFLGPEPKSVVQQYLDVVGYPFMPPYWGLGFHLCRWGYSST AITRQVVENMTRAHFPLDVQWNDLDYMDSRRDFTENKDGFRDFPAMVQELHQ GGRRYMMIVDPAISSSGPAGSYRPYDEGLRRGVFITNETGQPLIGKVWPGST AFPDFTNPTALAWWEDMVAEFHDQVPFDGMWIDMNEPSNFIRGSEDGCPNNE LENPPYVPGVVGGTLQAATICASSHQFLSTHYNLHNLYGLTEAIASHRALVK ARGTRPFVISRSTFAGHGRYAGHWTGDVWSSWEQLASSVPEILQFNLLGVPL VGADVCGFLGNTSEELCVRWTQLGAFYPPMRNHNSLLSLPQEPYSFSEPAQQ AMRKALTLRYALLPHLYTLFHQAHVAGETVARPLFLEFPKDSSTWTVDHQLL WGEALLITPVLQAGKAEVTGYFPLGTWYDLQTVPIEALGSLPPPPAAPREPA IHSEGQWVTLPAPLDTINVHLRAGYIIPLQGPGLTTTESRQQPMALAVALTK GGEARGELFWDDGESLEVLERGAYTQVIFLARNNTIVNELVRVTSEGAGLQL QKVTVLGVATAPQQVLSNGVPVSNFTYSPDTKVLDICVSLLMGEQFLVSWC | Embodiment of a truncated human acid alpha-glucosidase (GAA) polypeptide sequence comprising H199R, R223H, V780I, wherein positions and substitutions are relative to SEQ ID NO: 45 |

| Informal Sequence Listing | |
|---|---|
| SEQ ID NO: Sequence | Description |

67 DKTHTCPPCPAPEAAGGPSVFLFPPKPKDTLMISRTPEVTCVVVDVSHEDPE
VKFNWYVDGVEVHNAKTKPREEQYNSTYRVVSVLTVLHQDWLNGKEYKCKVS
NKALPAPIEKTISKAKGQPREPQVYTLPPSRDELTKNQVSLSCAVKGFYPSD
IAVEWESNGQPENNYKTTPPVLDSDGSFFLVSKLTVDKSRWQQGNVFSCSVM
HEALHNHYTQKSLSLSPGKGGGGSGHILLHDFLLVPRELSGSSPVLEETHPA
HQQGASRPGPRDAQAHPGRPRAVPTQCDVPPNSREDCAPDKAITQEQCEARG
CCYIPAKQGLQGAQMGQPWCFFPPSYPSYKLENLSSSEMGYTATLTRTTPTF
FPKDILTLRLDVMMETENRLHFTIKDPANRRYEVPLETPRVHSRAPSPLYSV
EFSEEPFGVIVHRQLDGRVLLNTTVAPLFFADQFLQLSTSLPSQYITGLAEH
LSPLMLSTSWTRITLWNRDLAPTPGANLYGSHPFYLALEDGGSAHGVFLLNS
NAMDVVLQPSPALSWRSTGGILDVYIFLGPEPKSVVQQYLDVVGYPFMPPYW
GLGFHLCRWGYSSTAITRQVVENMTRAHFPLDVQWNDLDYMDSRRDFTENKD
GFRDFPAMVQELHQGGRRYMMIVDPAISSSGPAGSYRPYDEGLRRGVFITNE
TGQPLIGKVWPGSTAFPDFTNPTALAWWEDMVAEFHDQVPFDGMWIDMNEPS
NFIRGSEDGCPNNELENPPYVPGVVGGTLQAATICASSHQFLSTHYNLHNLY
GLTEAIASHRALVKARGTRPFVISRSTFAGHGRYAGHWTGDVWSSWEQLASS
VPEILQFNLLGVPLVGADVCGFLGNTSEELCVRWTQLGAFYPFMRNHNSLLS
LPQEPYSFSEPAQQAMRKALTLRYALLPHLYTLFHQAHVAGETVARPLFLEF
PKDSSTWTVDHQLLWGEALLITPVLQAGKAEVTGYFPLGTWYDLQTVPIEAL
GSLPPPPAAPREPAIHSEGQWVTLPAPLDTINVHLRAGYIIPLQGPGLTTTE
SRQQPMALAVALTKGGEARGELFWDDGESLEVLERGAYTQVIFLARNNTIVN
ELVRVTSEGAGLQLQKVTVLGVATAPQQVLSNGVPVSNFTYSPDTKVLDICV
SLLMGEQFLVSWC
 | Fc-GAA fusion polypeptide with a mature human GAA sequence [H199R, R223H, V780I] (underlined) with G$_4$S linker (SEQ ID NO: 62) fused to the C-terminus of an Fc sequence with hole and LALA mutations |

68 DKTHTCPPCPAPEAAGGPSVFLFPPKPKDTLMISRTPEVTCVVVDVSHEDPE
VKFNWYVDGVEVHNAKTKPREEQYNSTYRVVSVLTVLHQDWLNGKEYKCKVS
NKALPAPIEKTISKAKGQPREPQVYTLPPSRDELTKNQVSLSCAVKGFYPSD
IAVEWESNGQPENNYKTTPPVLDSDGSFFLVSKLTVDKSRWQQGNVFSCSVM
HEALHNHYTQKSLSLSPGKGGGGSAHPGRPRAVPTQCDVPPNSREDCAPDKA
ITQEQCEARGCCYIPAKQGLQGAQMGQPWCFFPPSYPSYKLENLSSSEMGYT
ATLTRTTPTFFPKDILTLRLDVMMETENRLHFTIKDPANRRYEVPLETPRVH
SRAPSPLYSVEFSEEPFGVIVHRQLDGRVLLNTTVAPLFFADQFLQLSTSLP
SQYITGLAEHLSPLMLSTSWTRITLWNRDLAPTPGANLYGSHPFYLALEDGG
SAHGVFLLNSNAMDVVLQPSPALSWRSTGGILDVYIFLGPEPKSVVQQYLDV
VGYPFMPPYWGLGFHLCRWGYSSTAITRQVVENMTRAHFPLDVQWNDLDYMD
SRRDFTENKDGFRDFPAMVQELHQGGRRYMMIVDPAISSSGPAGSYRPYDEG
LRRGVFITNETGQPLIGKVWPGSTAFPDFTNPTALAWWEDMVAEFHDQVPED
GMWIDMNEPSNFIRGSEDGCPNNELENPPYVPGVVGGTLQAATICASSHQFL
STHYNLHNLYGLTEAIASHRALVKARGTRPFVISRSTFAGHGRYAGHWTGDV
WSSWEQLASSVPEILQFNLLGVPLVGADVCGFLGNTSEELCVRWTQLGAFYP
FMRNHNSLLSLPQEPYSFSEPAQQAMRKALTLRYALLPHLYTLFHQAHVAGE
TVARPLFLEFPKDSSTWTVDHQLLWGEALLITPVLQAGKAEVTGYFPLGTWY
DLQTVPIEALGSLPPPPAAPREPAIHSEGQWVTLPAPLDTINVHLRAGYIIP
LQGPGLTTTESRQQPMALAVALTKGGEARGELFWDDGESLEVLERGAYTQVI
FLARNNTIVNELVRVTSEGAGLQLQKVTVLGVATAPQQVLSNGVPVSNFTYS
PDTKVLDICVSLLMGEQFLVSWC
 | Fc-GAA fusion polypeptide with a truncated human GAA sequence [H199R, R223H, V780I] (underlined) with G$_4$S linker (SEQ ID NO: 62) fused to the C-terminus of an Fc sequence with hole and LALA mutations |

69 DKTHTCPPCPAPEAAGGPSVFLFPPKPKDTLMISRTPEVTCVVVDVSHEDPE
VKFNWYVDGVEVHNAKTKPREEQYNSTYRVVSVLTVLHQDWLNGKEYKCKVS
NKALSAPIEKTISKAKGQPREPQVYTLPPSRDELTKNQVSLSCAVKGFYPSD
IAVEWESNGQPENNYKTTPPVLDSDGSFFLVSKLTVDKSRWQQGNVFSCSVM
HEALHNHYTQKSLSLSPGKGGGGSGHILLHDFLLVPRELSGSSPVLEETHPA
HQQGASRPGPRDAQAHPGRPRAVPTQCDVPPNSREDCAPDKAITQEQCEARG
CCYIPAKQGLQGAQMGQPWCFFPPSYPSYKLENLSSSEMGYTATLTRTTPTF
FPKDILTLRLDVMMETENRLHFTIKDPANRRYEVPLETPRVHSRAPSPLYSV
EFSEEPFGVIVHRQLDGRVLLNTTVAPLFFADQFLQLSTSLPSQYITGLAEH
LSPLMLSTSWTRITLWNRDLAPTPGANLYGSHPFYLALEDGGSAHGVFLLNS
NAMDVVLQPSPALSWRSTGGILDVYIFLGPEPKSVVQQYLDVVGYPFMPPYW
GLGFHLCRWGYSSTAITRQVVENMTRAHFPLDVQWNDLDYMDSRRDFTENKD
GFRDFPAMVQELHQGGRRYMMIVDPAISSSGPAGSYRPYDEGLRRGVFITNE
TGQPLIGKVWPGSTAFPDFTNPTALAWWEDMVAEFHDQVPFDGMWIDMNEPS
NFIRGSEDGCPNNELENPPYVPGVVGGTLQAATICASSHQFLSTHYNLHNLY
GLTEAIASHRALVKARGTRPFVISRSTFAGHGRYAGHWTGDVWSSWEQLASS
VPEILQFNLLGVPLVGADVCGFLGNTSEELCVRWTQLGAFYPFMRNHNSLLS
LPQEPYSFSEPAQQAMRKALTLRYALLPHLYTLFHQAHVAGETVARPLFLEF
PKDSSTWTVDHQLLWGEALLITPVLQAGKAEVTGYFPLGTWYDLQTVPIEAL
GSLPPPPAAPREPAIHSEGQWVTLPAPLDTINVHLRAGYIIPLQGPGLTTTE
SRQQPMALAVALTKGGEARGELFWDDGESLEVLERGAYTQVIFLARNNTIVN
ELVRVTSEGAGLQLQKVTVLGVATAPQQVLSNGVPVSNFTYSPDTKVLDICV
SLLMGEQFLVSWC
 | Fc-GAA fusion polypeptide with a mature human GAA sequence [H199R, R223H, V780I] (underlined) with G$_4$S linker (SEQ ID NO: 62) fused to the C-terminus of an Fc sequence with hole and LALAPS mutations |

| Informal Sequence Listing | |
|---|---|
| SEQ ID NO: Sequence | Description |
| 70 DKTHTCPPCPAPEAAGGPSVFLFPPKPKDTLMISRTPEVTCVVVDVSHEDPE<br>VKFNWYVDGVEVHNAKTKPREEQYNSTYRVVSVLTVLHQDWLNGKEYKCKVS<br>NKALSAPIEKTISKAKGQPREPQVYTLPPSRDELTKNQVSLSCAVKGFYPSD<br>IAVEWESNGQPENNYKTTPPVLDSDGSFFLVSKLTVDKSRWQQGNVFSCSVM<br>HEALHNHYTQKSLSLSPGKGGGGS<u>AHPGRPRAVPTQCDVPPNSREDCAPDKA<br>ITQEQCEARGCCYIPAKQGLQGAQMGQPWCFFPPSYPSYKLENLSSSEMGYT<br>ATLTRTTPTFFPKDILTLRLDVMMETENRLHFTIKDPANRRYEVPLETPRVH<br>SRAPSPLYSVEFSEEPFGVIVHRQLDGRVLLNTTVAPLFFADQFLQLSTSLP<br>SQYITGLAEHLSPLMLSTSWTRITLWNRDLAPTPGANLYGSHPFYLALEDGG<br>SAHGVFLLNSNAMDVVLQPSPALSWRSTGGILDVYIFLGPEPKSVVQQYLDV<br>VGYPFMPPYWGLGFHLCRWGYSSTAITRQVVENMTRAHFPLDVQWNDLDYMD<br>SRRDFTENKDGFRDFPAMVQELHQGGRRYMMIVDPAISSSGPAGSYRPYDEG<br>LRRGVFITNETGQPLIGKVWPGSTAFPDFTNPTALAWWEDMVAEFHDQVPFD<br>GMWIDMNEPSNFIRGSEDGCPNNELENPPYVPGVVGGTLQAATICASSHQFL<br>STHYNLHNLYGLTEAIASHRALVKARGTRPPFVISRSTFAGHGRYAGHWTGDV</u><br>WSSWEQLASSVPEILQFNLLGVPLVGADVCGFLGNTSEELCVRWTQLGAFYP<br>FMRNHNSLLSLPQEPYSFSEPAQQAMRKALTLRYALLPHLYTLFHQAHVAGE<br>TVARPLFLEFPKDSSTWTVDHQLLWGEALLITPVLQAGKAEVTGYFPLGTWY<br>DLQTVPIEALGSLPPPPAAPREPAIHSEGQWVTLPAPLDTINVHLRAGYIIP<br>LQGPGLTTTESRQQPMALAVALTKGGEARGELFWDDGESLEVLERGAYTQVI<br>FLARNNTIVNELVRVTSEGAGLQLQKVTVLGVATAPQQVLSNGVPVSNFTYS<br>PDTKVLDICVSLLMGEQFLVSWC | Fc-GAA fusion polypeptide with a truncated human GAA sequence [H199R, R223H, V780I] (underlined) with G₄S linker (SEQ ID NO: 62) fused to the C-terminus of an Fc sequence with hole and LALAPS mutations |

All publications, patents, and patent documents are incorporated by reference herein, as though individually incorporated by reference. The present disclosure has been described with reference to various specific and preferred embodiments and techniques. However, it should be understood that many variations and modifications may be made while remaining within the spirit and scope of the invention.

What is claimed is:

1. A protein comprising
   a fusion polypeptide comprising a first Fc polypeptide linked to an acid alpha-glucosidase (GAA) enzyme; and
   a second Fc polypeptide; wherein:
   (a) the fusion polypeptide comprises SEQ ID NO: 68; and the second Fc polypeptide comprises any one of SEQ ID NOs: 41-42; or
   (b) the fusion polypeptide comprises SEQ ID NO: 70; and the second Fc polypeptide comprises any one of SEQ ID NOs:43-44.

2. The protein of claim 1, wherein the fusion polypeptide comprises SEQ ID NO: 70; and wherein the second Fc polypeptide comprises any one of SEQ ID NOs: 43-44.

3. The protein of claim 1, wherein the fusion polypeptide comprises SEQ ID NO: 68; and wherein the second Fc polypeptide comprises any one of SEQ ID NOs: 41-42.

4. The protein of claim 1, wherein uptake of the GAA enzyme into the brain is at least five-fold greater as compared to the uptake of the GAA enzyme in the absence of the first Fc polypeptide and the second Fc polypeptide or as compared to the uptake of the GAA enzyme without the modifications to the second Fc polypeptide that result in TfR binding.

5. The protein of claim 1, wherein the protein does not include an immunoglobulin heavy and/or light chain variable region sequence or an antigen-binding portion thereof.

6. A composition comprising the protein of claim 1 and a pharmaceutically acceptable excipient.

7. A pair of polynucleotides comprising a first and a second polynucleotide, wherein the first polynucleotide comprises a first nucleic acid sequence encoding the fusion polypeptide; and the second polynucleotide comprises a second nucleic acid sequence encoding the second Fc polypeptide, wherein the fusion polypeptide and the second Fc polypeptide are as recited in claim 1.

8. One or more vectors comprising the pair of polynucleotides of claim 7.

9. A host cell comprising the pair of polynucleotides of claim 7.

10. A method for producing a protein comprising a fusion polypeptide comprising a first Fc polypeptide linked to a GAA enzyme; and a second Fc polypeptide, the method comprising culturing the host cell of claim 9 under conditions in which the polypeptides encoded by the pair of polynucleotides are expressed.

11. A method of treating Pompe disease, the method comprising administering the protein of claim 1 to a patient in need thereof.

12. A method of decreasing the accumulation of a toxic metabolic product in a patient having Pompe disease, the method comprising administering the protein of claim 1 to the patient.

13. The method of claim 12, wherein the toxic metabolic product is glycogen.

14. A protein comprising:
   (a) a fusion polypeptide comprising a first Fc polypeptide linked to an acid alpha-glucosidase (GAA) enzyme, wherein the fusion polypeptide comprises SEQ ID NO: 70; and
   (b) a second Fc polypeptide comprising SEQ ID NO:43.

15. A composition comprising the protein of claim 14 and a pharmaceutically acceptable excipient.

16. A protein comprising:
   (a) a fusion polypeptide comprising a first Fc polypeptide linked to an acid alpha-glucosidase (GAA) enzyme, wherein the fusion polypeptide comprises SEQ ID NO: 70; and
   (b) a second Fc polypeptide comprising SEQ ID NO:44.

17. A composition comprising the protein of claim 16 and a pharmaceutically acceptable excipient.

* * * * *